US009464969B2

(12) United States Patent
Oberg et al.

(10) Patent No.: US 9,464,969 B2
(45) Date of Patent: Oct. 11, 2016

(54) MONOLITHS

(71) Applicants: Monolythix, Inc., Camarillo, CA (US);
Alfred E. Mann Foundation for Scientific Research, Santa Clarita, CA (US)

(72) Inventors: Keith A. Oberg, Valencia, CA (US);
Mark D. Dobbs, Camarillo, CA (US);
Ekaterina Tkatchouk, Camarillo, CA (US); Scott P. Layne, Los Angeles, CA (US); Milton Lee, Camarillo, CA (US)

(73) Assignee: Monolythix, Inc., Camarillo, CA (US)

( * ) Notice: Subject to any disclaimer, the term of this patent is extended or adjusted under 35 U.S.C. 154(b) by 0 days.

(21) Appl. No.: 14/549,055

(22) Filed: Nov. 20, 2014

(65) Prior Publication Data
US 2016/0146714 A1 May 26, 2016

(51) Int. Cl.
| G01N 1/28 | (2006.01) |
| C08J 9/28 | (2006.01) |
| C12Q 1/68 | (2006.01) |
| G01N 21/49 | (2006.01) |
| G01N 21/59 | (2006.01) |

(52) U.S. Cl.
CPC ............ G01N 1/28 (2013.01); C08J 9/286 (2013.01); C12Q 1/6813 (2013.01); C12Q 1/6844 (2013.01); G01N 21/49 (2013.01); G01N 21/59 (2013.01); C08J 2335/02 (2013.01); G01N 2021/495 (2013.01)

(58) Field of Classification Search
CPC ...................................................... G01N 1/28
See application file for complete search history.

(56) References Cited

U.S. PATENT DOCUMENTS

| 5,728,457 | A | 3/1998 | Frechet et al. |
| 5,939,259 | A | 8/1999 | Harvey et al. |
| 6,887,384 | B1 | 5/2005 | Frechet et al. |
| 7,691,263 | B1 * | 4/2010 | Gu .................. B01J 20/267 |
| | | | 210/198.2 |
| 7,846,383 | B2 | 12/2010 | Song |
| 7,867,780 | B2 | 1/2011 | Jones et al. |
| 8,703,058 | B1 * | 4/2014 | Hatch ............... B01L 3/502707 |
| | | | 422/527 |
| 2004/0101442 | A1 | 5/2004 | Frechet et al. |
| 2005/0023456 | A1 | 2/2005 | Frechet et al. |
| 2005/0202427 | A1 | 9/2005 | Soufla |
| 2006/0040406 | A1 | 2/2006 | Jones et al. |
| 2008/0116137 | A1 | 5/2008 | Bonn et al. |
| 2010/0143905 | A1 | 6/2010 | Lane et al. |
| 2011/0033663 | A1 | 2/2011 | Svec et al. |
| 2012/0264116 | A1 | 10/2012 | Michlitsch |
| 2012/0276576 | A1 | 11/2012 | Haddad et al. |
| 2013/0139834 | A1 | 6/2013 | Karlsson et al. |
| 2014/0031952 | A1 | 1/2014 | Harshbarger et al. |
| 2014/0041462 | A1 | 2/2014 | Beerling et al. |
| 2014/0127669 | A1 | 5/2014 | Hilder et al. |
| 2014/0178252 | A1 | 6/2014 | Hatch et al. |
| 2014/0295415 | A1 | 10/2014 | Rolland et al. |
| 2014/0356874 | A1 | 12/2014 | Bearinger et al. |

FOREIGN PATENT DOCUMENTS

| GB | 2477093 | 7/2011 |
| WO | 2005098439 | 10/2005 |
| WO | 2007120808 | 10/2007 |
| WO | 2008007359 | 1/2008 |

OTHER PUBLICATIONS

Partial International Search Report relating to co-pending PCT Application No. PCT/US2014/066643 dated Aug. 3, 2015; 6 Pages.
Bakry, R.,et al., "Monolithic Porous Polymer Layer for the Separation of Peptides and Proteins Using Thin-Layer Chromatograohy Coupled with MALDI-TOF-MS", Analytical Chemistry, 2007, vol. 79; pp. 1-8.
Bhattacharyya, A., et al., "Thermoplastic Microfluidic Device for On-Chip Purification of Nucleic Acids for Disposable Diagnostics", Analytical Chemisty, Feb. 1, 2006, vol. 78, No. 3; pp. 788-792.
Chatterjee, A., et al., "RNA Isolation from Mammalian Cells Using Porous Polymer Monliths: An Approach for High-Throughput Automation", Analytical Chemistry, Jun. 1, 2010, vol. 82, No. 11; pp. 4344-4356.
Frechet, J., "Immobilization of Enzymes onto Porous Monolithic Polymer Supports to Facilitate Fabrication of Micro-and Nanofactories", http://www.nsec.ohio state.edu/briefs/Immobilization.pdf, Document created Feb. 14, 2008; 2 Pages.
Millipore Corp., Hi-Flow Plus Membranes and SureWick Pad Materials, Lit. No. PB1267EN00, Rev 05/08, Diagnostics-08-00087, 2008; pp. 1-10.
Millipore Corp., "Rapid Lateral Flow Test Strips: Considerations for Product Development", Lit. No. TB500EN00 Rev B 05/08, Diagnostics-08-00161, 2008, pp. 1-39.
Potter, O., et al., "Porous polymer monoliths for extraction: Diverse applications and platforms", Journal of Separation Science, 2006, vol. 31; pp. 1881-1906.
Shkolnikov. V., et al., "Design and fabrication of porous polymer wick structures", Sensors and Actuators B: Chemical, 2010, vol. 150, pp. 556-563.
Wong, R., et al., "Lateral Flow Immunoassay", ISBN 978-1-58829-908-6, e-ISBN 978-1-59745-240-3; DOI 10.1007/978-1-59745-240-3, Humana Press, 2009; pp. 1-223.

(Continued)

Primary Examiner — Wenwen Cai
(74) Attorney, Agent, or Firm — McCarter & English, LLP

(57) ABSTRACT

The present invention relates to a monolith for processing fluid samples, and methods of making and using the monolith. The monolith can contain certain monomers or combinations of monomers that can be polymerized to give a polymeric monolith that can efficiently self-wick fluid. The self-wicking polymeric monolith can be used as a convenient tool for point of care on site diagnostics and analytics. The monolith is easily stored and transported, comparatively cost-efficient to make, permits good detection of analyte molecules and is readily functionalizable by impregnation of and/or covalently grafting additional chemical moieties to either the whole monolith or in zones.

140 Claims, 13 Drawing Sheets

(56) References Cited

OTHER PUBLICATIONS

Bechtle, M., "Preparation of macroporous methacrylate-based monoliths for chromatographic applications", Dissertation No. 18401; Institute for Chemical and Bioengineering, ETH Zürich: 2009; pp. 1-99.

International Search Report and Written Opinion relating to co-pending PCT Application No. PCT/US2014/066643 dated Oct. 22, 2015; 17 Pages.

* cited by examiner

— ■ — grafted dye
— ● — not covalently grafted dye

———■——— Flu LAMP reaction in neutral monolith
———♦——— Flu LAMP reaction in liquid control ———— Liquid NESA Reaction
— — — Liquid NESA Reaction plus Uncoupled Bead Slurry
·········· NESA reaction in Probe-coupled Bead Slurry
++++++++++ NESA with Uncoupled Bead Slurry Control (no probe)

METHOD 1000 FOR FABRICATING MONOLITH 910
USING THE APPAPRATUS OF FIGURE 20

1001 Providing mold 905 configured for the fabrication of monolith 910,

1002 Defining a plurality of zones (912, 914, 916, 918) in the mold;

1003 Providing a plurality of nozzles (922, 924, 926, 928), wherein each one of the plurality of nozzles is associated with one of the plurality of zones;

1004 Dispensing one or more monomers of a plurality of hydrophilic monomers into one of the plurality of nozzles;

1005 Dispensing one or more porogenic solvents of a plurality of porogenic solvents into one of the plurality of nozzles;

1006 Dispensing one or more linker monomers of a plurality of linker monomers into one of the plurality of nozzles;

1007 Dispensing one or more initiators of a plurality of initiators into one of the plurality of nozzles;

1008 Repeating 1004, 1005, 1006 and 1007 until each of the plurality of nozzles has received at least one hydrophilic monomer, at least one porogenic solvent, at least one linker monomer and at least one initiator;

1009 Mixing the contents of each one of the plurality of nozzles;

1010 Metering the contents of each one of the plurality of nozzles into each one of the respective plurality of zones in the mold;

1011 Initiating polymerization of the contents of the mold;

1012 Completing polymerization of the contents of the mold and thus forming the monolith; and 1013 Washing remaining solvent from the monolith.

Figure 21

METHOD 1200 FOR FABRICATING MONOLITH 1110
USING THE APPARATUS OF FIGURE 22

1201 Providing mold 1105 and a plurality of dividers (1113, 1115, 1117) configured for the fabrication of monolith 1110;

1202 Positioning the plurality of dividers in the mold to define the plurality of zones (1112, 1114, 1116, 1118);

1203 Providing a plurality of nozzles (1122, 1124, 1126, 1128), wherein each one of the plurality of nozzles is associated with one of the plurality of zones;

1204 Dispensing one or more monomers of a plurality of hydrophilic monomers into one of the plurality of nozzles;

1205 Dispensing one or more porogenic solvents of a plurality of porogenic solvents into one of the plurality of nozzles;

1206 Dispensing one or more linker monomers of a plurality of linker monomers into one of the plurality of nozzles;

1207 Dispensing one or more initiators of a plurality of initiators into one of the plurality of nozzles;

1208 Repeating 1204, 1205, 1206 and 1207 until each of the plurality of nozzles has received at least one hydrophilic monomer, at least one porogenic solvent, at least one linker monomer and at least one initiator;

1209 Mixing the contents of each one of the plurality of nozzles,

1210 Metering the contents of each one of the plurality of nozzles into each one of the respective plurality of zones in the mold;

1211 Initiating polymerization of the contents of the mold;

1212 Monitoring the status of the polymerization in the mold;

1213 Removing the plurality of dividers from the mold before the contents solidify;

1214 Completing polymerization of the contents of the mold and thus forming one contiguous monolith; and 1215 Washing remaining solvent from the monolith.

Figure 23

MONOLITHS

FIELD OF THE INVENTION

The present invention relates to monoliths for processing fluid samples, and to methods of making and using such monoliths.

INTRODUCTION

Most disposable point of care diagnostics make use of chromatographic and/or lateral flow methods, with nitrocellulose membranes, glass fiber conjugate pads and cellulose absorbent pads constituting the base materials as described in Millipore Rapid Lateral Flow Test Strips: Considerations for Product Development. Lit. No. TB500EN00, Rev. B, 05/08, Diagnostics-08-00161, pages 37-38, 2008 and in Lateral Flow Immunoassay. Wong and Tse, Humana Press, 2009: ISBN 978-1-58829-908-6; ISBN 978-1-59745-240-3; DOI 10.1007/978-1-59745-240-3. In many instances, such devices are composed of all three materials as described in Millipore Hi-Flow Plus Membranes and SureWick Pad Membranes, Lit. No. PB1267EN00, Rev. 05/08, Diagnostics-08-00087, 2008.

These are single-step, disposable devices for determining the presence of specific antigens, such as hormones or drugs, in biological samples.

Lateral flow tests are generally constructed from a series of at least four wick segments arranged in a linear series. Each of these segments is typically made from a specific material with properties tailored to optimally perform a particular role in the overall analysis.

A sample applied to a typical test strip is drawn first into a sample pad typically made from non-woven, bibulous fibers. The sample pad plays the role of filtering out solids and modifying the sample fluid to be compatible with downstream assay components by, for example, releasing buffer into the sample matrix.

The segment following the sample pad typically contains some of the assay reagents. In the most common assay configurations, antibody-coated colored beads are swept into the passing sample fluid.

The sample is then wicked into a nitrocellulose detection segment where at least one other antibody has been immobilized in capture lines. Control lines are commonly included. As the analyte-bound conjugate beads pass the capture lines they are retained by the immobilized antibodies. If a sufficient number of beads are captured at a given line, visible color develops.

After the fluid passes the capture lines, it is wicked into a final absorbent pad which has a fluid capacity sufficient to ensure that an adequate amount of the sample is wicked past the capture lines.

More recently, two commercial materials have been marketed as single-matrix replacements for the various constituent materials in most lateral flow test devices. The significant feature of these materials is that a single unit of either can be used as an entire test strip with no conditioning treatments and no mechanical joints between zones.

Fusion 5 (Whatman) is a material made from bonded glass fibers that are coated with hydrophilic polymer. Structurally, these membranes are similar to the materials most commonly used for the sample pad, conjugate pad, and sink. What distinguishes Fusion 5 from the typical materials used is an inert, biocompatible polymer coating that eliminates the need for any rewetting or blocking steps during manufacture. In addition, this material can also assume the role of the classic nitrocellulose detection segment if it is impregnated with large beads coated with capture reagent. Beads on the scale of the pore size do not migrate through the matrix.

The 4Cast Chip (Johnsen and Johnsen) is formed of a regular array of microscale pillars arranged in the form of a strip on a rigid plastic support. The pillars are formed by injection molding and hydrophilised by Dextran. These pillar arrays wick via capillary forces and can therefore perform the functions of both the fibers and cast nitrocellulose film. The chip is delivered in a condition where it is reactive with the amino groups on proteins, so capture antibodies can be covalently immobilized onto the pillar structure by simply spotting antibody solutions on the matrix.

SUMMARY

The present invention is based on the inventors' insight that there exists a need for improved alternative fluid processing materials meeting the criteria of ease of use, diversity of supported chemistries, economy of manufacture, high sensitivity and are readily functionalizable.

Although functional and available, nitrocellulose has several major drawbacks. First, commercial nitrocellulose membranes have uniform compositions and/or average pore sizes, which limits the variety of processes and/or chemistries that can be achieved for each specific one. Second, high optical density and high light backscatter limit visible depths (typically ~10 microns) into nitrocellulose membranes and thereby limit detection sensitivities for diagnostic devices.

Other, more sophisticated test strips are known. However, complex arrangements and multiple components means that these test strips may be costly to make.

Throughout the developed and developing world, there is a compelling need for reliable and affordable point of use and/or point of care diagnostic and analytical technologies that are highly sensitive and specific. Such diagnostics are not widely available, however, primarily because they are not cost effective and/or hard to use. Furthermore, for some uses, it is highly desirable to provide disposable point of need diagnostics. For any test device to be disposable, cost becomes a key concern.

In resource-limited settings, the cost of simple dipstick/teststick-based tests must approach $1 per unit. Clearly, this cost restriction precludes complicated manufacturing methods and set ups.

The present inventors have discovered that certain monomers and combinations of monomers can be polymerized to give polymeric monoliths that efficiently self-wick fluid, offering a convenient tool for point of care/on site diagnostics and analytics. These self-wicking polymeric monoliths are easily stored and transported, comparatively cost-efficient to make, permit good detection of analyte molecules and are readily functionalizable by impregnation of and/or covalently grafting additional chemical moieties to either the whole monolith or in zones.

In use, an analyte sample, either as an isolated fluid or in carrier fluid may flow through the self-wicking monolith from the beginning to the end of a test process without the need for pumps or other powered devices.

The present invention is based on the inventors' insight that monoliths formed from a polymerizable composition comprising linkers having at least one —$C(R)_2O$— group offer a useful tool for fluid processing and fluid diagnostics. The present invention therefore relates to method of making monoliths using monomers comprising linkers having at least one —$C(R_2O$— group, monoliths comprising linkers having at least one —C(R)₂O— group, and methods of using such monoliths. The present inventors have found that monoliths formed from a monomers having at least one —C(R)₂O— group and monomers that are hydrophilic are especially suitable for many of these purposes.

In a first aspect, the present invention may provide a method of fabricating a self-wicking monolith for processing a fluid sample, the method comprising:

providing a hydrophilic monomer and a linker monomer, the linker monomer having two polymerizable groups spaced apart by a linker comprising at least one —C(R)₂ O— group; optionally wherein one or more further monomers are provided;

obtaining a polymerizable composition by combining said hydrophilic monomer and linker monomer in a porogenic solvent; and polymerizing the polymerizable composition to form the monolith.

Each R may be hydrogen, or may be any organic group. Put another way, the linker may comprise an alkyl or substituted alkyl chain —(C(R)₂)ₙ— in which at least one, preferably at least two, —C(R)₂— groups are replaced by oxygen. Suitably, n is 3 to 20, for example, 5 to 15, for example, 5 to 13. The R groups may themselves include further polymerizable groups. In other words, preferably the linker is a polyether, for example, a polyethylene glycol or similar. Suitably, the linker comprises a polyethylene glycol chain, for example containing 1, 2, 3, 4, 5 or more —OC(R)₂C(R)₂— groups, for example, 1, 2, or 3 —OC(R)₂C(R)₂— groups.

The polymerizing step forms a polymeric matrix, i.e. the monomers are polymerized to give a monolith that is a substantially continuous polymeric network. The monolith may therefore be loosely termed a macroscale single molecule.

After the polymerisation step, the monolith may be separated from the residual unpolymerized material. This may be unpolymerized monomers, short oligomer chains not bound to the polymer matrix, initiator by-products, and/or residual solvent.

Suitably, residual unpolymerized material may be removed in a washing step (i.e. washed away). This residual unpolymerized material may be solid and/or liquid. For example, in a washing step the monolith may be washed with an alcohol and/or water. The washing step may include forcing the liquid through the monolith through application of a pressure differential.

In some preferred methods, the monolith is washed first with an alcohol (for example, methanol, ethanol, or isopropanol) and then washed with water. For example, the monolith may be washed thrice with an alcohol and then thrice with water.

Suitably, the monolith is then dried until constant weight (that is, no more solvent remains). For the drying step, a vacuum oven may be used).

Each of the polymerizable groups of the linker monomer may comprise a vinylic moiety. For example, each polymerizable group of the linker molecule may be independently selected from acryl or methacryl.

In some embodiments, the linker is selected from —O—CH₂—CH₂—O—; —(—O—CH₂—CH₂—)ₙ—O—, wherein n is selected from 2, 3, 4, or 5; —O—CH₂—CH(OH)—CH₂—O—; and —O—CH₂—CH(OH)—CH₂—CH(OH)—CH₂—CH(OH)—CH₂—O—.

It will be appreciated that the linker monomer may comprise further polymerizable groups, for example, the linker may be —OCH₂—C(CH₂O—)(CH₂CH₃)—CH₂O—, wherein — represents a bond to a further polymerizable group.

Suitable such linker monomers include ethyleneglycol diacrylate, ethyleneglycol dimethacrylate, tetra(ethylene glycol) dimethacrylate, tetra(ethylene glycol) diacrylate, and di(ethylene glycol) dimethacrylate.

Suitably, the hydrophilic monomer is an acrylate or methacrylate, for example, the hydrophilic monomer may be 2-hydroxyethyl methacrylate (HEMA), 2-hydroxyacrylate, 2-hydroxyethyl acrylate, 2-hydroxypropyl methacrylate or 2-hydroxypropyl acrylate. In some preferred embodiments, it is 2-hydroxyethyl methacrylate.

Of course, it will be appreciated that more than one linker monomer may be used. Accordingly, in some embodiments, two or more different linker monomers are combined with the hydrophilic monomer in the porogenic solvent. In some embodiments, only one linker monomer is used. In some embodiments, two linker monomers are used. In some embodiments, three linker monomers are used. Combinations of linker monomers may give rise to improved physical properties of the monolith.

Some preferred combinations of linker monomers include: ethylene glycol dimethacrylate, and tetraethylene glycol dimethacrylate; ethylene glycol dimethacrylate and tetraethylene glycol diacrylate. For example, a combination of linker monomers may be ethylene glycol dimethacrylate and tetraethylene glycol diacrylate, for example in a ratio of 4:3 to 1:3, for example in a ratio of 1:1 to 1:3, for example, in a ratio of 2:3 to 7:10. For example, a combination of linker monomers may be ethylene glycol dimethacrylate and tetraethylene glycol dimethacrylate, for example in a ratio of, 5:1 to 1:1, for example, in a ratio of around 3:1.

For example, the ratio of tetraethylene glycol dimethacrylate to hydrophilic monomer, for example, HEMA, may be 5:2 to 1:3, for example, 2:1 to 1:1. In some embodiments, the ratio of tetraethylene glycol dimethacrylate to hydrophilic monomer, for example, HEMA, may be 1:1 to 7:10. For example, the ratio of tetraethylene glycol diacrylate to hydrophilic monomer, for example, HEMA, may be 5:2 to 1:3, for example, 2:1 to 1:1. In some embodiments, the ratio of tetraethylene glycol diacrylate to hydrophilic monomer, for example, HEMA, may be 1:1 to 7:10.

The polymerizable composition may additionally include one or more further monomers. Accordingly, in some embodiments, one or more further monomers are combined with the hydrophilic monomer in the porogenic solvent. The inclusion of said further monomers may alter the physical characteristics of the monolith and/or may impart functionality to the monolith.

For example, at least one further monomer may be a functionalised monomer. Said functionalised monomer may bear a moiety selected from a chemically reactive group suitable for reaction with a reactive group of a graftable compound to covalently graft the compound to the monolith; a pH sensitive group; a group suitable for direct immobilisation of an analyte; a dye, fluorophore, chromophore, or quencher; an immobilised protein; and immobilised natural or artificial nucleic acid molecules, for example, DNA or RNA molecules. These groups are described in detail later in this specification, but by way of example and not by way of limitation, a further monomer may comprise a least one of the following side chains or groups: amino, carboxyl, polyethylene glycol, alkyl, maleimide, succinimide, acyl halide, sulfhydryl or azide.

The or each further monomer (if present) may comprise at least one of the following side chains or groups: amino, carboxyl, polyethylene glycol, alkyl, maleimide, succinimide, acyl halide, sulfhydryl or azide. For example, in some embodiments, a further monomer may be selected from 2-aminoethylmethacrylate, tertbutylaminoethylmethacrylate methacrylic acid, acrylic acid, 2-(diethylamino)ethyl methacrylate, methacrylic acid N-hydroxysuccimide ester, 2-acrylamido-2-methyl-1-propanesulfonic acid, glycidyl methacrylate, mono-2-(methacryloxy)ethyl succinate, lauryl methacrylate, butyl methacrylate, allyl methacrylate.

For example, in some embodiments, a further monomer may be selected from 2-aminoethylmethacrylate, tertbutylaminoethylmethacrylate, methacrylic acid, methacrylic acid N-hydroxysuccimide ester, 2-acrylamido-2-methyl-1-propanesulfonic acid, glycidyl methacrylate, and lauryl methacrylate.

It will be appreciated that the further monomer may be selected depending on intended function (for example, having side chains suitable for covalent grafting reactions as described herein).

In some preferred methods, the further monomer is an amino methacrylate or amino acrylate, for example a (dialkylamino)alkyl methacrylate or a (dialkylamino)alkyl acrylate, for example, 2-(diethylamino)ethyl methacrylate or 2-(diethylamino)ethyl acrylate. Suitably, the further monomer which is an aminoalkyl methacrylate or aminoalkyl acrylate is pH sensitive.

In some embodiments, a further monomer may be 2-aminoethyl methylacrylate.

In some preferred methods, the further monomer comprises a free carboxylic acid group. For example, the further monomer may be acrylic acid or methacrylic acid.

Suitably, the total further monomer content is 1-3% of the total monomer content of the polymerizable composition, for example, it may be 1-2.5%, preferably 1-2%, more preferably, 1.25-1.75%.

Suitably, the total linker monomer to total hydrophilic monomer ratio may be from 1:1 to 10:1, preferably from 1:1 to 7:1, more preferably from 1:1 to 5:1, more preferably from 2:1 to 4:1. Suitably, the total linker monomer to total other monomer content (hydrophilic monomer plus further monomer) is from 1:1 to 10:1, preferably from 1:1 to 7:1, more preferably from 1:1 to 4:1.

The porogenic solvent may be selected to suit the desired monolith properties.

In some preferred methods, the porogenic solvent is able to dissolve solid monomers, and/or the porogenic solvent is miscible with liquid monomers.

Suitably, the porogenic solvent may be selected such that linker polymer clusters precipitate from the porogenic solvent at an early point in polymerization. For example, the porogenic solvent may be selected such that clusters of polymerized linker monomer will precipitate from the solvent-monomer system within 30-60 seconds of initiating polymerization.

Single solvent systems or mixed solvent systems may be used.

For example, the porogenic solvent may be a pure alcohol.

For example, the porogenic solvent may be selected from a binary mixture containing an alkane and an alcohol; a binary mixture containing an aromatic solvent and an alcohol; a binary mixture containing an alcohol and a diol; a binary mixture containing an alcohol and water; a ternary mixture containing an alcohol, a diol and water; and a mixture containing at least 10% (v/v) surfactant.

For example, the solvent system may comprise a $C_{8-12}$ mono alcohol, for example a $C_{8-10}$ monoalcohol, preferably octanol. Of course, the $C_{8-12}$ mono alcohol may itself be a mixture of more than one $C_{8-12}$ mono alcohol (for example, a mixture of octanol and dodecanol). The $C_{8-12}$ mono alcohol may be mixed with one or more further solvents. Suitably, the further solvent is a $C_{1-4}$ mono alcohol or a $C_{2-6}$ diol. The present inventors have found that the inclusion of a $C_{1-4}$ mono alcohol results in an increase in pore size in the resultant monolith, while the inclusion of a $C_{2-6}$ diol increases mechanical strength. Suitable $C_{1-4}$ mono alcohols include, without limitation, methanol, ethanol, n-propanol, i-propanol, and butanol; methanol or n-propanol is preferred. In some embodiments, methanol is included. In some embodiments, n-propanol is included. Suitable $C_{2-6}$ diols include, without limitation, propanediol, pentanediol and hexanediol; pentanediol is preferred.

Suitably, the ratio of $C_{8-12}$ mono alcohol to $C_{1-4}$ mono alcohol is 10:1 to 1:1; for example, it may be 9:1, 8:1, 7:1, 6:1, 5:1, 4:1, 3:1, 2:1, or 1:1. Preferably, the ratio of $C_{8-12}$ mono alcohol to $C_{1-4}$ mono alcohol is 3:2 to 3:1.

Suitably, the ratio of $C_{8-12}$ mono alcohol to $C_{2-6}$ diols 10:1 to 2:1; for example, it may be 9:1, 8:1, 7:1, 6:1, 5:1, 4:1, 3:1, 2:1, 1:1, 2:3, 2:1. Preferably, the ratio of $C_{8-12}$ mono alcohol to $C_{2-6}$ diol is 3:2 to 3:1.

The $C_{8-10}$ monoalcohol solvent systems described may further comprise up to 10% of the total solvent content, preferably up to 5%, water, provided the solvent system is essentially monophasic.

The solvent system may be an aqueous solvent system, for example, a mixture of water, a $C_{1-4}$ mono alcohol and/or acetic acid. Certain preferred aqueous solvent systems may include water and methanol, ethanol, n-propanol or iso-propanol. A preferred ratio of water to further component is 3:1.

Any of the solvent systems described above may further comprise a surfactant, for example, a poloxamer. The presence of a surfactant may aid the initial miscibility of mixed solvent systems as described. Suitably, the surfactant content is up to 10% of the total solvent content, preferably up to 5%.

Alternatively, in some methods the porogenic solvent may be 100% poloxamer.

Certain preferred solvent systems include: a mixture of octanol and butanediol, a mixture of octanol and pentanediol; a mixture of octanol and n-propanol; a mixture of octanol and water; a mixture of ethanol and water; and a mixture of one or more poloxamers and water.

For example, the solvent system may be: n-octanol; octanol:water, 19:1; octanol:$C_{4-6}$-n-diol, 4:1 to 2:3; n-octanol:n-propanol 4:1 to 1:1.

The present invention further provides methods of fabricating monoliths from linker monomers comprising a linker having at least one —$C(R)_2O$— group as described herein, monoliths comprising a linker having at least one —$C(R)_2O$— group as described herein, and methods of using such monoliths. It will be appreciated some monoliths that are described herein may be fabricated from a polymerizable composition that does not necessarily require a hydrophilic monomer. The present invention therefore further provides methods of fabricating such monoliths, the method comprising providing a linker monomer, the linker monomer having two polymerizable groups spaced apart by a linker comprising at least one —$C(R)_2O$— group, optionally wherein one or more further monomers are provided; obtaining a polymerizable composition by combining linker monomer with optional further monomers in a porogenic solvent; and polymerizing the polymerizable composition to form the monolith.

The present invention further provides methods of fabricating monoliths, wherein the method comprises further derivatization after the polymerization step. For example, the method may include a hydrolysis step after the polymerization step, as described herein. Additionally or alternatively, the further derivatization may comprise covalent grafting of graftable compounds and/or impregnation of compounds within the monolith.

The present invention provides monoliths having one or more zones, as described herein. The zones may differ in the composition of the polymeric matrix as a result of the polymerization step, or as a result of treatment and/or derivatization after the polymerization step.

In some embodiments, the method is a method of fabrication wherein more than one composition containing the monomer(s) and linker monomer(s) in a porogenic solvent is provided, wherein two of the compositions vary in at least one of:
   hydrophilic monomer and/or linker monomer identity;
   total non-linker monomer to linker monomer ratio;
   porogenic solvent;
   the concentration of hydrophilic monomer, linker monomer, and further monomer, if present, in the solution;
   the presence and identity of one or more further monomers and
   the presence and identity of an initiator;
the method comprising the step of providing the compositions at different locations within a mold prior to polymerization, such that the monolith comprises a plurality of zones, wherein different zones have different wicking properties and/or chemical properties.

Preferably, the further monomer is a functionalized monomer as described herein.

Suitably, said zones are ordered sequentially along the intended wicking direction of the monolith. However, it will be appreciated that zones may also be provided in parallel along the wicking direction. For example, two zones may be provided side-by-side to permit a control to be run alongside a sample along the monolith.

Zones may also be provided through further derivatization of the monolith after the polymerisation step, for example through covalent grafting of graftable compounds and/or impregnation of compounds within the monolith. Derivatization may also be a result of hydrolysis of, for example, ester groups within the polymeric matrix, as described herein.

The zones of the monolith may be zones as described herein. It will be appreciated that different such zones may be selected according to the desired use. Further details of certain preferred combinations are described in further detail later in this specification.

In some embodiments, the further derivatization comprises the covalent grafting of a graftable compound to the monolith. The graftable compound may be an enzyme. The graftable compound may be an antibody. The graftable compound may be an amphiphile. The graftable compound may be DNA probe.

It will be appreciated that more than one graftable compound may be used, both within a single zone and at different zones within the same monolith. Additionally or alternatively, wherein the further derivatization may comprise the impregnation of one or more components within the monolith.

At least one of the zones may be an amplification zone which is configured to facilitate amplification of a target nucleic acid sequence in a fluid sample. At least one of the zones may be an amplification zone which is configured to facilitate whole-genome amplification in a fluid sample. At least one of the zones may be a clean-up zone which is configured to facilitate lysis of cells in a fluid sample. At least one of the zones may be a clean-up zone which is configured to facilitate lysis of viruses in a fluid sample. At least one of the zones may be a reverse transcription zone which is configured to facilitate transcription of RNA to cDNA. At least one of the zones may be an indication zone which is configured to facilitate detection of an analyte molecule, optionally wherein said zone includes at least one of a dye fluorophore, a chromophore, and a quencher, optionally wherein the analyte molecule is DNA. At least one of the zones may be configured to retard or retain one or more components of the sample such that ah analyte is separated from other components in the sample. At least one of the zones may be configured to facilitate a chemical transformation of one or more components of the sample. It will be appreciated that one or more than one of these zones may be provided.

Suitably, the monolith is provided in the form of a test stick. In these embodiments, the monolith may have a single intended wicking direction. In some preferred embodiments, the monolith has external dimensions of length: between 1 and 10 cm; width: between 2 and 25 mm; depth: between 1 and 10 mm.

Alternatively, the monolith may be shaped such that it provides one or more branches that divide and combine fluid flowing through the monolith.

The monolith may be of fixed width and or depth along the intended wicking direction, or it may comprise one or more neck regions (these being regions of reduced cross-sectional area). For example, a depth of less than 5 mm, preferably less than 4 mm, more preferably less than 3 mm, most preferably less than 2 mm, may be desirable in at least one part of the monolith to permit transillumination to facilitate detection. Accordingly, the polymerisation step may occur in a mold shaped so as to provide a monolith having one or more neck regions.

In some embodiments, the total linker monomer to total non-linker monomer ratio is 1:3 to 20:1, more preferably 1:1 to 5:1, more preferably 2:1 to 4:1. A preferred ratio is 3:1.

In some embodiments, the monolith comprises one or more regions having a porosity of 50-85%.

In a second aspect, the present invention may provide a self-wicking monolith fabricated according to any method of the first aspect.

In a third aspect, the present invention may provide a self-wicking monolith for processing a fluid sample, the monolith comprising a polymeric network formed from a polymerizable composition including at least one hydrophilic monomer and at least one linker monomer, the linker monomer having two polymerizable groups spaced by a linker comprising at least one —C(R)$_2$O— group.

The monolith may comprise a plurality of zones, said zones being ordered sequentially along the intended wicking direction of the monolith and/or in parallel along an intended wicking direction of the monolith, wherein different zones have different wicking properties and/or chemical properties.

In a fourth aspect, the present invention may provide a monolith comprising a continuous polymeric network, the monolith comprising a plurality of zones, said zones being ordered sequentially along the intended wicking direction of the monolith and/or in parallel along an intended wicking direction of the monolith, wherein different zones have different wicking properties and/or chemical properties.

The zones of the monolith may be zones as described herein. It will be appreciated that different such zones may be selected according to the desired use. Further details of certain preferred combinations are described in further detail later in this specification.

In some embodiments, the monolith is provided in the form of a test stick. In these embodiments, the monolith may have a single intended wicking direction. In some preferred embodiments, the monolith has external dimensions of length: between 1 and 10 cm; width: between 2 and 25 mm depth: between 1 and 10 mm.

Alternatively, the monolith may be shaped such that it provides one or more branches that divide and combine fluid flowing through the monolith.

The monolith may be of fixed width and/or depth along the intended wicking direction, or it may comprise one or more neck regions (these being regions of reduced cross-sectional area). For example, a depth of less than 5 mm, preferably less than 4 mm, more preferably less than 3 mm, most preferably less than 2 mm, may be desirable in at least one part of the monolith to permit transillumination to facilitate detection.

In some embodiments, the bulk density of the monolith is between 0.15 and 0.50 g/cc, for example 0.20 and 0.40 g/cc. The monolith may comprise one or more regions having a porosity of 50-85%, for example, 60-85%.

Of course, it will be appreciated that, in multi-zoned monoliths as described herein, and in methods of fabrication of multi-zoned monoliths as described herein, different zones may have different bulk densities and/or porosities. For example, a multi-zone monolith may comprise a first zone having a first bulk density value and a second zone (before or after the first zone in the intended wicking direction) having a second bulk density different to the first.

For example, a multi-zone monolith may comprise a first zone having a porosity between 50-85%, and a second zone (before or after the first zone in the intended wicking direction) having a porosity between 50-85%, wherein the porosity of the first zone is different to the porosity of the second zone.

It may be useful to control the temperature of the monolith, or a portion of the monolith (for example, a zone) during use. Accordingly, in some embodiments, the monolith may have a temperature sensor thermally coupled to the monolith and/or a heating element thermally coupled to the monolith. There may further be provided a controller coupled to the temperature sensor and/or the heating element, the controller being configured to regulate the temperature of at least a portion of the monolith.

For some applications, it may be preferable for handling purposes for the monolith to be flexible and/or pliable (in other words, not brittle). For example, a 30 mm long span of monolith with a 12×1.5 mm cross section may have a Young's modulus of less than 2 psi, for example, less than 1 psi. In some embodiments, the monolith may have a Young's modulus of less than 0.5 psi, for example, less than 0.3 psi. In some embodiments, the monolith may have a Young's module of less than 0.1 psi, for example, less than 0.05 psi.

Monoliths as described herein may be used with an apparatus suitable for illuminating a portion of the monolith, for example, an indication zone, to facilitate detection of an analyte. Accordingly, in a fifth aspect, the present invention relates to an apparatus comprising a monolith as described herein and an optical source configured to illuminate a portion of the monolith with light.

Suitably, the apparatus further comprises an optical sensor configured to receive the light either reflected from or transmitted through the monolith. A controller may be provided, the controller being coupled to the optical source and to the optical sensor, and configured to control the optical source and to receive optical data from the optical sensor.

Accordingly, in a sixth aspect the present invention may provide an apparatus comprising a monolith as described herein, and further comprising:
- an optical source configured to illuminate a portion of the monolith with light;
- an optical sensor configured to receive the light either reflected from or transmitted through the monolith; and
- a controller coupled to the optical source and to the optical sensor, wherein the controller is configured to control the optical source and to receive optical data from the optical sensor.

The controllers described above may also be configured to determine if an analyte is present.

The apparatus may further comprise an interface coupled to the controller configured to receive the data from the optical sensor, and a communications device coupled to the interface via a wireless or wired connection, the communications device being configured to receive the data from the optical sensor via the interface from the controller. Through processing of these data, a determination may be made, thereby determining whether or not a target analyte has been detected in the fluid sample. The target analyte may, for example, be a target DNA sequence.

The communications device may be coupled to a telecommunications network or to a web service coupled to the Internet. This may be advantageous in processing data, storing results and/or relaying results to interested parties.

For example, the communications device may process the data and make a determination, or it may relay the data to a further device or cloud-based information system to be processed. The result of the data processing (for example, determination as to whether or not an analyte is present) may be relayed back to the apparatus for point of use determination.

In another aspect, the present invention provides an apparatus comprising a monolith as described herein, and further comprising:
- an optical sensor configured to receive the light emitted from a compound in or on the monolith, said light emission indicating the presence of an analyte; and
- a controller coupled to the optical sensor; wherein the controller is configured to process the data received and to determine if an analyte has or has not been detected in the fluid sample in the indication zone; and
- a visual indicator or display coupled to the controller, the visual indicator or display receives a signal from the controller to provide a visual cue or message that the analyte has or has not been detected.

The apparatus may further comprise an optical source configured to illuminate at least a portion of the monolith, for example, an indication zone.

The apparatus may further comprise a visual indicator or display coupled to the controller, wherein the controller is configured to determine the presence or absence of the analyte in the fluid sample and to generate a visual cue or message at the visual indicator or display indicative of the presence or absence of the analyte.

The apparatus may further comprise an interface coupled to the controller and configured to receive the data from the controller; and a communications device coupled to the interface via a wired or wireless connection, the communications device includes a visual display, the communications device receives the data from the controller via the interface, the communication device processes the data to determine if the analyte has or has not been detected in the fluid sample in the indication zone and the communications device provides a visual cue or message that the analyte has been or has not been detected. The communications device may be coupled to a telecommunications network or to a web service coupled to the Internet.

As described herein, it may be desirable to control the temperature of the monolith during use. The apparatus may therefore comprise one or more temperature sensors thermally coupled to one or more of the plurality of zones; one or more heating elements thermally coupled to the one or more of the plurality of zones; and a controller coupled to the one or more temperature sensors and the one or more heating elements, wherein the controller is configured to regulate the temperature of the one or more plurality of zones.

The present invention also provides uses of monolith according to any other aspect of the invention in diagnostic methods and environmental monitoring methods.

Accordingly, in a seventh aspect, the present invention may provide use of a monolith as described herein in a diagnostic method, the method comprising:

providing a fluid sample comprising one or more analyte molecules;
optionally pre-processing the fluid sample;
optionally diluting the fluid sample in a carrier fluid;
applying the fluid sample to a sample application portion of the monolith;
optionally applying additional carrier fluid to the monolith;
detecting an analyte molecule at an indication portion of the monolith, the indication portion being spaced from the sample application portion.

In an eighth aspect, the present invention may provide use of a monolith as described herein in an environmental monitoring method, the method comprising:

providing an environmental sample suspected to include one or more analyte molecules;
optionally pre-processing the environmental sample (for example, by concentrating the sample);
optionally diluting the environmental sample in a carrier fluid;
optionally extracting the environmental sample with a carrier fluid, and discarding insoluble materials;
applying the environmental sample to a sample application portion of the monolith;
optionally applying additional carrier fluid to the monolith;
detecting an analyte molecule at an indication portion of the monolith, the indication portion being spaced from the sample application portion.

In a ninth aspect, the present invention relates to an apparatus comprising first and second monoliths and an enclosure for holding the first and second monoliths in fluid communication with each other; wherein a junction is formed by abutting surfaces of the first and second monoliths, such that a sample applied to the first monolith wicks into the second monolith.

Either or both of the first and second monoliths may be a monolith as described herein. Optionally, one of the monoliths may be a different type of wicking material, for example, a block of nitrocellulose as already known in the art. Suitably, both first and second monoliths are monoliths of the present invention.

Accordingly, in another aspect, the present invention may provide an apparatus comprising: a first monolith as described herein and a second monolith as described herein; and an enclosure for holding the first and second monoliths in fluid communication with each other; wherein a junction is formed by abutting surfaces of the first and second monoliths, such that a sample applied to the first monolith wicks into the second monolith.

It will be appreciated that the apparatus of the above aspect may optionally further comprise features described with respect to other apparatus herein. For example, the apparatus may comprise an optical source configured to illuminate a portion of at least one of the monoliths with light, an optical sensor configured to receive the light either reflected from or transmitted through said monolith; and a controller coupled to the optical source and to the optical sensor, wherein the controller is configured to control the optical source and to receive optical data from the optical sensor. It will be appreciated that a visual indicator as described herein may also be provided. For example, the apparatus may further comprise temperature sensors and heating elements as described herein, which may be controlled by a controller.

It will be appreciated that, except where such a combination is clearly impermissible, preferences and optional features described with respect to any monolith described herein may equally apply to any other monolith. Similarly, preferences and optional features described with respect to methods of fabricating monoliths apply equally to the monoliths themselves and vice versa.

DETAILED DESCRIPTION

Figures

Through this specification, the aspects of the invention are further described, without limitation, with reference to the following figures in which.

Figure 5:
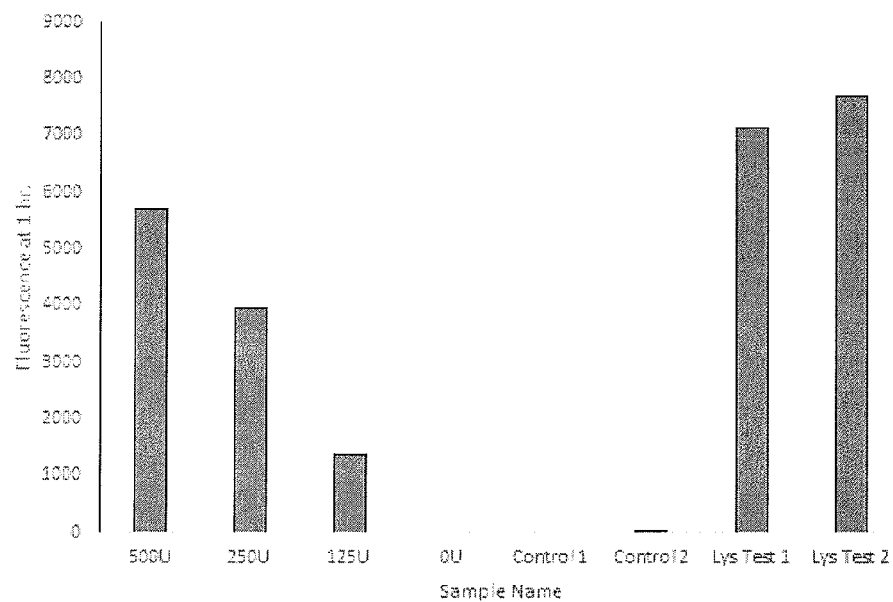

FIG. 5 shows a bar graph of measured fluorescence in the EnzChek® Lysozyme Assay. Coupled Lysozyme Test 1 and 2 are the two polymeric matrix-immobilized lysozyme samples, Negative Control 1 and 2 are the negative controls. The U numbers refer to the U/mL values.

Figure 6:
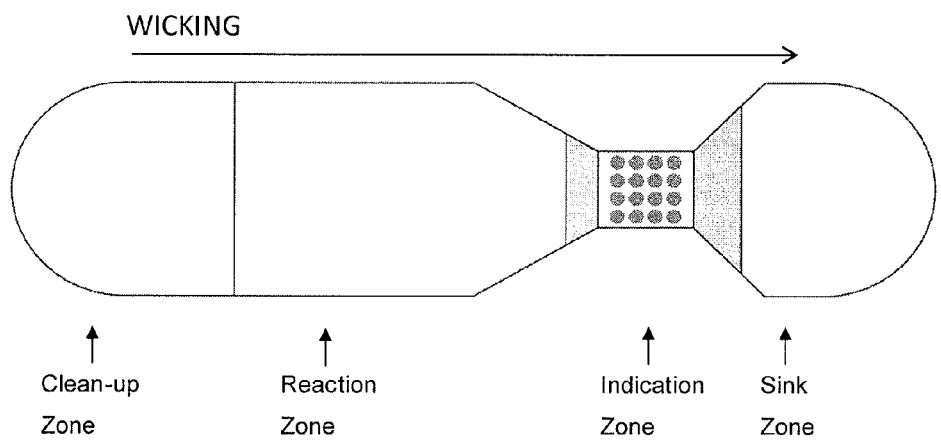

FIG. 6 shows an exemplary 4 zone monolith.

Figure 7:
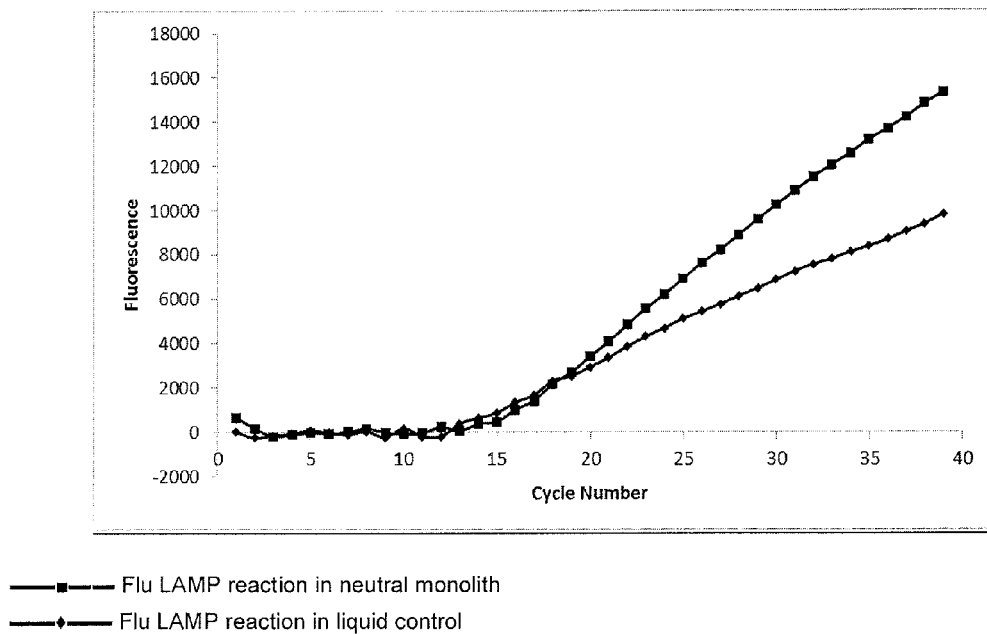

FIG. 7 shows a line graph comparison of LAMP DNA amplification in monolith and in a liquid control.

Figure 8:
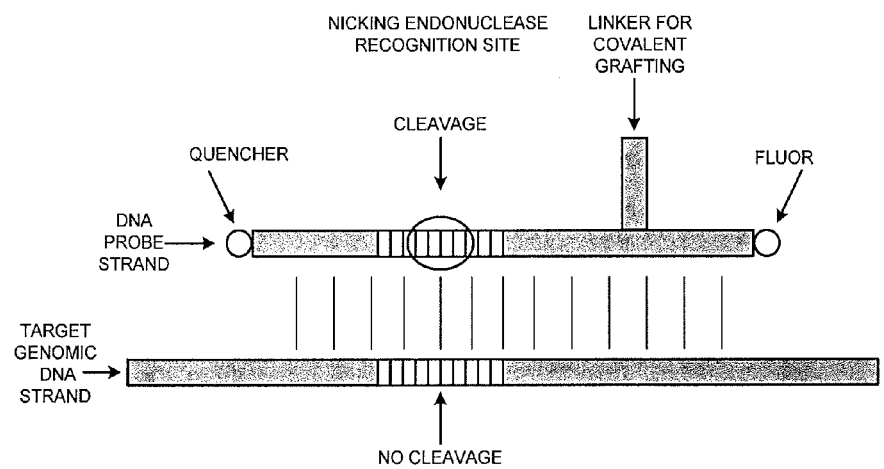

FIG. 8 shows a graphical illustration of the principle of a Nicking Endonuclease reaction.

Figure 9:
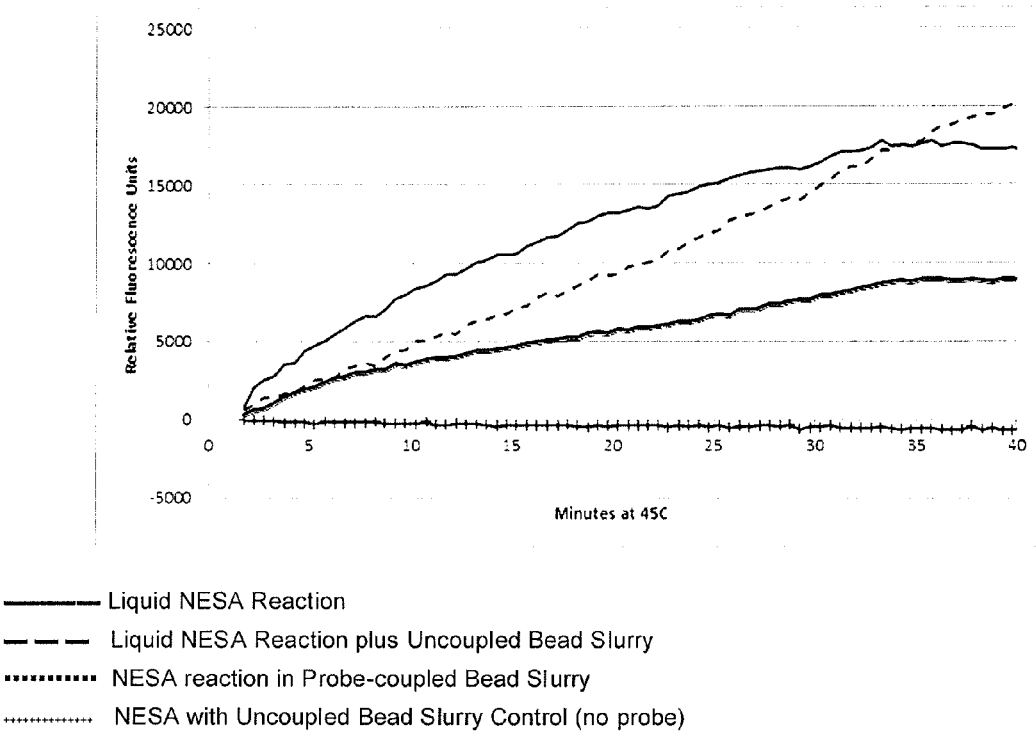

FIG. 9 shows a bar graph comparison of influenza NESA reactions in liquid, and in crushed monolith material slurries with and without probe coupled to the monolith pieces.

Figure 10:
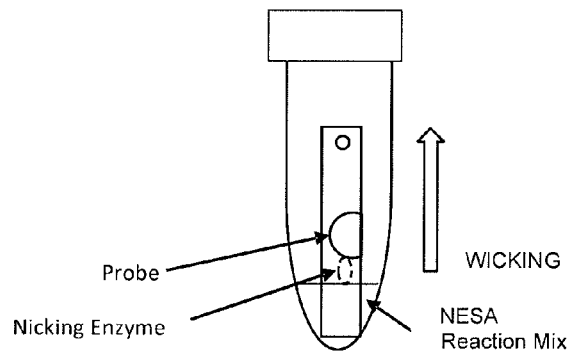

FIG. 10 illustrates shows a monolith standing on end in a sample holder.

Figure 11:
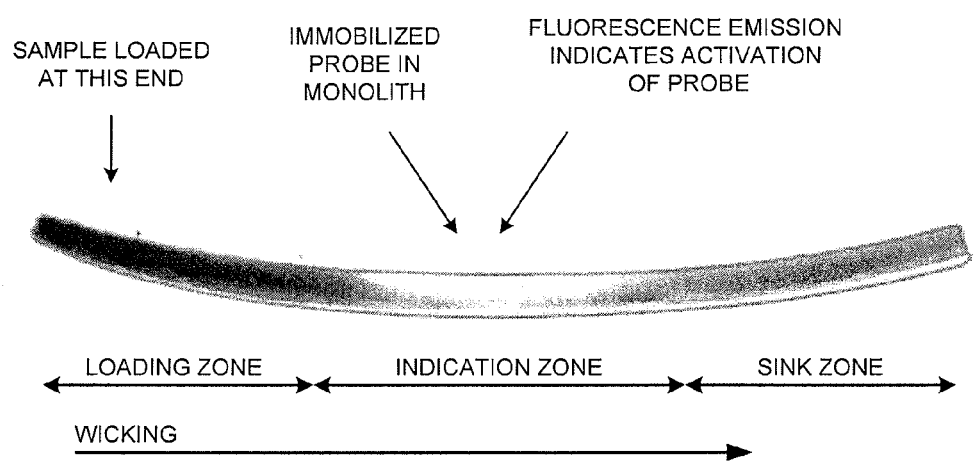

FIG. 11 is a photograph of a demonstration of a NESA reaction in a monolith.

Figure 12:
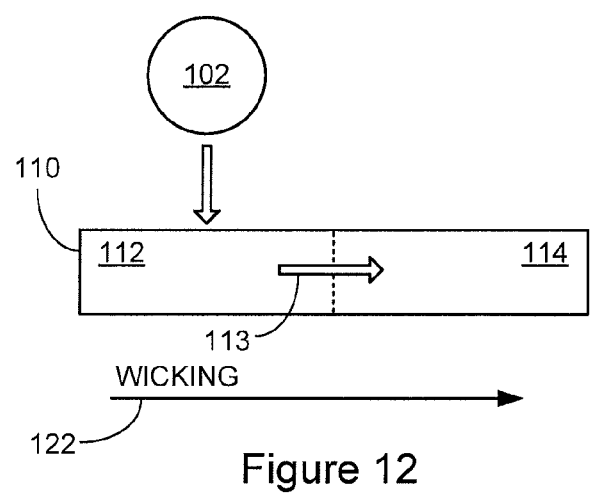

FIG. 12 shows a side view of a two zone monolith for processing a fluid sample.

Figure 13:
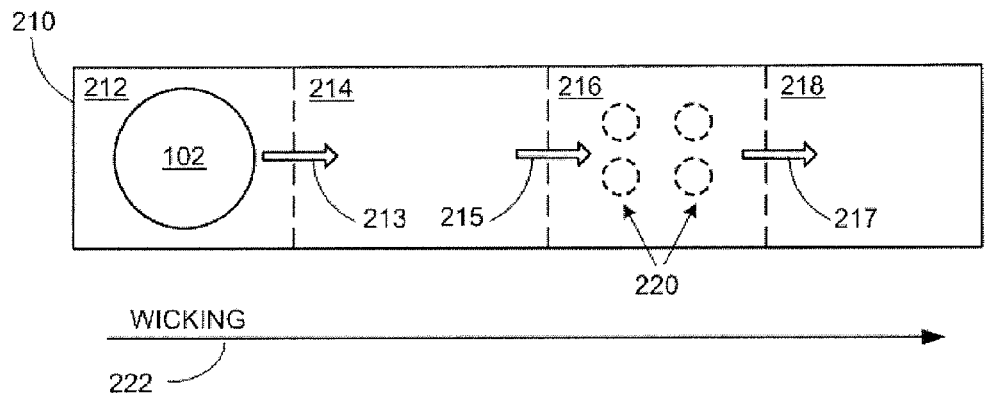

FIG. 13 shows a top view of a four zone monolith for processing a fluid sample.

Figure 14:
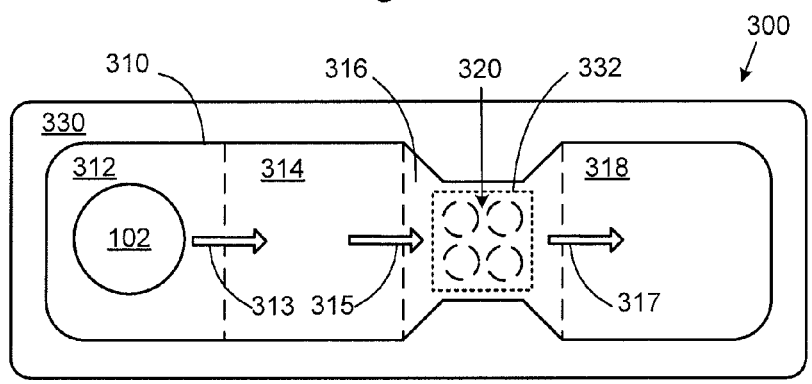

FIG. 14 shows a top view of a four zone reinforced monolith.

Figure 15:
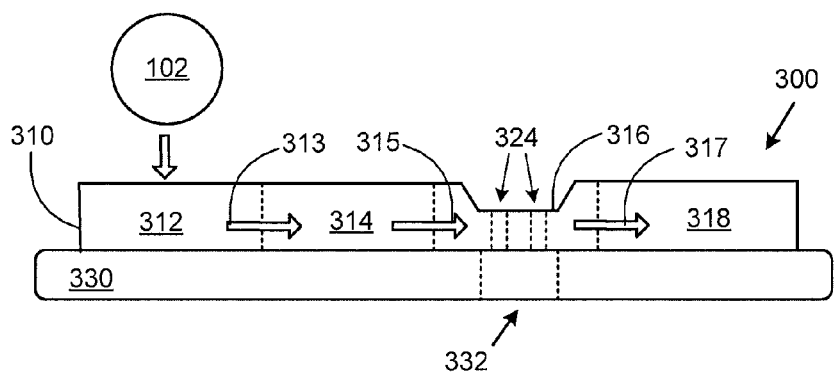

FIG. 15 shows a side view of the monolith of FIG. 14.

Figure 16:
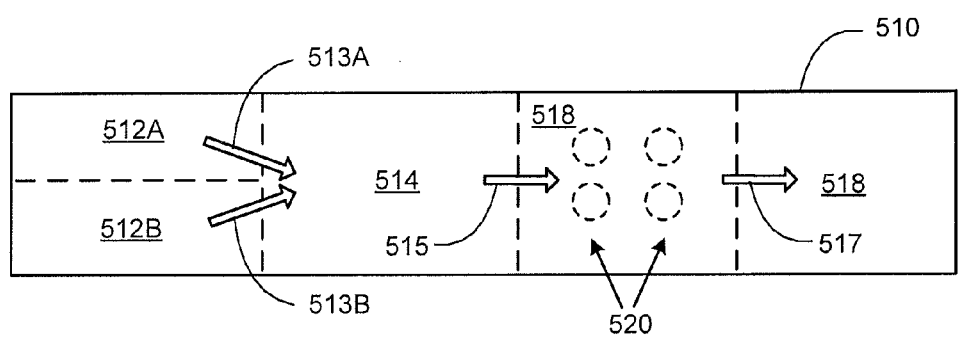

FIG. 16 shows a top view of a monolith with two parallel cleanup zones.

Figure 17:
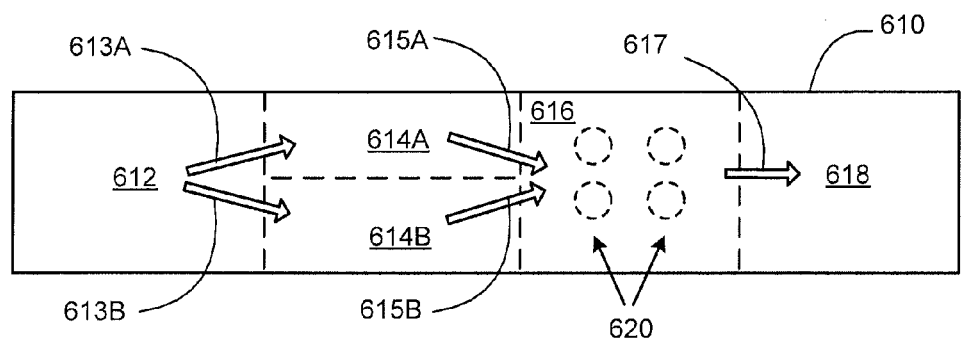

FIG. 17 shows a top view of a monolith with two parallel reaction zones.

Figure 18:
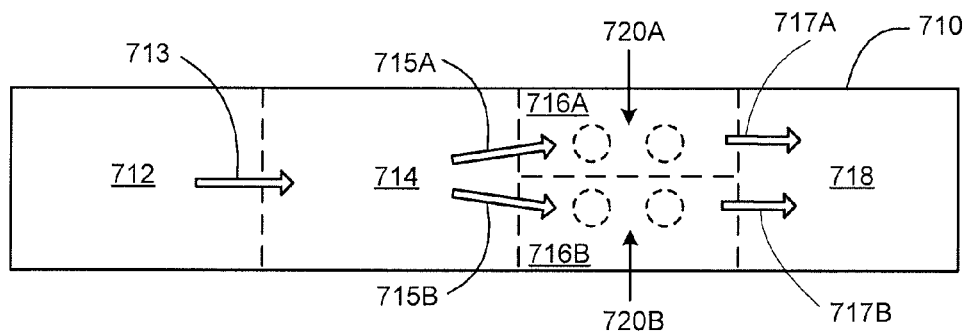

FIG. 18 shows a top view of a monolith with two parallel indication zones.

Figure 19:
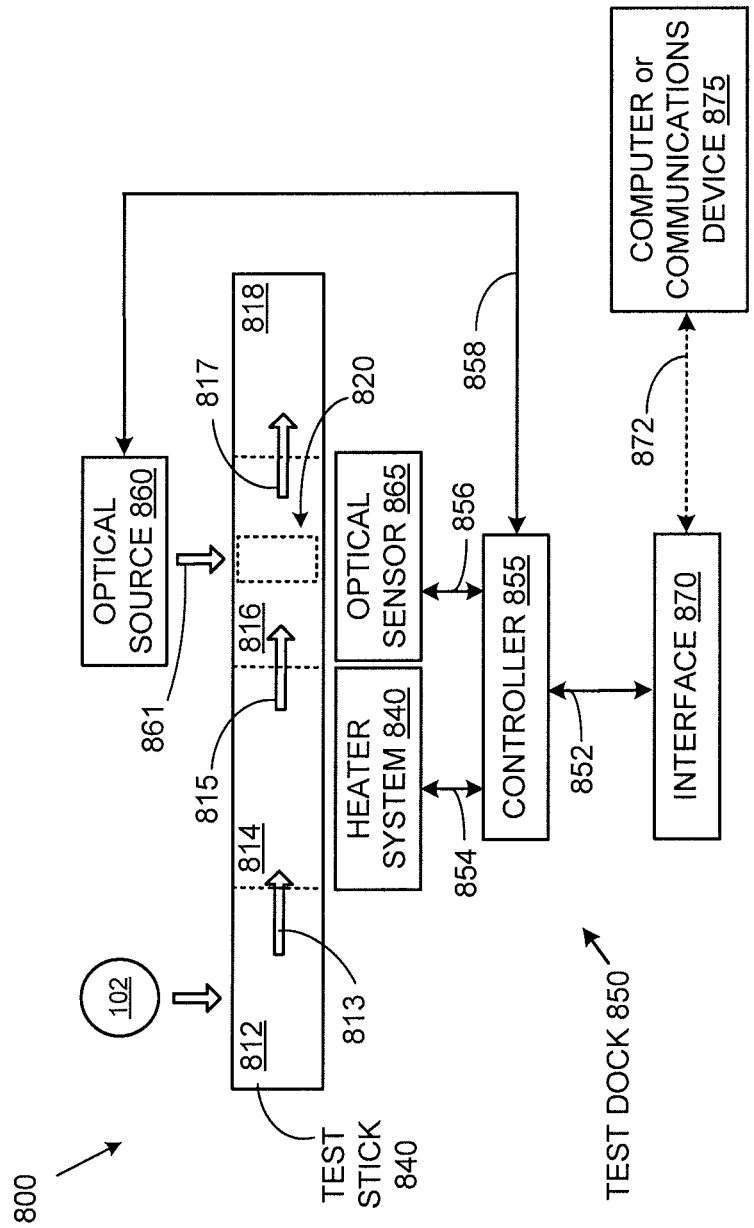

FIG. 19 shows a block diagram of an apparatus for molecular diagnostics.

Figure 20:
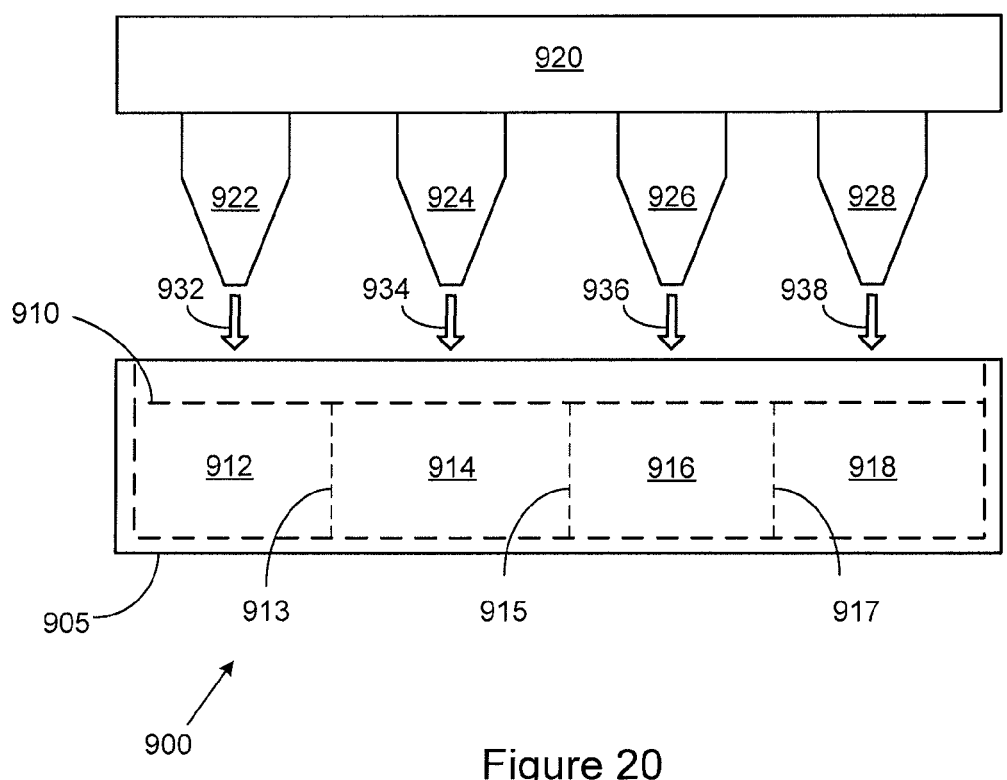

FIG. 20 shows a side view of an apparatus for the fabrication of a monolith.

FIG. 21 shows a method for fabricating a monolith using the apparatus of FIG. 20.

Figure 22:
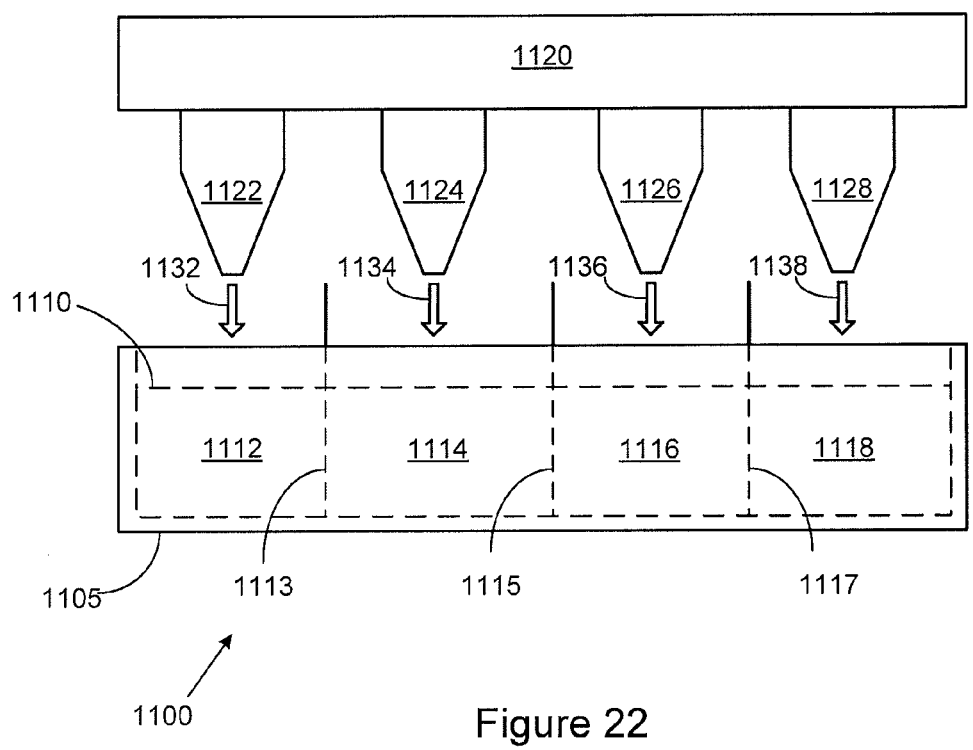

FIG. 22 shows a diagram of an alternate apparatus for the fabrication of a monolith.

FIG. 23 shows a method for fabricating a monolith using the apparatus of FIG. 22.

DEFINITIONS

Fluid Sample

Fluid samples as described herein may include an analyte of interest, may be suspected to include an analyte of interest, or may be presumed clear of the analyte of interest (it will be understood that in analytical methods, for example, molecular diagnostics, an assay or similar may be used to confirm an expected negative result).

The fluid sample may be a biological sample. The biological sample may be a bodily fluid obtained from a subject, for example, blood, saliva, urine, colostrum, milk, sputum, cerebrospinal fluid, amniotic fluid, plasma, semen, vaginal secretion, or serum. The sample may be suitably diluted as appropriate. The biological fluid may also be an extract of a biological sample obtained from a subject, for example, a tissue sample, a swab sample, or feces; or it may be a sample extracted from an insect, arachnid, parasite, crustacean, nematode, or similar.

The biological fluid may also be artificially cultured, for example, it may be a recombinant enzyme, a virus, fermentation medium, a vaccine, or similar.

The biological sample may be associated with a plant. For example, it may be a plant exudate or an extract of a plant.

The fluid sample may be obtained from swabbing or otherwise extracting material from surfaces, such as medical equipment, personal protective equipment, furniture, counters, or floors.

The fluid sample may be an environmental sample, for example, it may be a water sample or an extract of a solid of interest, for example, a soil extract, an ash extract, or similar. A water sample will be understood to include water sample a various stages in water purification processing, for example, the water sample may be raw sewage or processed sewage.

The fluid samples may be samples of interest for molecular diagnostics or analytics. The processing of the fluid sample may include a detection/analysis step to determine the presence or absence of an analyte of interest. Accordingly, monoliths as described herein may be suitable for facilitating detection of an analyte of interest in a fluid sample.

Self-Wicking

As used herein, the term refers to the effect of capillary action by the monolith pores on a liquid. This is the property of the monoliths that causes a liquid sample to flow spontaneously from a first portion of the monolith to another portion spaced from the first without the need for an external pressure differential to be applied (as is used, for example, in conventional column chromatography). It is this self-wicking ability that may alone provide motility to the fluid analyte sample during the diagnostic methods described herein.

The self-wicking is independent of the orientation of the monolith in space. It may occur vertically, for example up the monolith, or laterally, that is, along the monolith, depending on the method of application of the fluid.

Self-wicking, as described herein, refers to material exhibiting a wicking measurement of at least 1.8 cm in the following wicking test.

Of course, it will be appreciated that portions of self-wicking monoliths as described herein may have lower wicking rates, for example, a measurement of 1 cm in the following wicking test. These portions may be useful as flow restrictors, for example, to retain a fluid in a preceding portion of the self-wicking monolith, as described elsewhere herein.

As described herein, monoliths as described herein are suitably self-wicking.

Advantageously, this means that fluid flow through the monolith occurs without the need for externally applied pressure. Accordingly, self-wicking monoliths as described herein may be used in methods wherein the fluid flows with no externally applied pressure gradient across the monolith. In the self-wicking monoliths disclosed here, favourable interfacial energy between solvent and the monolith material causes the wicking action by pulling fluid into the material until all of the monolith has been wetted. The free energy of this interaction creates a hydrostatic pressure at the solvent front below ambient pressure. In other words, the back pressure of the fluid wicking through the monolith is less than ambient pressure at any elevation, and therefore less than mean sea level pressure. When the monolith is filled with fluid, wicking will stop, Wicking Test The test measures the distance water will travel up a monolith cured with dimensions: 1.27 cm wide, 6.35 cm long, 0.30 cm thickness. The monolith is prepared as described herein.

Prior to testing, the monolith was stored in atmospheric conditions (temperature: 18-22° C., RH 10-40%), although the inventors have found that no environmental control is required for monoliths that have not been loaded with environmentally-sensitive reagents (for example, through immobilisation/covalent grafting).

1. 3 mm of the monolith is submerged in de-ionised water with the monolith in the upright orientation;
2. The water moves up the length of the monolith due to wicking action;
3. The distance travelled by the water over the course of 2.0 min is measured at the corner of the monolith of the monolith having the greatest measurement.

The measurement may be made visually, simply by observing the solvent front.

A dye may be added to aid measurement. Suitably the dye is a dye that travels with the water without being significantly retarded by the monolith. Suitable examples include FD&C Yellow number 1 and fluorescein. Red 40 and Blue 1 may be also be used for some monoliths as described herein, although it will be appreciated that any dye may interact with particular functionalities in the matrix (for example, free amino groups) of certain monoliths as described herein, thereby causing retardation.

It will be appreciated that very large dyes, blue dextran for example, may be retarded by the pore size of the monoliths. Similarly, charged dyes may move along the monolith at different rates.

Suitably, self-wicking as used herein describes monoliths that would achieve a result of at least 1.8 cm in this test, preferably at least 2.0 cm, more preferably at least 2.3 cm, more preferably at least 2.5 cm, more preferably at least 2.7 cm, more preferably at least 3.0 cm, more preferably at least 3.2 cm, more preferably at least 3.5 cm.

It will be appreciated that for the diagnostic methods described herein, it may be preferable that wicking does not occur too quickly, for example, to permit suitable clean-up, amplification, and/or detection as appropriate. Accordingly, in some embodiments, self-wicking monoliths as described herein would achieve a result of less than 4.5 cm, for example less than 4.2 cm, for example less than 4.0 cm, for example less than 3.7 cm.

In some embodiments, self-wicking as used herein describes monoliths that would achieve a result of between 2.5 and 4.5 cm, for example, between 3.0 and 4.0 cm.

For example, the result may be between 2.7 and 4.2 cm, for example between 3.0 and 4.2 cm, for example between 3.2 and 4.2 cm, for example between 3.2 and 4.0 cm, for example between 3.4 and 4.0 cm.

For example, the result may be between 2.5 and 4.0 cm, for example between 2.5 and 3.7 cm, for example between 2.7 and 3.7 cm, for example between 3.0 and 3.7 cm, for example between 3.2 and 3.7 cm.

Wicking rate may also be measured in units of s/4 cm. A comparison table equating measurements according to the wicking test as described herein and a wicking value in s/4 cm is provided below (Table 1):

TABLE 1

| Wick Rate (cm) as measured in the wicking test described herein | Conversion to wicking rate in s/4 cm |
| --- | --- |
| 1.0 | 1920 |
| 2.0 | 480 |
| 3.0 | 213 |
| 4.0 | 120 |
| 5.0 | 77 |
| 6.0 | 53 |

Monolith

As used herein, the term monolith refers to a block composed primarily of a polymer matrix. This polymer matrix may also be referred to a continuous polymeric network, or a reticulated polymer. In other words, the polymeric matrix of the monolith is contiguous.

Suitably, the monoliths described herein are elongate, having an intended direction of flow (wicking direction) along the axis of the longest length (referred to herein as the length). The width and depth may be the same, or they may be different. Suitably, the width and depth are different. The length and width define at least one diagnostic surface. This diagnostic surface is suitably flat. In some embodiments, the monolith comprises at least two opposing parallel planar sides.

In some embodiments, the monolith may include one or more regions of reduced width; that is, the monolith may have one or more neck regions. This neck regions may separate more than one diagnostic surface. Neck regions may be formed through fabrication of the monolith in a mold of appropriate shape. Suitable monolith shapes are described herein.

Accordingly, the diagnostic surface may be rectangular in shape, or may be shaped so as to have one or more regions of reduced width, for example, dumbbell shaped.

The diagnostic surface is the surface from which detection occurs. However, the detection is not necessarily detection of analytes at or near the diagnostic surface. Monoliths as described herein may be at least partially translucent. This may permit detection of analytes within the body of the monolith, for example at a depth from the diagnostic surface selected from: up to 5.0 mm, up to 3.0 mm, up to 2.5 mm, up to 2.0 mm, up to 1.5 mm, up to 1.0 mm, up to 0.5 mm. This detection may be assisted by shining a light through the indication zone onto a photodiode array, CCD (charge-coupled device), or similar.

Accordingly, the diagnostic surface may be a surface of a monolith or portion of a monolith of any shape suitable for reading by a sensor or for visual interpretation, with or without the aid of back illumination (that is, illumination from the surface opposite the diagnostic surface).

A sample containing an analyte may be applied at one location along the diagnostic surface (at the sample application portion), with detection occurring after a time interval at a location spaced from the sample application portion (at the indication portion). Alternatively, the sample may be applied on an opposite face of the monolith to the diagnostic surface, (at the sample application portion), with detection occurring after a time interval at a location spaced from the sample application portion (at the indication portion) on the diagnostic surface. Alternatively, one end of the monolith (the ends being the faces of smallest surface area) may be submerged in a sample containing an analyte (the submerged surfaces of the monolith being the sample application portion); in this case the indication portion is spaced from the submerged end.

The distance between the sample application portion and the indication portion may be greater than 1 cm, for example greater than 1.3 cm, greater than 1.5 cm, greater than 1.7 cm, greater than 2 cm, greater than 2.2 cm, greater than 2.5 cm, greater than 3.0 cm, greater than 3.5 cm, greater than 4.0 cm, greater than 4.5 cm, greater than 5.0 cm, greater than 6.0 cm, greater than 7.0 cm, greater than 8.0 cm.

The present inventors have found that within these distances, sample processing and analyte amplification, for example, DNA amplification, protein digestion, cell or virus lysis, or heat treatment, can be achieved. These results are described herein.

The indication portion may be an indication zone having restricted flow compared to the portion of the monolith immediately preceding it in the flow direction. For example, the indication zone may be adjacent to a clean-up or amplification zone. Providing an indication zone having restricted flow as compared to zone immediately prior to it in the flow direction has two advantageous potential applications:
1). it may facilitate concentration of analytes flowing into the indication portion from the previous portion.
2). it may retard the flow of analytes out of the previous portion. Therefore, a clean-up or amplification zone may be rapidly filled with a sample which leaves this zone (to enter the indication zone having restricted flow) comparatively slowly, thereby prolonging "reaction time" in the previous portion.

Suitably, the length of the monolith may be 30 mm to 85 mm total fluid path length, for example, 30 mm to 50 mm total fluid path length Suitably, the width of the monolith may be from about 2 mm to about 25 mm, or even wider.

Suitably, the depth of the monolith may be 1 mm to 5 mm, this being a suitable thickness for UV curing to initiate polymerisation during the polymerisation step. Monoliths of greater depth may be fabricated using thermal curing procedures.

Carboxy monolith, as used herein, refers to a monolith having free carboxy (—COOH groups). These may be incorporated into the monolith during polymerization through selection of appropriate monomers, or they may be the product of post-polymerization treatment of the monolith to hydrolyse ester groups incorporated into the polymeric matrix. In some embodiments, the carboxy monolith is the product of a suitable post-polymerization hydrolysis step, for example, with a base, for example, a hydroxide base such as sodium hydroxide.

Intended Wicking Direction

As used herein, the term intended wicking direction refers to a primary direction of flow of fluid within a sample. Suitably, this is from a sample application portion to and beyond a sample detection portion, also referred to as an indication portion herein. The wicking direction can be ascertained by watching or otherwise observing movement of a fluid through the monolith in use.

Analyte

The term analyte, as used herein, refers to a species of interest for detection in a diagnostic and/or analytic method. For simplicity, references to analyte where appropriate throughout this specification may include pre-analyte(s). Pre-analyte refers to a component of a sample that itself undergoes a change to release or be transformed into the analyte that is detected. For example, cells may undergo lysis to release analyte proteins, lipids, and nucleic acids, including DNA and RNA. For example, species of interest may be modified with a fluorophore Hydrophilic Monomer The term hydrophilic monomer refers to a monomer with a polar side-chain capable of ionization or hydrogen bonding in an aqueous environment. Generally, polymers with high content of hydrophilic monomers are wettable or will absorb water. Examples of hydrophilic side chains include, without limitation, hydroxyl, amino, acetate, guanidate, amide, sulfate, nitrate, or nitrile.

Suitably, but not necessarily, the hydrophilic monomer includes a free hydroxyl group. For example, the hydrophilic monomer may be hydroxyacrylate, 2-hydroxyethyl methacrylate (HEMA), 2-hydroxyethyl acrylate, 2-hydroxypropyl methacrylate or 2-hydroxypropyl acrylate; or acrylic acid. In some preferred embodiments, it is 2-hydroxyethyl methacrylate (HEMA).

It will, of course be appreciated that a linker monomer may itself comprise free hydroxyl groups; that is, a linker monomer may be a hydrophilic monomer. For example, it may be 3-(acryloxy)-2-hydroxypropyl methacrylate or glycerol 1,3-diglycerolate diacrylate. These linker monomers comprising a free hydroxyl group may serve as a linker monomer and/or as a hydrophilic monomer in monoliths and methods as described herein.

Linker Monomer

Linker monomer, as used herein, refers to a polymerizable compound having at least two polymerizable groups spaced apart by a linker comprising at least one —C(R)$_2$O— group.

The two polymerizable groups suitably comprise vinylic moieties, and may for example be acryl or methacryl groups. Where the linker is joined to the two groups by —O—, the linker monomer may therefore be an acrylate or a methacrylate, for example, a diacrylate or dimethacrylate.

Each R may be hydrogen, or may be any organic group. Put another way, the linker may be an alkyl or substituted alkyl chain —(C(R)$_2$)$_n$— in which at least one, preferably at least two, —C(R)$_2$— groups are replaced by oxygen. The R groups may themselves include further polymerizable groups, and may be the same or different. In some embodiments, each R group is H.

Suitably, the linker is an ethylene glycol, for example, ethylene glycol, diethylene glycol, or polyethylene glycol. Alternatively, the linker may be a glycerol, for example glycerol 1-3-diglycerolate or 3-acryloyloxy-2-hydroxypropylmethacrylate.

Suitable linker monomers may include, without limitation:

TABLE 2

| | |
|---|---|
| Ethylene glycol dimethacrylate (EGDMA) | 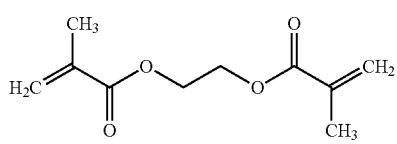 |
| Di(ethylene glycol) dimethacrylate | 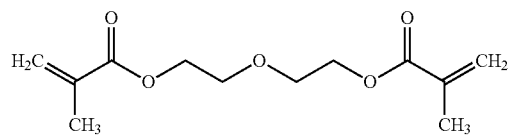 [SMILES: C=C(C)C(=O)OCCOCCOC(=O)C(=C)C] |
| Poly Ethylene glycol dimethacrylate (PEGDMA) | 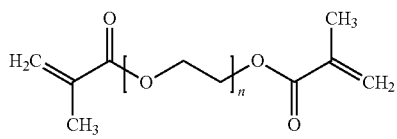 |

TABLE 2-continued

| | |
|---|---|
| Tetra(ethylene glycol) diacrylate (TEGDA) | |
| Tetra(ethylene glycol) dimethacrylate (TEGDMA) | |
| Pentaerythritol triacrylate | |
| 3-(Acryloyloxy)-2-hydroxypropyl methacrylate | |
| Trimethylolpropane trimethacrylate | |
| Bisphenol A glycerolate dimethacrylate | |
| Glycerol 1,3-diglycerolate diacrylate | |

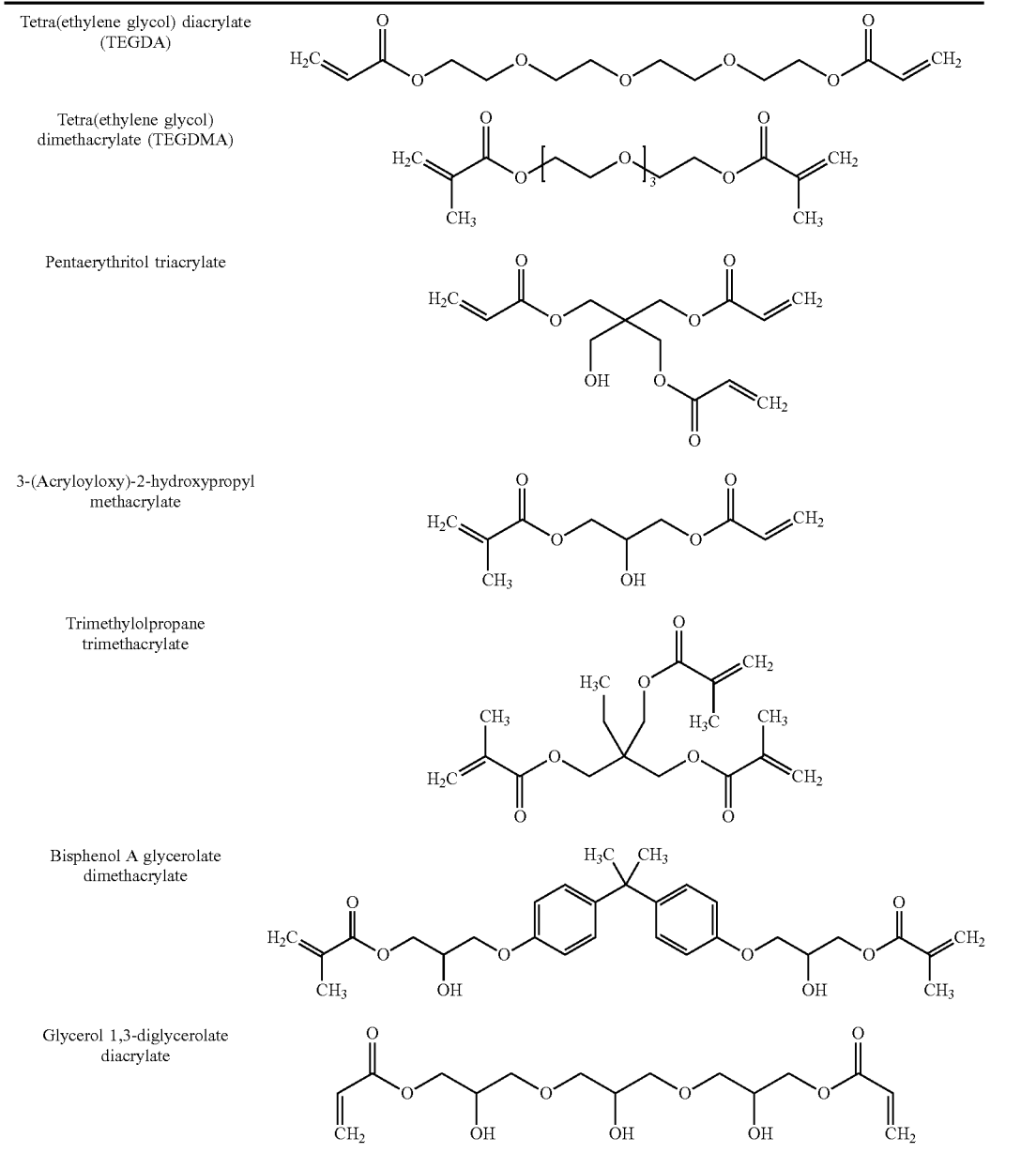

It will be appreciated that, unless where context dictates otherwise, references to a linker monomer include mixtures of two or more different such monomers. That is, a reference to a linker monomer may refer to single linker monomer as described above, or to a combination of two or more such linker monomers.

Porogenic Solvent

References to porogenic solvent, as used herein, include porogenic solvent systems; that is mixtures of two or more solvents. These mixtures may be homogeneous (that is, the solvents may be miscible) or they may be heterogeneous (that is, at least two of the solvents may be immiscible the mixture may be present as more than one phase). Of course, the porogenic solvent may be a single solvent. The porogenic solvent system may be provided containing one or more monomers, for example, it may be provided as a single solvent plus one or more monomers, the single solvent and monomer(s) being stable in combination (that is, not reactive with each other).

Porogenic solvents facilitate the formation of pores during the polymerisation process. Briefly, the polymerizable composition is provided with at least some, preferably all, of the monomers in solution. As polymerization occurs, the polymer chains that are formed begin to precipitate out of solution because although the porogen-monomer mixture is a good solvent for monomers, it is a poor solvent for the polymer. These precipitated polymer nuclei then become loci for the aggregation of remaining monomer, which is rapidly incorporated into the growing polymer network. As the nuclei grow, they collide and agglomerate to form a matrix of cross-linked globules with intersticial pores. This assembly mechanism produces a system of highly interconnected, open channels with a continuous network polymer spheroids forming the channel walls.

Suitably, a mixture of solvents is used. Suitable mixtures include alcohols (for example, octanol), mixtures of alcohols (for example, dodecanol or octanol and butanediol), and mixtures of alcohol and water (for example, methanol or ethanol and water or dodecanol or octanol and water). Suitable porogenic solvent systems include: n-octanol; a mixture of n-octanol and 1,4-butanediol; a mixture of n-octanol and 1,5-pentanediol; a mixture of n-octanol and n-propanol; a mixture of n-octanol and water; a mixture of methanol and water; and a mixture of one or more poloxamers and water.

Suitably, a surfactant may be used as a solvent, or included in the solvent system. For example, the present inventors have found that the inclusion of a surfactant adds some emulsion character to the polymermizable compositions. This in turn results in a larger scale pore system.

Examples of suitable surfactants include, without limitation, polysorbates, poloxamers, and the Triton-X™ surfactants, including Polysorbate 80. Polysorbate 20, Poloxamer 331, Poloxamer 181, Poloxamer 168, Triton X15 and Triton X-100.

As described elsewhere herein, the p resent inventors have found that, in some methods described herein, a surfactant may be used as the solvent. The Poloxamers described herein may be especially suitable for use as a solvent.

Initiator

Suitably, radical polymerisation is used to polymerize the polymerizable composition(s). Accordingly, a radical initiator may be included in the polymerizable composition. Suitable initiators may induce polymerisation chain reactions when thermally or photochemically induced. Suitable initiators are known in the art and include 2,2-dimethoxy-2-phenylacetophenone (DMPA or DMPAP), 2,2'-azobisisobutyronitrile (AIBN), benzoylperoxide (BPO), lauroyl peroxide (LPO), ammonium persulfate, and L-ascorbic acid. Preferably, the initiator in a polymerizable composition is 2,2-dimethoxy-2-phenylacetophenone.

The initiator is suitably present in relatively small amounts. For example, the amount of initiator in a polymerizable composition may be less than 3% total monomer (linker and non-linker including further monomers), preferably less than 2.5%, more preferably less than 2%, more preferably less than or equal to 1.5%. Suitably, the initiator concentration is sufficient to cause clouding of the polymerizable composition with 5 min of illumination and substantially complete polymerisation within 30 minutes under the irradiation conditions described herein.

Sample Application Portion

This is a surface portion of the monolith to which a sample containing an analyte is applied. This may be any portion of the monolith that is upstream from at least one other portion/zone of the monolith. It may be a well or a comb-shaped structure moulded, or machined into the monolith. This may be an area confined to the diagnostic surface of the monolith (that is, a face on which detection occurs) or may be the submerged face of an end of the monolith and the submerged parts of the four adjacent surfaces if the monolith is placed "end on" into a solution for use in its vertical configuration. In some embodiments, the sample application portion is a clean-up zone, or part of a clean-up zone, said zone being as described herein.

It may be preferable to use a carrier fluid, for example, a buffer, to assist passage of the sample through the monolith. Such a carrier fluid may be added to the monolith at the same point as the sample, or may be added upstream. Accordingly, in some embodiments, the sample application zone may be downstream from a carrier fluid introduction portion/zone.

Indication Portion

This is a portion of the monolith at which detection of an analyte occurs. Said sample indication portion may be an indication zone, or part of an indication zone, said zone being as described herein. The indication portion/zone may have a refractive index lower than that of nitrocellulose, 1.4, for example, and it may be thin enough to allow more than 1% of incident light, preferably more than 5%, preferably more than 10% to pass when transilluminated.

Procedures for Monolith Fabrication

General Procedures

The following non-limiting general procedures are provided.

Combine the monomers and solvent(s) in a suitable container with an initiator. Mix vigorously to combine the ingredients, until the appearance is homogeneous (either clear or opalescent in the case of immiscible components). This solution is a 'polymerizable composition'. Dispense an amount of the polymerizable composition into the desired mold then dislodge any bubbles, for example by gentle agitation or sonication.

Cure by irradiation with UV light (about 1 mW/cm$^2$) for 20 minutes. Optionally, wash the residual solvents out of the cured monolith with at least 3 portions of alcohol followed by at least 3 portions of water or other aqueous solution forced through the monolith by a pressure differential. Vacuum dry the monolith at 40-100° C. (for example, at 40-60° C.) until the weight no longer changes over time. Store under ambient conditions.

Procedures for Multi-Zone Monoliths

Multi-zone monoliths (a single monolith in which there are regions with different chemical or physical properties) may include zones that are different because of differences introduced during initial monolith formation (the polymerization step), or because of post-processing after the polymerization step is complete, for example, by covalent grating of further chemical moieties or by treatment of a portion of the monolith with a reagent to effect a change in the monolith chemistry in that portion.

Such zones may be introduced during the polymerization step using one of the following methods:

Method 1: Make a monolith of certain type as described in the general procedure above and elsewhere herein. Either stop before the washing, or fill dried monolith with solvent, and place the filled monolith in position in a mold. Follow the general procedure above to make the hybrid monolith where the further polymerization compositions are poured into the mold such that they are in direct contact with the already-cured piece of monolith. These compositions may be the same or different (as polymerization conditions may affect the polymerization product even if the same composition is used). Curing and subsequent steps are performed as described in the general procedure. In other words, the monolith may be created in "sections", and in each polymerization step interlinking between sections occurs through mechanical interdigitation of solid polymer structures and through polymerization between the nascent polymer of the new section and unreacted polymerizable groups in the section below. In this way, linear monoliths and branched monoliths may be fabricated. "Vertical" layers may also be included.

Method 2: Provide more than one polymerizable composition, these polymerizable compositions differing in at least one of the hydrophilic monomer and/or linker monomer identity, the total non-linker monomer to linker monomer ratio, the porogenic solvent (solvent identity, solvent ratios for mixed solvent systems), the concentration of hydrophilic monomer, linker monomer, and further monomer, if present, in the solution; the presence and identity of one or more further monomers, the presence and identity of an initiator. Dispense these polymerizable compositions into the mold at different locations, such that the monomer solutions flow to abut each other. When polymerization occurs these different locations have different properties.

It may be advantageous to provide dividers within the mold to define the different locations and prevent the different polymerizable compositions mixing during the filling of the mold, and possibly during initial polymerization. If such dividers are provided, these may be removed immediately prior to polymerization, or part way through polymerization. For example, the dividers may be removed 5-30 seconds after curing begins, 30-300 seconds after curing begins, 5-10 minutes after curing begins, 10-15 minutes after curing begins, or 15-20 minutes after curing begins. This permits initial polymerization to occur within the zones, without mixing of the different polymerizable compositions. Curing continues once the dividers are removed, with the nascent zones interlinking into a single polymeric network to form the multi-zoned monolith.

Method 3: Dispense a polymerizable composition into a mold, then selectively irradiate one or more locations within the mold such that polymerization is initiated only at said location(s). The remainder of the composition may be irradiated at a later point.

Monolith Molds and Shapes

Monolith polymerization occurs in a mold. Following polymerization, the monolith can optionally be dried, and optionally removed from the mold and optionally washed as described above. The drying, removing, and washing steps may occur in any order following polymerization.

For example, the monolith may be dried, removed, washed, and then dried.

For example, the monolith may be removed, washed, and then dried.

For example, the monolith may be washed, removed, and then dried.

For example, the monolith may be removed, dried, washed and then dried.

For example, the monolith may be washed, dried, and then removed.

Other permutations will be evident to one skilled in the art.

Suitably, the mold has internal dimensions to provide a monolith of the shape and size desired. For example, the mold may define a rectangular area as described here. Suitably, the monolith may have rounded ends, that is, the mold may define an area having two semicircular ends joined by straight sides.

For some applications, it may be preferable to provide one or more neck regions (these being regions of reduced cross-section in the direction of intended flow). Accordingly, suitable molds may be shaped so as to define an area of variable width.

Molds may be made of any suitable material, for example, metal, plastics, or elastomers. Molds may be lined with thin film plastics such as Saran™, LDPE, or with a silicone film.

For reasons of economy or ease of manufacture, in some cases polymerization may occur in a large mold (that is, a mold defining a surface area much larger than the desired diagnostic surface of the monolith), the sheet then being cut into individual monoliths for use. Sheets may be cut at any time, but for ease are preferably cut before drying.

In some embodiments described herein, the monolith is oblong in shape. That is, the monoliths may be of a single cross-section along the entire wicking length. Suitably, the length of an oblong monolith is between 1 cm and 10 cm, preferably between 6 and 8 cm, more preferably between 4 and 8 cm. Suitably, the width of an oblong monolith is between 2 mm and 25 mm, preferably between 6 mm and 20 mm, more preferably between 8 and 16 mm, more preferably between 10 mm and 14 mm; for example, the width may be around 12 mm. Suitably, the depth of an oblong monolith is between 1 mm and 10 mm, preferably between 1 mm and 7 mm, more preferably between 1 mm and 5 mm, more preferably around 2-3 mm.

Alternatively, the monolith may vary in cross-section along the wicking direction. In these embodiments, different zones of the monolith may have different cross-sections. Small cross-section areas may facilitate detection, for example, smaller depths may be preferable for visualisation of analytes during detection, especially when transillumination is used. Smaller cross-section areas may also slow the rate of flow of fluid from the preceding zone. This may act to keep fluid in said preceding zone, which may be useful for prolonging residence time for reactions (for example, cell lysis in a clean-up zone, RNA to DNA conversion in a reaction zone, analyte amplification in a reaction zone).

Figure 1:
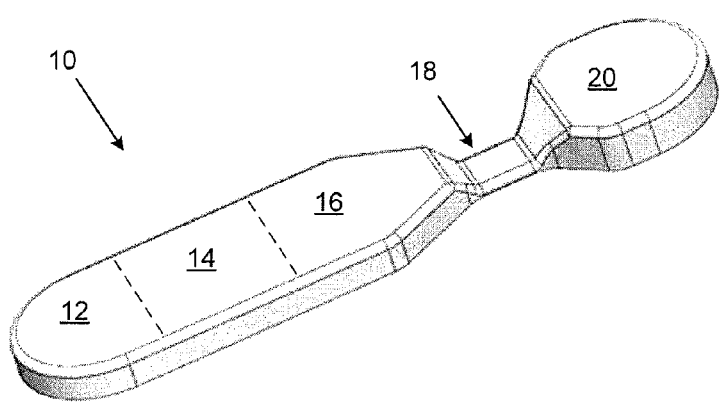
FIG. 1 shows a drawing of an embodiment of a monolith having a varying cross-section.

For example, the monolith may be a "dumbbell shape"; that is, the monolith may comprise a neck region having reduced cross-section located between two portions having greater cross-section, a non-limiting example of which is shown in FIG. 1. With reference to this figure, suitably the sample is applied to the monolith at the bottom left, on the top (diagnostic) surface. The fluid sample travels along the monolith through wicking along the wick direction. The wick direction is along the monolith diagonally from bottom left to top right of the image. In the first length of fixed cross-section, the sample may enter a clean-up zone as described and/or a reaction zone, for example, a reverse transcription or amplification zone as described. The sample then flows into a further zone location at the length of reduced cross-section (neck region). The reduced cross-section of this neck region may reduce the rate of fluid flow along the wick direction, thereby increasing the duration of the residence time of the fluid in the zone immediately preceding it. Suitably, the neck region is an indication zone as described. After the neck region, the cross-section of the monolith increases. Suitably, the monolith comprises a sink zone after the neck region.

Shrinkage

Some shrinkage may occur during polymerization washing and/or during drying. Suitably, the total shrinkage is less than about 10% of total surface area of the top face during curing, more preferably, less than about 5%.

However, in some instances, some shrinkage of monolith zones that partially encapsulate previously formed monolith structures, may be desirable. This moderate shrinkage serves to mechanically trap the pre-formed monolith structure within the newly formed monolith. Such entrapment creates an intimate, large area fluidic connection between the two zones which facilitates wicking from one zone into the other. Such entrapment can also serve to mechanically stabilize the joint between two zones. This moderate shrinkage may be up to about 10%, more preferably up to about 5%, more preferably up to about 3%. Tables 3 and 4 present data on several exemplary monoliths.

TABLE 3

| Ex. # | Applications/ Properties | Porosity (%) | % DMPAP Ini | % Func | Func ID | Hydrophilic Monomer HEMA | Linker Monomers EGDMA | TEGDMA | TEGDA |
|---|---|---|---|---|---|---|---|---|---|
| 1 | Rigid, high wicking | 75%* | 1 | NA | NA | 20.0% | 60.0% | 20.0% | |
| 2 | Rigid, high wicking, DNA binding | 75%* | 1 | 1.2% | TBAMA | 19.8% | 59.3% | 19.8% | |
| 3 | Rigid, high wicking, DNA binding | 71% | 1 | 1.5% | TBAMA | 19.7% | 59.1% | 19.7% | |
| 4 | Flexible, high wicking | 60% | 1.5 | NA | NA | 33.3% | 33.3% | | 33.3% |
| 5 | Bio-compatible | 70%* | 1 | NA | NA | 33.3% | 66.7% | | |
| 6 | Bio-compatible, reactive | 75%* | 1 | 2.0% | MAA | 32.7% | 65.4% | | |
| 7 | Flexible, high wicking | 60%* | 1.5 | NA | NA | 36.4% | 18.2% | | 45.5% |
| 8a | Bio-compatible, | 70%* | 1 | 1.0% | NHS | 19.8% | 59.4% | 19.8% | |
| 8b | reactive | | | 2.9% | | 19.4% | 58.3% | 19.4% | |
| 9 | Biocomaptible, lipophilic | 70%* | 1 | 1.0% | LyMA | 19.8% | 59.4% | 19.8% | |
| 10a | Bio-compatible, | 70%* | 1 | 1.0% | GlyMA | 19.8% | 59.4% | 19.8% | |
| 10b | reactive | | | 9.1% | | 18.2% | 54.5% | 18.2% | |
| 11a | Bio-compatible, | 70%* | 1 | 1.0% | SO4AA | 19.80% | 59.4% | 19.8% | |
| 11b | reactive | | | 2.9% | | 19.4% | 58.3% | 19.4% | |
| 12 | Flexible, DNA binding | 65%* | 1.5 | 1.5% | TBAMA | 33.3% | 33.3% | | 33.3% |

*Estimates based on percent Solids in Monolith

TABLE 4

| | Monomer Ratios | | Solvent Ratios | | | | Critical Physical Properties | | |
|---|---|---|---|---|---|---|---|---|---|
| Ex. # | LM/HM | LM/TM | Water | Pentane Octanol | Diol | Shrinkage | Wick Rate | Young's modulus (psi) | Ultimate strength (lb) |
| 1 | 4.00 | 4.00 | 1 | 19 | | −3.7% | 3.25 | 0.02 | 0.004 |
| 2 | 3.99 | 3.77 | 1 | 19 | | −4.3% | 3.20 | 0.04 | 0.009 |
| 3 | 4.00 | 3.72 | 1 | 19 | | −3.8% | 3.20 | 0.03 | 0.009 |
| 4 | 2.00 | 2.00 | | 1 | | −4.0% | 3.20 | 0.58 | 0.122 |
| 5 | 2.00 | 2.00 | | 2 | 1 | −5.2% | 2.95 | 0.15 | 0.036 |
| 6 | 2.00 | 1.88 | | 2 | 1 | −7.6% | 2.60 | 0.25 | 0.053 |
| 7 | 1.75 | 1.75 | | 1 | | −3.0% | 2.80 | 1.79 | 0.377 |
| 8a | 4.00 | 3.81 | | 1 | | −2.9% | 3.50 | 0.05 | 0.015 |
| 8b | 4.01 | 3.48 | | 1 | | −2.8% | 2.80 | 0.08 | 0.023 |
| 9 | 4.00 | 3.81 | 1 | 19 | | −3.4% | 1.80 | 0.36 | 0.075 |
| 10a | 4.00 | 3.81 | | 1 | | −2.5% | 3.48 | 0.03 | 0.010 |
| 10b | 3.99 | 2.66 | | 1 | | −2.7% | 2.45 | 0.05 | 0.015 |
| 11a | 4.00 | 3.81 | 1 | 19 | | −3.4% | 2.75 | 0.33 | 0.073 |
| 11b | 4.01 | 3.48 | | | | −3.4% | 2.95 | 0.32 | 0.094 |
| 12 | 2.00 | 1.91 | | 1 | | −4.1% | 2.60 | 1.63 | 0.101 |

LM/HM = Total linker monomer/hydrophilic monomer component volume ratio
LM/TM = Total linker monomer/total monomer component volume ratio (Hydrophilic plus Functional Monomer)

TBAMA—tertbutylaminoethylmethacrylate
MAA—mathacrylic acid
NHS—methacrylic acid and N-hydroxysuccinamide ester
LyMA—Lauryl methacrylate
GlyMA—Glycidyl methacrylate
$SO_4AA$—2-acrylmido-2-methyl-1-propanesulfonic acid Covalent Grafting of Chemical Moieties As described herein, it may be desirable to graft chemical moieties to the polymeric matrix of the monolith through a covalent reaction between reactive groups within the matrix and a suitably reactive group appended to the chemical moiety.

For example, a number of reactive groups react directly with carboxylic acid groups, and may be used to graft chemical moieties to the polymeric matrix. Carboxylic acid groups may be incorporated into the polymeric network through selection of appropriate monomers, or may be generated through hydrolysis of ester groups, for example, hydrolysis of acrylate and methacrylate groups, through treatment with a base such as sodium or potassium hydroxide.

Carboxy monolith refers to a monolith having free carboxy (—COOH) groups as described herein.

Example Hydrolysis Procedure

A 7.5 mg disc of a neutral polymeric matrix formulation (2:1 EGDMA:HEMA) was soaked in 1M or 6M NaOH for 1 hour at 95° C. The disc then washed by soaking in a 10 mL water bath for at least one hour. This soaking in water was repeated a further four times. The disc was then washed by soaking in 10 mL isopropyl alcohol for at least one hour. This soaking in isopropyl alcohol was repeated a further two times. Finally, the disc was dried overnight at 40° C. under vacuum.

Suitably, incorporated or hydrolysis-generated carboxylic acid groups are pre-activated to assist covalent grafting, for example, using known coupling reagents. Suitable coupling regents include, but are not limited to, 1-Ethyl-3-(3-dimethylaminopropyl)carbodiimide (EDAC or EDC), dicyclohexylcarbodiimide (DCC), diisopropylcarbodiimide (DIC), 1-hydroxy-benzotriazole (HOBt) and 1-hydroxy-7-aza-benzotriazole (HOAt).

Amino Monolith Generation

A number of reactive groups react directly with amino groups, and may be used to graft chemical moieties to the polymeric matrix. Accordingly, additionally or alternatively, free amino groups may be incorporated into the polymeric network through selection of appropriate monomers, or may be incorporated in protected form with the protecting groups then subsequently removed to unmask the free amino groups. Suitable nitrogen protecting groups are known in the art, for example tert-butyloxycarbonyl (t-Boc).

Grafting

Any suitable chemical moiety may be covalently grafted. Suitable examples may include dyes, proteins, enzymes or DNA/RNA derivatives, protein substrates, inhibitors and antibodies, as described herein. Suitable chemical moieties may include pH sensitive groups, including those derived from strong acid or bases; lipid-like molecules, and dendrimers, as described herein.

Accordingly, in some aspects, the present invention relates to monoliths comprising a covalently grafted compound, said covalently grafted being grafted to at least a portion of the polymeric matrix, wherein the covalently grafted compound may be selected from a dye, a protein, a protein substrate, an inhibitor, an antibody, a pH sensitive compound, a lipid-like molecule, or a dendrimer. In some embodiments, the monolith comprises a covalently grafted compound selected from an enzyme or a DNA/RNA derivative. In some embodiments, the monolith comprises a covalently grafted oligonucleotide probe, for example, a fluorescent quenched DNA probe. In some embodiments, the monolith comprises a covalently grafted enzyme, for example, a lysozyme, a defensin, a pore-forming toxin, a nicking enzyme, a restriction enzyme, a nuclease, a transcriptase, an antibody, or a protease. In some embodiments, the monolith comprises an impregnated enzyme, for example, a lysozyme, a defensin, a pore-forming toxin, a nicking enzyme, a restriction enzyme, a nuclease, a transcriptase, an antibody, or a protease. In some embodiments, the monolith comprises an impregnated oligonucleotide probe, for example, a fluorescent quenched DNA probe. In some embodiments, the monolith comprises a covalently grafted enzyme, for example, a lysozyme, a nicking enzyme, a transcriptase, or a protease. In some embodiments, the monolith comprises an impregnated enzyme, for example, a lysozyme, a nicking enzyme, a transcriptase, or a protease.

Covalent Grafting of FITC Dye to Amino Monolith Beads

To demonstrate the covalent grafting of suitable dyes to monoliths having free amino groups, fluorescein isothiocyanate (FITC) was covalently grafted to beads of polymeric matrix material.

Amino monolith material (1:3:1 TEGDMA:EGDMA: HEMA plus 5.0% 2-aminoethyl methacrylate (AMA)) was ground using a pellet pestle and mortar in 100 μL of 50 mM sodium borate pH 8.5. The ground material was diluted up to 1 mL with sodium borate buffer and centrifuged at 100×g for 1 minute. The supernatant containing beads broken free of the bulk monolith was aliquoted (850 μL to a new microtube and FITC was added to a final concentration of 20 ng/mL in a volume of 900 μL. and incubated for one hour in the dark. The beads were washed twice by mixing, centrifugation and re-suspension in PBS and finally resuspended in PBS. The final suspension was passed through a Beckton Dickinson 40 μM cell filter into a 5 mL round bottom tube.

For comparison purposes, the same process was repeated using beads formed of carboxy monolith material (1:2:1 TEGDMA:EGDMA:HEMA plus 2.0% methacrylic acid (MAA))

Measurements were taken in a Beckton Dickinson FACSCalibur flow cytometer. Channel settings were optimized using a neutral formulation to establish forward and side scatter values to be within the dynamic range of the instrument. Fluorescence was gain-adjusted to allow sufficient dynamic range for detection of strong fluorescence intensities. As shown in Table 5 FITC treatment of the DX3-carboxy negative control beads resulted in a primarily low fluorescence population (gate M1), whereas FITC treatment of the amino beads (1:3:1 TEGDMA:EGDMA:HEMA plus 5.0% AMA) resulted in nearly all beads being present on the high florescence gate (gate M2)

| Sample | Gate Counts | |
|---|---|---|
| | M1 Count | M2 Count |
| (1:2:1 TEGDMA:EGDMA:HEMA plus 2.0% MAA) (Carboxy neg. control) | 2600 | 2 |
| (1:3:1 TEGDMA:EGDMA:HEMA plus 5.0% AMA) (FITC-treated amino) | 8 | 4600 |

Table 5. Monolith beads separated into fluorescent populations using a user-defined fluorescence gating method. In this example, FITC treatment of the DX3-carboxy negative control beads resulted in a primarily low fluorescence population (gate M1), whereas FITC treatment of the (1:3:1 TEGDMA:EGDMA:HEMA plus 5.0% AMA) amino beads resulted in nearly all beads being present on the high florescence gate (gate M2).

Covalent Grafting of Fluorescein Cadaverine to Carboxy Monolith Solid

Fresh EDAC solid was dissolved at 16 mg/mL in water. 135 μL EDAC solution was mixed with 135 μL 200 mM MES at pH 7.0 and dispensed into wells of a 12 well plate. Pie-shaped disc pieces of carboxy polymeric matrix (1:2:1 TEGDMA:EGDMA:HEMA plus 2.0% MAA and 2:1 EGDMA:HEMA) were submerged in the EDAC/MES solution. 30 μL of 0.33 mg/mL Fluorescein-cadaverine (in DMSO) Molecular Probes dye were added per well. The pie-shaped disc pieces were incubated with shaking at RT for 0.5 hrs. The EDAC/MES/Fluorescein dye solution was removed and the slices were transferred to wells of a 96 well plate.

Figure 2:
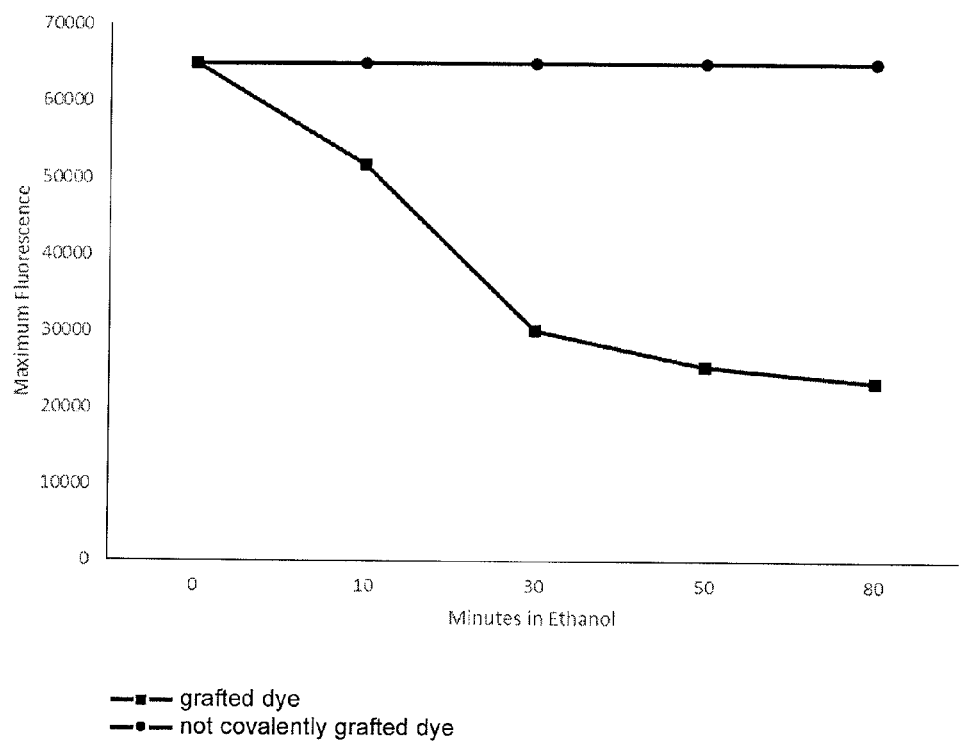
FIG. 2 shows a line graph comparing retention of grafted dye and not covalently grafted dye from the polymeric matrix with ethanol incubation.

Unbound dye was washed away with ethanol while fluorescence was monitored. A series of fluorescence x-y scans of the monolith pieces was collected over time. Well Scan readings were performed on a BMG Fluostar Optima Plate Reader. Filters used were 480 (excitation) and 530 (emission). The brightest pixel intensity over time of each well was plotted. As shown in FIG. 2 covalently grafted dye is retained (-■-), while dye not covalently grafted is eluted from the polymeric matrix with ethanol incubation (-■-). Similar results were obtained from tests of EDAC-mediated coupling of Fluorescein-cadaverine to carboxy-monolith material formed by 1M sodium hydroxide treatment of neutral monolith material 12:1 EGDMA:HEMA).

Covalent Grafting of Amino-Modified Oligonucleotide Probes to Polymeric Matrix

EDAC coupling solutions were made fresh before each use. Carboxy monolith formulations (e.g. 1:2:1 TEGDMA:EGDMA:HEMA plus 2.0% MAA) wick up approximately 2.5 µL of fluid per mg monolith matrix. A common format for testing employed 6 mg plugs, which wick up 15 µL of solution. Enough coupling mix to enable the complete saturation of the monolith was made using the following recipe:

160 mg/mL EDAC in was dissolved in water-free DMSO (10× stock). ½ volume of 200 mM MES buffer, pH 7.0, ¹⁄₁₀ volume fresh 160 mg/mL EDAC dissolved in dry DMSO, ¹⁄₁₀ volume of fluorescent quenched DNA probes (100 µM stock) were mixed. The solution was taken to final volume with deionized distilled water. Sufficient coupling mix was added to saturate carboxy monolith solid or beads. Reactions were incubated from 2 h to overnight at room temperature (in dark for fluorescent oligos). 5 µL of 30 mg/mL glycine, pH 7.0 solution per 70 µL EDAC solution was added. The reactions were incubated for at least 15 minutes at room temperature and then rinsed 3× in 200 µL water. For crushed monolith beads, light centrifugation was used to precipitate the beads. The supernatant was discarded. The samples were dried at 65° C. under vacuum for 1 h.

The above reaction was also be performed with ¹⁄₁₀ volume for Fluorescein-cadaverine (use 10 mg/mL) as a control for the covalent coupling reaction efficiency.

Changing the Grafting Density Using Linker Molecules

The grafting may be direct, as described above, or may be via a linker molecule. Branched linker molecules (also referred to as multi-arm) may be used to increase the density of grafted chemical moieties on the surface of the monolith.

Two such linker molecules are:

An 8 arm version has also been used in the experiment as described below.

Herein, the present inventors demonstrate, by way of illustration and not by way of limitation, the coupling level and stability of 6 combinations of dendrimer-arm to Fluorescein cadaverine-dye ratios via amino groups in the polymeric matrix.

Linker and Fluorescein cadaverine were initially incubated for 5 minutes at room temperature. This mixture was then mixed with EDAC, transferred to dry piece of amino polymeric matrix (1:2:1 TEGDMA:EGDMA:HEMA plus 2.5% AMA; a ⅛ pie-shaped piece of disc) and incubated for an additional 30 minutes before removing this reaction mixture and adding 300 µL water.

Ratios are Arms to Dye Probe, therefore lower ratios had more dye probe, and each 8-arm reaction had 4× more probe than the corresponding 2-arm reaction.

Figure 3:
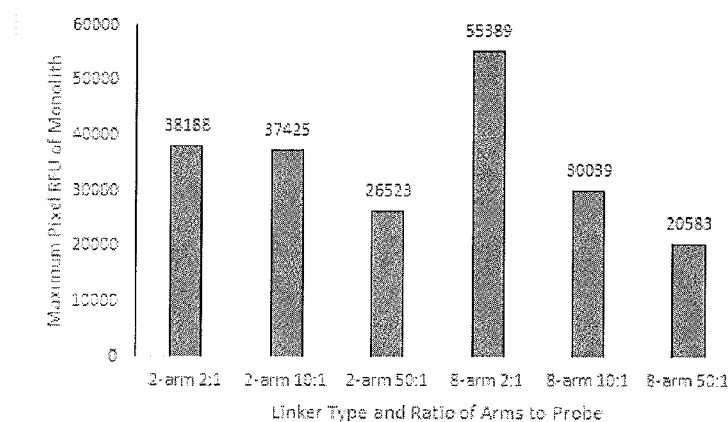
FIG. 3 shows a bar graph of peak fluorescence intensity from an x-y scan of a monolith piece after dendrimer-fluorescein coupling and washing, comparing linker type and ratio of arms to probe.

FIG. 3 shows the peak fluorescence intensity from an x-y scan of a monolith piece after dendrimer-fluorescein coupling and washing. For a given linker, the signal is greatest for lower Arms:Probe ratios (higher Probe:Arms ratios). Higher residual fluorescence after washing, indicating the greatest extent of probe coupling, was obtained for the 8-arm 2:1 than the 2-arm 2:1 mixture. The equivalence of peak fluorescence intensities for the two am 10:1 and 2:1 dye:linker ratios demonstrates saturation of available binding sites on the monolith surface. The higher value for the 8-arm 2:1 condition shows dye binding in excess of the intrinsic monolith capacity; with the excess dye coupling to the additional binding sites on the 8-arm linker.

Covalent Grafting of Enzymes

The present inventors have also demonstrated that functional enzymes may be covalently grafted to the polymeric matric of monoliths as described herein. The examples

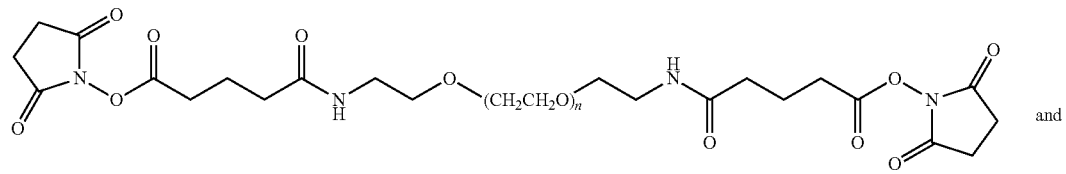

NHS-PEG-NHS (type D: GAS-Glutaramide Succinimidyl ester) (2-arm)

and

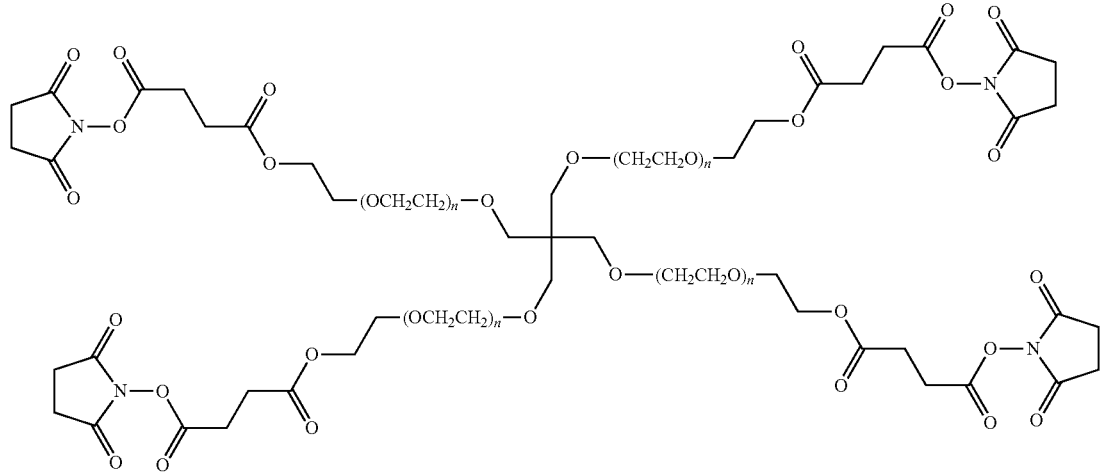

4-Arm PEG-NHS (type C NHS: SS-Succinimidyl Succinate ester)

describe use proteinase K and lysozyme, although it will be recognised that the procedures may be applied to other suitable molecules, including, but not limited to aptamers, ribozymes, other enzymes, antibodies, lectins and other proteins.

Enzymes are complex molecules having many amino groups that may participate in the covalent grafting reaction described herein. It might therefore be expected that covalent grafting would reduce or completely prevent enzyme activity. However, the present inventors have shown that, for the enzymes described, sufficient enzyme activity is maintained even after covalent grafting.

Immobilization of enzymes to carboxy monolith material (1:2:1 TEGDMA:EGDMA:HEMA plus 2.0% MAA) may use a carbodiimide coupling reaction. For example, enzyme solutions may be incubated with carboxy matrix in the presence of a fresh solution of EDAC in 50% dry DMSO and 50% 200 mM MES pH 7.0. Covalent coupling occurs between available amino groups in the enzyme proteins and carboxy groups in the polymeric matrix.

Proteinase K is a protease with broad specificity against a number of peptide bonds, specifically the peptide bonds adjacent to the carboxyl groups of aliphatic and aromatic amino acids. It is a very common enzyme used in the purification of nucleic acids from complex cell mixtures or tissues.

Lysozyme is a glycosidase that specifically breaks down the carbohydrate bonds in the cell wall of Gram negative bacteria, such as $E.\ coli$. It is a very common enzyme used in the purification of nucleic acids from Gram negative and, to a lesser extent, Gram positive bacteria.

Monolith Mediated Proteolysis with Covalently Grafted Proteinase K

The present inventors have shown that proteinase K immobilized by covalent grafting onto the polymeric network of monoliths described herein is capable of digesting lactalbumin, thereby showing that the enzyme's activity is retained despite the covalent grafting. Indeed, the observed activity is high, as described below.

160 mg/mL EDAC stock was dissolved in dry DMSO. 35 µL of this stock was added to 15 µL of 200 mM MES pH 7.0 and 20 µL 10 mg/mL Proteinase K in PBS. The solution was added to a 20 mg disc carboxy monolith polymeric matrix (1:2:1 TEGDMA:EGDMA:HEMA plus 2.0% MAA). The disc was incubated for 1 hr at room temperature. The reaction was then quenched with 5 µL of 30 mg/mL glycine, pH 7.0 for 15 minutes at room temperature. The disc was then washed 3× in 1×PBS and held in 1×PBS for 4 days at 4° C.

Alpha-lactalbumin substrate was dissolved at 10 mg/mL in 1×PBS. The proteinase K coupled disc was cut into equal 8 pie-shaped pieces. For each assay, one pie piece was placed point side down into a 0.5 mL microfuge tube. For each tube, 27 µL 10 mg/mL lactalbumin solution or 1×PBS, 3 µL 5 mM $CaSO_4$, was added. The tubes were closed and incubated at 65° C. for 2 hrs. An additional 50 µL deionized distilled water, was added, the tubes closed, and incubated at 65° C. for an additional 30 minutes.

Figure 4:
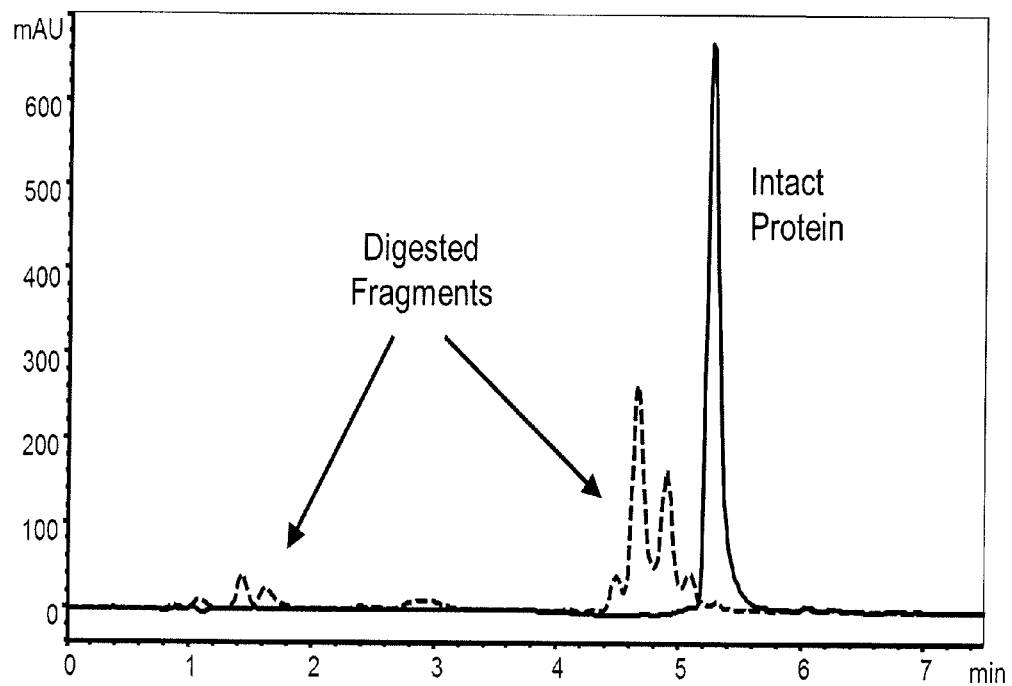
FIG. 4 shows a comparison of HPLC chromatograms demonstrating efficacy of proteinase K-coupled to a monolith of the invention. The substrate was alpha lactalbumin.

Untreated and proteinase K chip treated alpha-lactalbumin were analyzed by HPLC (FIG. 4. The figure shows sequential HPLC runs overlaid: Proteinase K Chip, plus alpha-lactalbumin (digested fragments), Proteinase K-free Chip, plus alpha-lactalbumin (intact alpha-lactalbumin).

The proteinase K treated alpha-lactalbumin was fully degraded from its original form in the short period of incubation tested, indicating that the enzyme's activity is maintained even though it is immobilized on the polymeric matrix.

Monolith Mediated Bacterial Cell Wall Degradation with Covalently Grafted Lysozyme The inventors have also shown that covalently grafted lysozyme retains glycoside hydrolase activity. This demonstrates that lysozyme may be immobilized on monoliths as described herein and used to facilitate purification and detection of bacterial DNA as described.

After covalently grafting lysozyme to a small block of carboxy monolith polymeric matrix, the sample was placed into a solution of fluorescently-labeled cell wall material (EnzChek® Lysozyme Assay Kit) and incubated for one hour at 37° C. in a plate reader, along with a lysozyme standard dilution series. The final fluorescence signal intensity developed in the substrate solution in the presence of the lysozyme chip is greater than the highest standard, indicating a strong presence of functional enzyme in the lysozyme conjugated matrix material (FIG. 5).

A fresh solution of 160 mg/mL EDAC stock in dry DMSO was prepared. A lysozyme mix was prepared from 20 µL of a 10 mg/mL solution of lysozyme in 1×PBS, 28 µL of a 200 mM MES solution at pH 7.0, and 15 µL water.

7 µL 160 mg/mL EDAC was spotted onto a single 20 mg disc formed from monolith material, (1:2:1 TEGDMA: EGDMA:HEMA plus 2.0% MAA). The prepared lysozyme mix (63 µL) was then added and the sample incubated at room temperature for 1 h. A glycine solution (10 µl; 30 mg/mL solution in 100 mM MES solution at pH 7.0) was then added and the sample incubated for 15 min at room temperature. The disc was then rinsed in water and stored at 4° C. until use.

To test the activity of the immobilized enzyme, a lysozyme-coupled disc and an untreated control disc were each cut into equal ⅛ size pie-shaped segments. Two pieces of each were then added to two wells of a microwell plate and lysozyme substrate was added. A dilution series of a lysozyme standard reagent was also run. Fluorescence was read at regular intervals to determine the extent of carbohydrate breakdown and consequent lysozyme activity.

Functions and Functionalization

Monoliths as described herein may be functionalized and may serve a variety of functions.

For example, monoliths as described herein may be functionalized:
  on the surface or throughout the structure;
  by adding at least one functionalized monomer during fabrication of the monolith, for example, selected from monomers with one of the following side chains: amino, carboxyl, PEG, alklyl, maleimide, succinimide, acyl halide, sulfhydryl and azide;
  by chemical hydrolysis;
  covalent grafting of compounds to the polymeric matrix of the monolith; and/or
  impregnation of one or more compounds within the polymeric matrix of the monolith.

For example, monoliths as described herein may be useful for any or all of the following, without limitation, in any order or combination:
  directing the flow of the fluid by physical design (direction can be used to mix reagents with the fluid);
  controlling the net rate of fluid flow (flux);
  mechanical entrapment of particulates, whole cells, cell ghosts, organelles, cellular debris, viral capsids, proteins, lipids, ribosomes, or molecular aggregates;

releasing molecules from the mixture, for example, via disruption of cells, spores, viruses, bacteria, yeast or fungi, molecular aggregates, etc.;

affinity binding of ions or molecules, for example, through electrostatic, Van der Waals or hydrogen bonding interactions or any combination thereof;

modifying fluid pH and osmolarity via release and/or adsorption of acids, bases, salts, sugars, osmolytes or excipients;

storing, preserving or controlling the release of reagents into the mixture;

releasing molecules of any class, including but not limited to enzymes or other proteins, lysozymes, defensins, nucleases, lipoproteins, detergents, surfactants, denaturants, proteases, kinases, ligases, polymerases, reverse transcriptases or ribonuclease inhibitors or any combination thereof retaining and localizing active molecules such as enzymes, detergents or probes that are suited to be localized in a specific zone and not others; and transmitting light or reflecting light to use as chemical indicators.

Accordingly, methods of fabrication as described herein may further comprise a step of functionalizing a monolith such that it is configured to perform any of the above functions.

Zoned Monoliths

In order to facilitate sample processing and analyte detection for some applications, it may be preferable to provide monoliths having zones having differing properties, oriented sequentially along the intended direction of fluid flow (wick direction) and/or located in parallel along the wick direction. Of course, it will be appreciated that the invention is not limited to multi-zone monoliths.

Zones may different in physical properties and/or chemical properties. The differences may be an integral feature of the polymeric matrix of the monolith (for example, introduced during a polymerisation step or through altering the polymeric network structure within the zone, through post-processing and/or covalently grafting additional chemical moieties to the matrix) or may be a result of impregnation of the monolith at that portion with a reagent or similar.

In use, a fluid sample is applied to the monolith at the sample application zone, and detected at a location spaced from the sample application zone. The point of detection of an analyte is in the indication portion of the monolith.

It will be understood that, while multi-zone monoliths contain zones having different properties, all of the zones of a multi-zone monolith are not necessarily different from every other zone, although they can be.

It will be appreciated that the combination of zones used, and the properties of those zones, may vary with intended fluid processing method. The following specific combinations are provided to illustrate, and are not intended to limit the invention. Other combinations and modifications will be readily apparent and are in the scope of this invention.

Clean-Up Zone

This zone may be configured to separate the analyte of interest from at least one other component of the sample and/or process the analyte prior to detection (and possibly prior to amplification). It may also add reagents to the sample, such as buffers, detergents, protease inhibitors or stabilizers. This processing may aid release of the analyte, for example through cell or virus lysis and/or acidification of sample pH.

For simplicity, references to analyte where appropriate throughout this specification may include pre-analyte(s).

Pre-analyte refers to a component of a sample that itself undergoes a change to release or be transformed into the analyte that is detected. For example, cells may undergo lysis to release analyte proteins, lipids, and nucleic acids, including DNA and RNA.

Separation of the analyte may occur through filtering; for example, by providing pores/channels in the zone of sufficient size to permit movement of the analyte with the fluid, but small enough to prevent movement of another component. This may be termed mechanical entrapment. For example, a virus (size approximately 0.1 µm) may be separated from erthyrocytes (size approximately 2 µm) through a filtering action in the clean-up zone. The virus may then travel with the wicking fluid to an indication zone, optionally via a further clean up zone and/or one or more amplification zones. For example, the virus may travel though a clean-up zone configured to facilitate viral capsid lysis and/or an amplification zone configured to facilitate reverse transcription and/or an amplification zone configured to amplify DNA.

The clean-up zone may remove unwanted contaminants through filtering action. Other sample "contaminants" that may be removed through such a filtering action include particulates, cellulose, fibers, silicates, whole cells, cell ghosts, organelles, cellular debris, viral capsids, lipid rafts and ribosomes.

Clean-up may also occur through affinity binding, for example through electrostatic, Van der Waals or hydrogen bonding interactions, or any combination thereof. Targeted affinity binding may be achieved through selection of suitable monomers or through treatment of the polymer network post-polymerization, for example, through treatment with hydroxide to hydrolyse ester moieties or by covalent grafting of chemical moieties as described herein.

Amino groups such as aminoethyl methacrylate can be used to capture species with negative charge such as lipid-membrane fragments, DNA, and proteins. Amino groups are chemically reactive; they can be used for permanently immobilizing other chemicals on the interior surfaces of the monolith after initial fabrication. This bonding may be direct, or it may be via added linkers (e.g. carbodiimide). Amino groups may also be used as the anchor for capture chemistry (for example, to immobilise molecules such as antibodies and/or lectins), and for immobilizing proteinases in the clean-up zone.

Negatively charged groups such as carboxy or sulfate can be used to capture species with positive charge such as proteins. Carboxyl groups are chemically reactive; they can be used for permanently immobilizing other chemicals on the interior surfaces of the monolith after initial fabrication. This bonding may be direct, or it may be via an added linker. Carboxyl groups may also be used in the clean-up zone to immobilize proteinase or detergent-like molecules for lysing cells.

Long chain alkyl groups, for example, incorporated through use of a monomer having such a chain during polymerization (for example, lauryl methacrylate, or amino-lauryl methacrylate, or sulfo-lauryl methacrylate), may be used to capture oils and fatty chain molecules, for example, detergents, triglycerides, lecithins, lipid-membrane fragments and lipoproteins.

Capture, as used herein, refers both to complete immobilisation and retardation during flow.

The clean-up zone may also facilitate release of analytes, for example, from a cell or similar (a pre-analyte). For example, the clean-up zone may facilitate one or more of:

polynucleotide release from a pre-analyte via disruption of somatic cells, viruses, bacteria, or fungi;

cytosol release through cell lysis;

Release of drugs bound to albumin through acidification;

Extraction of analytes from ground solids with surfactants.

These may be achieved through, for example, immobilised reagents (including enzymes), for example, through covalent grafting, or reagents impregnated into the polymeric matrix.

These reagents may include proteins, for example, enzymes, for example, lysozymes, proteases; defensins, lipoproteins, ribonuclease inhibitors; detergents, surfactants, denaturants, buffers, or any combination thereof.

The clean-up zone may also alter the properties of the fluid before it enters the next fluid processing zone. This may be achieved through absorption or release of acids, bases, salts, sugars, osmolytes or excipients. For example, the osmolyte may be glycerine.

Accordingly, in some embodiments the present invention may provide a monolith as described herein, or a method of making a monolith as described herein, wherein the monolith comprises a clean-up zone, said clean-up zone being configured to perform at least one of the following functions:

mechanical entrapment of a component in a sample to retard or prevent movement of the component through a monolith during wicking;

affinity entrapment of a component in a sample to retard or prevent movement of the component through a monolith during wicking;

facilitate one or more of polynucleotide release via disruption of somatic cells, viruses, bacteria, or fungi; cytosol release through cell lysis, facilitate release of analyte through disruption of masking effects in the sample matrix.

In some embodiments, two or more parallel clean up zones are provided.

Reaction Zones

The reaction zone is a zone in which desired chemical modifications to the analyte are executed. Examples include but are not limited to capture, hydrolysis, addition, conjugation, and amplification, the last of which is described in more detail below. These reactions may be facilitated by covalently grafted compounds and/or impregnated compounds as described herein.

Reaction steps may take longer than the time it would normally take for a sample to wick through the length of the zone. The reaction zone may therefore be configured to retard analytes in the zone such that they are within the reaction zone for sufficient time to undergo an reaction step. Such retardation may be a mechanical entrapment, or an affinity entrapment.

Alternatively, or additionally, the monolith may be constructed so as to restrict flow out of the reaction zone, for example, a neck region may be provided at the end of the reaction zone and/or at the start of the next zone. Alternatively or additionally, there may be provided downstream from the reaction zone a section of monolith with a low wick rate. Further information on monolith configurations is provided below.

Amplification

It may be desirable to amplify an analyte prior to detection. Amplify, as used herein, includes increasing the total analyte content, modifying the analyte so as to facilitate detection, for example through complexation with or grafting to a dye or similar, through triggering a chromophore-generating cascade reaction, or through other reaction or processing. Amplification may occur in a reaction zone (that is, a reaction zone may be an amplification zone).

As described above, amplification steps may take longer than the time it would normally take for a sample to wick through the length of the zone. The amplification zone may therefore be configured to retard analytes in the zone as described above.

The monolith may be compatible with enzymes, nucleoside triphosphates and nucleic acids in solution such that it does not substantially interfere with reactions involving them. It may also be suitable for, storing, preserving and/or controlling the release of: organic or inorganic chemicals, proteins, enzymes, natural or unnatural nucleotide sequences, DNA analogues, primers, target nucleotide sequences, probe nucleotide sequences, fluorescently-labelled nucleotide sequences, preserving reagents, stabilizing reagents or any combination thereof.

Accordingly, in some embodiments the present invention may provide a monolith as described herein, or a method of making a monolith as described herein, wherein the monolith comprises an amplification zone, said amplification zone being configured to perform at least one of the following functions:

providing compatibility with enzymes, nucleoside triphosphates and nucleic acids in solution;

introducing reagents into sample at one or more locations along the fluid path; mixing reagents with sample;

storing, preserving and/or controlling the release of: organic or inorganic chemicals, proteins, enzymes, natural or unnatural nucleotide sequences, DNA analogs, primers, target nucleotide sequences, probe nucleotide sequences, fluorescently labelled nucleotide sequences, preserving reagents, stabilizing reagents or any combination thereof;

modifying the analyte so as to facilitate detection, for example through complexation with or grafting to a probe, for example, a chromophore, fluorophore, colloidal gold, a magnetic bead, a quantum dot, or a latex bead.

Accordingly, in some aspects, the present invention relates to monoliths having a portion configured to facilitate amplification of a target nuclei acid sequence in a fluid sample, the monolith comprising at least one of the following components:

deoxynucleotide triphosphates (dNTPs)

inner primers, for example, FIP and BIP inner primers outer primers, for example F and B outer primers a polymerase, for example of Bst Warmstart 2.0 Polymerase (New England Biolabs)

buffer, stabilisers and/or salts loop primers

As described herein, each of these components may be independently covalently grafted to the polymeric matrix of the monolith or impregnated within the monolith as described herein.

In some embodiments, two or more parallel amplification zones are provided, for example, between a clean-up zone and an indication zone.

Indication Zone

Detection of an analyte occurs in an indication portion of the monolith. Suitably, this is a location on, or proximal to, the diagnostic surface of the monolith. This location may be in an indication zone.

The indication zone may be configured so as to facilitate detection of the analyte. This may be as a result of mechanical/physical properties of the monolith matrix, through modification of the matrix to incorporate certain chemical moieties, though suspension of a reagent or probe within the network or the printing (optionally grafting) of a reagent or probe onto the diagnostic surface. Suitably, the monolith is at least partially translucent, such that detection may be assisted through back illumination of the monolith.

The indication zone may include detection areas, for example, spots and/or stripes, which indicate the presence an analyte in the sample, for example by changing colour, phosphorescing etc.).

These detection areas may comprise a probe. Suitably, the probe may comprise a chromophore, fluorophore, or quencher. For example, the probe may comprise a xanthane derivative, for example, fluorescein, rhoda mine, Oregon green, eosin, and Texas red, or derivatives thereof, for example, Fluorescein-cadaverine.

Suitably, the detection areas formed in the monolith after fabrication. For example, detection areas may be are printed onto the surface of the monolith after fabrication. For example, the probe may be provided as a solution suitable for inkjet printing. In this manner, detection areas of suitable size and shape may be achieved.

Accordingly, in some embodiments the present invention may provide a monolith as described herein, or a method of making a monolith as described herein, wherein the monolith comprises an indication zone, said indication zone having one or more detection areas comprising a probe for detecting an analyte as described herein.

In some embodiments, the present invention may provide a method of making a monolith as described herein, the method further comprising the step of applying a solution comprising one or more probes to a diagnostic surface of a monolith to form one or more detection areas. The or each detection area may, for example, be independently a spot or a stripe (oriented laterally or medially). The step of applying the solution may be an ink jet printing step, or a pipetting step, or a rolling step, or may involve injecting the solution into the bulk material beneath the diagnostic surface.

In some embodiments, the analyte may be a target nucleic acid sequence in the sample.

In some embodiments, two or more parallel indications zone may be provided, for example, between a reaction zone and a sink zone.

Sink Zone

Suitably, monoliths as described herein undergo fluid and analyte transport as a result of self-wicking during use. As described herein, different wicking rates may be preferred along the direction of flow, for example, to aid clean-up, amplification, and/or detection. The provision of a sink zone, as described herein, towards the end of the monolith in the wick direction may be desirable to facilitate sample motility along the monolith during methods described herein.

The sink zone is configured to have a high wicking rate and/or fluid absorbance; in other words, it may act to draw the sample along the monolith. Therefore, suitably, the sink zone may have wicking rate greater than 3.0 cm in the wicking test described herein, preferably greater than 3.2 cm, more preferably greater than 3.5 cm, more preferably greater than 3.7 cm.

Additionally or alternatively, the sink zone may be greater overall capacity than one or more zones of the monolith preceding it in the wicking direction. This may be as a result of the sink zone having greater width and/or depth compared to said preceding zone.

Suitably, the sink zone is an absorber, and may be may be at least one of the following: a neutralizer, a deactivator, a decomposer or any combination thereof.

Accordingly, in some embodiments the present invention may provide a monolith as described herein, or a method of making a monolith as described herein, wherein the monolith comprises a sink zone. Suitably, the sink is located at the end of the monolith along the wicking direction; that is, the sink zone acts as a sink for fluid that has wicked from the fluid application portion of the monolith along the monolith.

Multi-Zone Configurations

As described herein, in some embodiments the present invention provides monoliths having two or more different zones. These zones may be arranged in order from the fluid application portion to the end of the monolith along the intended wicking direction of the monolith.

Preferably, the monolith has a sink zone located at an end of the monolith. In some preferred embodiments, the monolith always has a sink zone located in a region that is most distal to the sample application zone. For example, in a linear design, the sink and sample loading zones are at opposite ends of the monolith, whereas in a radial design in which a sample is loaded at the center, the sink(s) would be at the most peripheral region of the monolith.

More than one zone of any form or function may be included. These zones may be the same or different. For example, two different reaction zones may be provided. These may be sequential and different (Reaction Zone A and Reaction Zone B, for example) or may be spaced by, for example, a clean-up zone. In the latter case, the reaction zones may have the same or different properties.

Monoliths as described herein may be used for a wide variety of processes and methods. Accordingly, a variety of multi-zone monoliths may be provided using compositions, molds, impregnation, grafting, and other methods described herein and/or evident to one of skill in the art.

The following arrange ments are provided merely to illustrate the variety of multi-zone monoliths that may be provided. Of course, the following is not intended to limit the multi-zone monoliths of the invention:

Indication zone—Sink Zone
Reaction Zone—Sink Zone
Reaction Zone—Indication zone—Sink Zone
Reaction Zone A—Reaction Zone B—Indication zone—Sink Zone
Reaction Zone—Clean-up Zone—Reaction Zone—Indication zone—Sink Zone.
Clean-up Zone—Indication zone—Sink Zone
Clean-up Zone—Reaction Zone—Indication zone—Sink Zone
Clean-up Zone—Reaction Zone A—Reaction Zone B—Indication zone—Sink Zone
Clean-up Zone—Reaction Zone—Clean-up Zone—Reaction Zone—Indication zone—Sink Zone
Clean-up Zone—Clean-up Zone—Reaction Zone A—Reaction Zone B—Indication zone—Sink Zone A number of non-limiting exemplary multi-zone monoliths are shown in the figures.

For example, FIG. 6 shows an exemplary 4 zone monolith. The clean-up zone can be used selectively to trap particulate materials from the sample, such as contaminants or undesirable cell types. The reaction zone can assume a wide variety of functions, from reagent release, lysis, digestion, reverse transcription, nucleic acid amplification etc. (i.e. it may be a clean-up zone, an amplification zone, or a combination of the two as described herein). The indication zone may contain reagents which will identify the presence of analytes of interest, including control analytes. The sink zone (absorption zone) maintains fluid flow from the point of sample application through each subsequent zone until the analysis is complete. The zones are continuous and each may have multiple compatible chemistries as required by the application. As shown, the indication zone is located in a neck region of reduced cross-sectional area.

As described herein, it is possible to apply fluid samples containing infectious agents such as Flu virus particles to a monolithic matrix, and to lyse, reverse transcribe, amplify, and detect the specific amplification products in a continuous fashion using the self-wicking nature of the monolith to move fluid between zones of different function.

Fluid Junctions Between Monoliths

In some instances, it may be desirable to combine more than one monolith in a single device or enclosure. Each of these separate monoliths may contain one or more zones as described herein. Suitably, these separate monoliths may be placed in contact or fluid communication with each other such that fluid will move or wick from a specific wetted portion of one monolith into the other monolith. Suitably, the monoliths may be held in contact with each other by an external frame. Alternatively, the monoliths may be incorporated in a mechanical assembly that will bring them into contact with each other at some time after sample is applied. It will be understood that fluid transmission between these monoliths will be most effective if there is a sufficient level of physical contact in the junction between the monoliths. In one embodiment, the interfacial faces or abutting surfaces of the separate monoliths have substantially identical shapes or one or both of the monoliths is flexible enough to conform to the shape of the junction. It will also be understood that a portion of a different wicking material may be placed between two separate monoliths to establish a fluid junction between them.

Demonstration of Relevant Chemistries in Monoliths of the Present Invention

The following descriptions of specific chemistries are provided by way of illustration and not by way of limitation.

DNA Amplification

Monoliths as described herein may comprise one or more amplification zones. In some embodiments, an amplification zone is configured to amplify DNA. In some embodiments, an amplification zone is configured both to convert RNA into DNA and to amplify DNA. In some embodiments, two amplification zones are provided: a first configured to convert RNA into DNA and a second configured to amplify the nascent DNA.

Suitably, the DNA amplification occurs via an isothermal process, for example, Strand Displacement Amplification (SDA). For example, the DNA amplification may occur via Rolling Circle Amplification (RCA), Recombinase/Polymerase Amplification (RPA), Exponential amplification reaction (EXPAR), Helicase Dependant Amplification (HDA) or Loop-mediated AMPlification (LAMP).

Preferably, the DNA amplification may occur via Loop-mediated AMPlification (LAMP). Accordingly, in some aspects the present invention provides a self-wicking monolith for processing a fluid sample, the monolith comprising an amplification zone configured to perform loop-mediated amplification of DNA in the fluid sample. The present invention also provides methods of fabricating such monoliths.

LAMP is an isothermal amplification process that was developed by Notomi and Colleagues in 2000 (Notomi, T. et al. 2000, Nucleic Acids Research, 28, e63). The process uses a set of 4-6 primers per target, and can amplify target molecules into a mixture of hairpin-like and cauliflower-shaped structures containing multiple copies the original target sequence. LAMP normally operates at around 65° C. using a Bst Polymerase-like enzyme. When run in a real time PCR machine a constant temperature with a dye, it produces PCR-like amplification curves whose time-to-rise out of the baseline is inversely proportional to the log of the initial amount of starting template. When template molecules are more abundant, the fluorescence rises above a threshold value sooner.

The amplification zone configured to perform loop-mediated amplification may comprise at least one of the following components:
deoxynucleotide triphosphates (dNTPs)
inner primers, for example, FIP and BIP inner primers
outer primers, for example F and B outer primers
a polymerase, for example of Bst Warmstart 2.0 Polymerase (New England Biolabs)
buffer, stabilisers and/or salts
loop primers Any of these components, if present, may be impregnated into the polymeric matrix. This may be achieved through infusing the polymeric matrix, at the desired zone location, with one or more solutions of said component(s) and then allowing the solvent to evaporate (this may occur naturally or under elevated temperature and/or reduced pressure or by lyophization). The impregnated components may then dissolve into the wicking fluid as it passes though the zone, thereby mixing with the sample to undergo the LAMP reaction cascade.

Alternatively or additionally, a polymerase may be covalently grafted to the polymeric matrix using methods as described herein.

It will be appreciated that one or more components needed to facilitate the reaction may be included in the wicking fluid, for example, in a sample buffer, such that when the wicking fluid is in the reaction zone the reaction may occur.

The amplification zone configured to perform LAMP may further comprise a reverse transcriptase. Said reverse transcriptase may be impregnated into the matrix as described. Alternatively or additionally, it may be covalently grafted to the polymeric matrix using methods as described herein. It will be appreciated that, in methods described herein, a reverse transcriptase may be provided in the wicking fluid, for example, in a sample buffer.

It will be appreciated that additional sets of LAMP components may be impregnated together with corresponding template DNA sequences, RNA sequences, or virus particles to serve as reaction control samples. For example, a control reaction may be run in parallel alongside the analyte amplification.

Alternatively or additionally, the amplification zone configured to perform LAMP may be preceded by an amplification zone configured to convert RNA into cDNA (a reverse transcription zone), said zone configured to convert RNA into cDNA comprising a reverse transcriptase. The reverse transcriptase may be impregnated into the polymeric matrix.

Alternatively or additionally, it may be covalently grafted to polymeric matrix using methods as described herein.

Accordingly, in some aspects the present invention provides a method of fabricating a self-wicking monolith for processing a fluid sample, the method comprising forming an amplification zone configured to perform LAMP of DNA.

The step of forming the amplification zone configured to perform LAMP of DNA may comprise impregnation of one or more of deoxynucleotide triphosphates (dNTPs); inner primers, for example, FIP and BIP inner primers; outer primers, for example F and B outer primers; loop primers;

a polymerase, for example of Bst Warmstart 2.0 Polymerase; salts, stabilisers and/or buffers; and control template DNA and/or RNA and/or virus particles (of course, the test templates are supplied by the wicking fluid). For example, the impregnation may be impregnation of dNTPs, inner primers and outer primers, and optionally additionally loop primers.

Forming the amplification zone may further comprise impregnating the polymeric matrix with a polymerase and/or covalently grafting a polymerase to the polymeric matrix.

Forming the amplification zone may further comprise impregnating the polymeric matrix with a reverse transcriptase and/or covalently grafting a reverse transcriptase to the polymeric matrix. Alternatively, the method may further comprise a step of forming an amplification zone configured to convert RNA into cDNA (a reverse transcription zone) through impregnation of a reverse transcriptase and/or covalent grafting of a reverse transcriptase to the polymeric matrix.

For example, the method of fabricating a self-wicking monolith for processing a fluid sample may be a method comprising:
  providing a hydrophilic monomer and a linker monomer, the linker monomer having two polymerizable groups spaced apart by a linker comprising at least one —C(R)$_2$O— group;
  optionally wherein one or more further monomers are provided;
  obtaining a polymerizable composition by combining said hydrophilic monomer and linker monomer in a porogenic solvent
  polymerising the polymerizable composition to form the monolith;
  obtaining the monolith as a polymeric matrix free of unpolymerized starting materials;
  forming an amplification zone configured to perform LAMP of DNA though:
    impregnation of one or more of deoxynucleotide triphosphates (dNTPs); inner primers, for example, FIP and BIP inner primers; outer primers, for example F and B outer primers; loop primers; a polymerase, for example of Bst Warmstart 2.0 Polymerase; salts, stabilisers and/or buffers, and template DNA and/or RNA and/or virus particles into the polymeric matrix;
    impregnating the polymeric matrix with a polymerase and/or covalently grafting a polymerase to the polymeric matrix.

The method may further comprise a step impregnating the polymeric matrix with a reverse transcriptase and/or covalently grafting a reverse transcriptase to the polymeric matrix. Alternatively, the method may further comprise a step of forming an amplification zone configured to convert RNA into cDNA (a reverse transcription zone) through impregnation of a reverse transcriptase and/or covalent grafting of a reverse transcriptase to the polymeric matrix.

The impregnation may occur via applying the reagents to the monolith followed by natural evaporation, evaporation of the solvent under elevated temperature and/or reduced pressure, lyophilization or any other suitable method.

Also provided are self-wicking monoliths for processing a fluid sample, the monolith comprising an amplification zone configured to perform loop-mediated amplification of DNA in the fluid sample fabricated according to the methods described.

LAMP Isothermal Amplification Reaction

25 μL Isothermal LAMP reactions contained, 1.4 mM dNTPs, 1.6 μM FIP and BIP inner primers, 0.2 μM F and B outer primers, 0.4 μM loop primers, ≥16 units of Bst Warmstart 2.0 Polymerase (New England Biolabs), DNA template or virus particles, and 1× New England Biolabs® Isothermal Amplification buffer (20 mM Tris-HCl, 10 mM (NH$_4$)SO$_4$, 50 mM KCl, 2 mM MgSO$_4$, 0.1% Tween® 20, pH 8 at 20° C.) supplemented with 6 mM MgSO$_4$. For DNA product detection by dye-binding, 0.2 μL of a ⅙₀ dilution of 10,000×SYBR green gel stain dye in DMSO (Invitrogen™) was added to reactions as needed. Incubation temperature was at 65° C. for a time dependent on the known template or viral particle concentrations. Control experiments demonstrated that similar results were obtained using viral particles, viral RNA or cDNA or DNA, indicating that viral lysis and reverse transcription were accomplished under the same conditions as used for isothermal amplification only. Amplification specificity was verified by real time PCR.

Influenza virus was used to demonstrate LAMP amplification in self-wicking monoliths.

Influenza virus is a negative-strand segmented RNA virus. The US MedImmune vaccine for seasonal Flu for the 2012-2013 season was obtained. The 2012-2013 MedImmune vaccine is a trivalent vaccine containing live attenuated Influenza A/California/7/2009 (H1N1), A/Victoria/361/2011 (H3N2), and B/Wisconsin/1/2010 virus strains. Influenza A CA2009 LAMP primers published in patents by Panda et al. were used (EP2499264 A1, US20120231445, WO2011058580A1). Using these LAMP primers designed against the Hemagglutinin gene of strain A/California/7/2009, the inventors were able to perform the LAMP reaction on diluted liquid vaccine both in solution and in the monolith. 1E7 was used as the average of the published particles/mL (1E6.5 to 1E7.5) to calculate the number of virus particles/RNA copies used in LAMP reactions.

It will be appreciated that for amplification of nucleic acid sequences from a virus, viral lysis must occur prior to amplification of viral nucleic acid. This may be accomplished in the amplification zone through use of high temperature, or by other methods, for example in a preceding cleanup zone of the monolith as described herein.

For amplification of RNA, suitably reverse transcription of viral RNA to viral complementary DNA (cDNA) (reverse transcription) is performed. This may be in an amplification zone that is configured to convert RNA into DNA, said amplification zone preceding the amplification zone that is configured to perform DNA amplification, or reverse transcription and DNA amplification may occur in the same zone.

Liquid reaction mixtures were wicked into dry monolith, incubated at 65° C., inactivated at 95° C., and the monolith samples were soaked in buffer to elute the reaction products. The amplification products were quantitated by real time PCR (FIG. 7). Liquid (control) reaction was diluted to the same extent as liquid eluted from monolith before real time PCR. After a 50 minute isothermal LAMP amplification reaction, the real time PCR amplification curves from eluted and liquid control LAMP reactions rose from the baseline at the same time, demonstrating an equivalent level of amplification in liquid and in monolith.

DNA Detection

Monoliths as described herein may be configured to facilitate detection of DNA, for example through nucleic acid hybridization and signaling of the DNA.

Accordingly, in some aspects the present invention provides a method of fabricating a self-wicking monolith for processing a fluid sample, the method comprising forming an indication zone configured to facilitate detection of DNA. For example, the method may be a method of fabricating a self-wicking monolith for processing a fluid sample, the method comprising forming an indication zone configured to perform nucleic acid hybridization and signaling of DNA.

For example, and not by way of limitation, the nucleic acid hybridization and signaling may be a nicking endonuclease (NESA) hybridization and signaling process. An indication zone configured to perform NESA hybridization and signaling comprises a DNA probe. Suitably, the DNA probe comprises a fluorophore and a quencher joined by a nucleic acid chain, for example, a short single strand of DNA. Suitable probes are known in the art. Suitably, the indication zone configured to perform NESA hybridization and signaling also comprises a nicking enzyme, for example, a nicking endonuc lease. Accordingly, in some aspects the present invention relates to monoliths comprising a nicking enzyme; the nicking enzyme may be covalently grafted to and/or impregnated into the polymeric network of the monolith.

Suitably, the probe is suitable for detecting a target sequence. NESA hybridization and signaling processes are described in detail in US patent application US2012/00655088. In brief, the fluorophore of the probe in quenched by its proximity to the quencher. When the probe encounters the target sequence the nucleic acid sequence of the DNA probe hybridizes with the target sequence to form a section of double stranded DNA comprising the DNA probe. As double stranded DNA, the nucleic acid sequence of the DNA probe may be cut by the nicking enzyme, thereby releasing the quencher from the fluorophore such that fluorescence can be detected. By design, the nicking endonuclease may cleave the nucleic acid chain of the DNA probe and not the target DNA (as shown in FIG. 8). Suitably, light is used to visualise the fluorophore. The wavelength of the light may be selected to suit. The light may, for example, be UV light.

FIG. 8 shows the principle of a Nicking Endonuclease reaction. When the single stranded DNA probe hybridizes with its DNA match, the nicking endonuclease cuts the probe strand, separating the Fluor from the Quencher. Because both sides of the probe flanking the nick are shorter, they will tend to dissociate from the target, resulting in florescence. The target DNA is then free to bind to new uncut probes and continue the cycle, generating fluorescence. If the DNA probe is covalently grafted to the monolith, the fluorescence will be at the site of immobilization.

The DNA probe may be impregnated into the polymeric matrix and/or the probe may be covalently grafted to the polymeric matrix via an oligonucleotide linker u sing methods as described herein. The step of forming the indication zone configured to perform NESA hybridization and signaling of DNA may comprise impregnation of one or more DNA probes into the polymeric matrix and/or covalent grafting of one or more probes onto the polymeric matrix as described herein. Preferably, the DNA probe is covalently grafted. This prevents migration of the fluorophore within the monolith which weakens signal. Furthermore, for detection of more than one analyte, suitably appropriate DNA probes may be covalently grafted at different points within the indication zone(s) such that each analyte may be independently visualized. For example, the monolith may comprise two DNA probes covalently grafted to the polymeric matrix at different points along the wicking direction of the monolith.

The nicking enzyme may be impregnated into the polymeric matrix and/or the nicking enzyme may be covalently grafted to the polymeric matrix using methods as described herein. The step of forming the indication zone configured to perform NESA hybridization and signaling of DNA may comprise impregnation of one or more nicking enzyme into the polymeric matrix and/or covalent grafting of one or more nicking enzyme onto the polymeric matrix as described herein.

For example, the method of fabricating a self-wicking monolith for processing a fluid sample may be a method comprising:

providing a hydrophilic monomer and a linker monomer, the linker monomer having two polymerizable groups spaced apart by a linker comprising at least one —C(R)$_2$O— group;

optionally wherein one or more further monomers are provided;

obtaining a polymerizable composition by combining said hydrophilic monomer and linker monomer in a porogenic solvent polymerising the polymerizable composition to form the monolith;

obtaining the monolith as a polymeric matrix free of unpolymerized starting materials;

forming an indication zone configured to perform NESA and signaling of DNA though:

impregnating the polymeric matrix with a DNA probe and/or covalently grafting a DNA probe to the monolith;

impregnating the polymeric matrix with a nicking enzyme and/or covalently grafting a nicking enzyme to the polymeric matrix.

Preferably, the step of forming an indication zone configured to perform NESA and signaling of DNA comprises covalently grafting a DNA probe to the polymeric matrix.

Suitably, the nicking enzyme is a nicking endonuclease.

Optionally, more than one DNA probe may be present.

Also provided are self-wicking monoliths for processing a fluid sample, the monolith comprising an indication zone configured to perform NESA hybridization and signaling of DNA in the fluid sample fabricated according to the methods described.

NESA Reactions of Coupled DNA Probes

To test the ability of coupled probes to undergo NESA reaction and signaling, pieces of monolith material bearing covalently grafted probes were placed in a NESA reaction solution and compared to results in solution only (control). The results are shown in FIG. 9. Both control reactions and reactions of monolith plugs covalently grafted to NESA probes emit fluorescence, indicating that the system is functional both in solution and with probe grafted to a monolith.

To demonstrate NESA in a wicking reaction, a spot of aminated NESA probe was immobilized in an indication zone in carboxy monolith using carbodiimide chemistry. A small 2 µL spot of nicking endonuclease was impregnated into the monolith just upstream of the coupled probe just before the start of the wicking. The NESA reaction mixture containing buffer and DNA template was added to a 50 mL conical tube. The reaction mixture was applied to the monolith by standing the monolith on end with the sample application portion in the reaction mixture. (FIG. 10) The monolith was incubated at 48° C. in this position for 1 h. The monolith was cut in half (FIG. 11, photograph.) and visualized from the side in a UV visualization box. The detection region is fluorescing due to the immobilized NESA reaction product.

The fluorescence signal results from the following chain of events within the monolith:

a) hybridization of the probe and target sequences, b) recognition of and complexation with the target duplex sequence by the nicking endonuclease, c) enzymatic cleavage of one strand in the target duplex by the nicking endonuclease, d) dissociation of the components of the complex, including the fluorescence quencher and e) fluorescence emission of the probe from the now un-quenched fluorescent end (the immobilized end).

A Detailed Discussion of FIGS. 12 to 23

FIG. 12 shows a side view of one embodiment of a two zone monolith 110 for processing a fluid sample 102. Fluid sample 102 sample or an environmental sample with or without carrier fluid. Monolith 110 includes a first zone 112 and sink zone 114. Chemicals and reagents in first zone 112 process fluid sample 102 and the resultant mixture 113 flows or wicks into sink zone 114.

In some embodiments, monolith 110 can have more than two zones for the processing of fluid samples. For example, a three zone monolith similar to monolith 110 shown in FIG. 12 could include a clean-up zone, a reaction zone configured as an amplification zone and a sink zone.

FIG. 13 is an overhead view of an embodiment of monolith 210 which can be used to process fluid samples and includes clean-up zone 212, reaction zone 214, indication zone 216 with indication spots 220 and sink zone 218. Monolith 220 can be configured as a test stick for a molecular diagnostic device, for testing for an analyte, such as a target nucleic acid sequence in fluid sample 102 and such a monolith would have a reaction zone 214 configured as an amplification zone. Fluid mixture 102 is loaded into monolith 210 at clean-up zone 212. The chemicals and reagents in clean-up zone 212 process mixture 102 and the resultant mixture 213 flows or wicks into reaction zone 214. The chemicals and reagents in reaction zone 214 can perform various functions, such as to amplify a predetermined target nucleic acid sequences in mixture 213 and the resultant mixture 215 flows or wicks to indication zone 216. The chemicals and reagents in indication zone 216 process mixture 15 and the resultant mixture 217 flows or wicks to sink zone 218.

When the fluid mixture 215 is processed in indication zone 216, the reagents in indication zone 216 may react with mixture 215 and generate a result that can be read by an optical sensor with the application of light, either by reflection or transillumination. If the target nucleic acid sequence is in mixture 215, then there will be a change in either the wavelength and/or intensity of the light transmitted through indication spots 220 in indication zone 216. Mixture 217 flows or wicks from indication zone 216 to sink zone 218, where mixture 217 is absorbed and collected as the test proceeds to a conclusion. Arrow 222 shows the direction of wicking in monolith 210, and is typical of the monolith processing strips as discussed herein.

An alternate embodiment of a four zone monolith includes a monolith 210 configured to have an amplification zone 212, a clean-up zone 214, an indication zone 216 and a sink zone 218. In this embodiment, clean-up zone 214 provides acid or enzyme processing of a sample.

In other embodiments, a monolith can have more than four zones, such as a five zone monolith for performing molecular diagnostic tests for RNA based biological samples with the following zones: clean-up, reverse transcription of RNA to complementary DNA, amplification of DNA generated, indication and sink.

FIG. 14 is a top view of an embodiment of a reinforced monolith 300. FIG. 14 shows monolith 310 disposed on substrate 330. In an alternate embodiment, monolith 310 can be used without substrate 330. Monolith 310, with or without substrate 330, can be used to process fluid samples in a variety of possible configurations, such as being configured as a test stick to perform molecular diagnostic tests. Substrate 330 reinforces and strengthens monolith 310 and can prevent breakage of monolith 310 during assembly, shipping and handling. Substrate 330 can be in a variety of configurations, such as: a carrier, a support, a frame or a tray. Monolith 310 includes cleanup zone 312, reaction zone 314, indication zone 316 and sink zone 318. FIG. 14 shows the flow of fluid mixture 313 from cleanup zone 312 to reaction zone 314. Mixture 315 exits reaction zone 314 and proceeds to indication zone 316. Mixture 317 exits indication zone 316 and proceeds to sink zone 318. Indication zone 316 includes indication spots 320 and an opening or window 332 in substrate 330 to enable an optical source and/or an optical sensor to be able to optically access the indication spots 320 from both above and below monolith 310.

Optionally, an optically readable code (not shown in the figures) can be added to a monolith, or to the substrate 330 shown in FIGS. 14 and 15, to provide a serial number, a product code, a test code or any combination thereof, which can be read by an optical sensor configured to read the indication test results in indication zone 316.

FIG. 15 shows a side view of the reinforced monolith 300 of FIG. 14. Monolith 310 is disposed on substrate 330 and flow proceeds from left to right from cleanup zone 312 to reaction zone 314 to indication zone 316 to sink zone 318.

Also shown in FIG. 14 and FIG. 15, indication zone 316 includes a neck region, i.e., a change in the lateral cross-sectional area of this zone. This narrowing of indication zone 316 is for the purpose of slowing down the flow of mixture 315 as it enters indication zone 316, thereby increasing the amount of time for chemical reactions to occur in reaction zone 314 and providing a prolonged flow of mixture 315 into the indication zone 320 compared to a configuration without this restriction. If a target nucleic acid sequence is in mixture 315, then the chemical reactions in indication zone 316 will cause a change in the wavelength and/or intensity of the light emerging from indication zone 316 and detected by an optical sensor, as shown in FIG. 19. The thinness of indication zone 316 from top to bottom reduces the attenuation of any light transmitted through indication zone 316 as part of the process of detecting the results of the test in zone 316.

A zone in a monolith can be configured with two or more parallel sub-zones for parallel processing within that zone as exemplified in FIGS. 15-18. FIG. 16 shows an embodiment of a monolith 510 with two parallel cleanup zones. Monolith 510 includes cleanup zone 512A and 512B which operate in parallel. Both cleanup zones receive a portion of mixture 102. Mixture 102 is processed in two parallel cleanup zones 512A and 512B, which can have different process chemistries and the output flows 513A and 513B are combined together as mixture flow proceeds to reaction zone 514. Mixture 515 flows from the reaction zone 514 to indication zone 516 which includes indication spots 520. Mixture 517 flows from indication zone 516 to cleanup zone 518.

FIG. 17 shows an embodiment of a monolith 610 with two parallel reaction zones 614A and 614B, enabling two different reaction processes to occur in the same monolith 610. Monolith 610 includes cleanup zone 612 which receives a mixture 102. The output flow of cleanup zone 612 is split into two mixtures 613A and 613B, which flow into respective parallel reaction zones 614A and 614B. The output flows 615A and 615B of respective parallel reaction zones 614A and 614B flow into indication zone 616. Indication zone 616 includes indication spots 620. The output flow 617 of reaction zone 616 flows to sink zone 618.

FIG. 18 shows an embodiment of a monolith 710 with parallel indication spots 716A and 716B. Monolith 710 includes cleanup zone 712, reaction zone 714, indication spots 716A and 716B and sink zone 718. Mixture 713 flows from cleanup zone 712 to reaction zone 714. Mixtures 715A and 715B flow into respective indication spots 716A and 716B. Indication spots 716A and 716B include respective indication spots 720A and 720B. Mixtures 717A and 717B flow from respective indication spots 716A and 716B into sink zone 718. During the processing of mixtures 715A and 715B, indication of two or more target nucleic acid sequences can be done in separate indication spots 716A and 716B using either one or two optical sensors as needed for a particular testing application.

FIG. 19 shows a block diagram of an apparatus 800 for the processing or testing of fluid samples, such as, for example, molecular diagnostic tests. Apparatus 800 includes test dock 850 and test stick 840. Test stick 840 comprises a monolith as previously described herein, including exemplary monoliths 210, 310, 510, 610 and 710 as respectively shown and described with respect to FIGS. 13-18. Test dock 850 includes heater system 880 which includes a heater and a temperature sensor, controller 855, optical source 860, optical sensor 865, interface 870 and an internal power source such as a battery (not shown).

In some embodiments, heater system 880 can be included in test stick 840 and is coupled to controller 855 in test dock 850. In some embodiments, optical source 860 and optical sensor 865 can be included in test stick 840 and are coupled to controller 855 in test dock 850.

Apparatus 800 can be used to determine if fluid sample 102 contains an analyte, such as a particular bacteria, virus, fungus, parasite, etc. by detecting one or more target nucleic acid sequences composed of RNA or DNA in fluid sample 102. Each test stick can be configured to detect at least one target nucleic acid sequence, such as for a specific pathogen, for example, hepatitis B, hepatitis C, H1N1 flu virus, etc. Test stick 840 can be configured as a disposable, one time use test stick which connects to test dock 850, which provides electrical power and the electronic systems needed to perform a diagnostic test. Test dock 850 can be disconnected from a test stick 840 after a diagnostic test and used with a new test stick 840 for another test. Test dock 850 and test stick 840 can be configured to be coupled together using a variety of techniques, which are not shown in FIG. 19.

Cleanup zone 812 processes fluid sample 102 and produces mixture 813, which flows or wicks to reaction zone 814. Reaction zone 814 processes mixture 813 received from cleanup zone 812 and produces mixture 815, which flows or wicks to indication zone 816. Indication zone 816 processes mixture 815 received from reaction zone 814 and produces mixture 817, which flows or wicks to sink zone 818. Sink zone 818 absorbs mixture 817, ending the processing of fluid 102 that was input into test stick 840. Mixture 102 is processed into mixture 813, then mixture 813 is further processed into mixture 815 and mixture 815 is processed into mixture 817, which ends the processing in test stick 840. After fluid sample 102 has been deposited and flows into cleanup zone 812, fluid sample 102 is processed by various chemicals and reagents which have been stored within cleanup zone 812 of test stick 840. In other embodiments, there can be more than four sequentially coupled fluid processing zones.

Test dock 850 is connected by wire or wirelessly to communications device 875 for the readout of the test results. Heater system 880 including a heater and temperature sensor are thermally coupled to reaction zone 814 and heater system 880 regulates the temperature of reaction zone 814 to support the amplification of DNA in reaction zone 814, whether the temperature control required is isothermal or otherwise. The detection of the flow of mixture 815 into indication zone 816 can be done using optical sensor 865 in conjunction with optical source 860, as optical source 860 shines through indication spots 820 in indication zone 816 and to optical sensor 865. Indication zone 816 processes mixture 815 and the resultant mixture will produce either a change in the wavelength and/or intensity of the light received by optical sensor 865 if a target nucleic acid sequence has been found to be present in fluid sample 102. The optical data received by optical sensor 865 is sent to controller 855 via link 854, where it can be sent to interface 870 via link 852. Interface 870 can send the data to computer or communications device 875 via a wired or wireless link 872. Computer or communications device 875 can process the received data and determine if the target nucleic acid sequence has or has not been detected in fluid mixture 102 and provide an audio and/or visual message to the operator of apparatus 800 as to the test results. In some embodiments, the controller can determine if the target nucleic acid sequence has or has not been detected in fluid sample 102 and send communications or messages to communications device 875 via interface 870 to notify the operator of apparatus 800 of the test results.

Test stick 840 can include any of a variety of mechanical indicators, electronic tags, such as RFID tags or optically readable unique identifiers which can be read by test dock 850 at the start of a test to identify the type of test stick 840 that is connected to test dock 850 and the type of test protocol to be followed by controller 855 and communications device 875 during the test, such as the timing of any heating process to be conducted during a test.

In an alternate embodiment (not shown), an optical source can be adjacent to optical sensor 865 below the indication spots 820 of test stick 840. In such an alternate embodiment, the optical source would illuminate the indication spots 820 from below and the optical sensor 865 would detect the light reflected or emitted by the indication spots 820 and detect a change in wavelength and/or intensity of the light.

Controller 855 can be a microprocessor, an ASIC, a state machine or other type of processor configured to receive the optical data from optical sensor 865. Communications device 875 can be coupled to a telecommunications network or to a web service on the Internet to provide access to a database where the test results can be stored for further analysis. Communications device 875 can be a cellphone, a smartphone, a tablet, a personal computer or other device with suitable computer and communications capabilities.

FIG. 20 shows a diagram of an apparatus 900 for the fabrication of multi-zone monolith 910. FIG. 20 shows a side view of monolith 910 that will form in mold 905. After fabrication, monolith 910 can include various fluid processing zones such as, for example: clean-up zone 912, reaction zone 914, indication zone 916 and sink zone 918. The zones are separated by transitions 913, 915 and 917. Nozzles 922, 924, 926 and 928 of multichannel dispenser 920 are positioned above mold 905, where monolith 910 will form after polymerization of at least one hydrophilic monomer, at least one linker monomer, at least one porogenic solvent and at least one initiator. It should be understood that apparatus 900 is an exemplary configuration with four zones and a similar apparatus could be used to form monoliths with more or less than four zones by, for example, using more or less than four nozzles. Various types and versions of monoliths can be fabricated with apparatus 900.

Each of the nozzles of dispenser 920 may be filled with a customized mixture of solvent, monomers and other chemicals as needed during polymerization to form the individual zones of monolith 910. Nozzle 922 an contain chemical mix 932 needed to form zone 932. Nozzle 924 can contain chemical mix 934 needed to form zone 914. Nozzle 926 can contain chemical mix 936 used to form zone 916. Nozzle 928 can contain chemical mix 938 used to form zone 918. In an alternate embodiment of the fabricating apparatus 900, multiple serial and/or parallel regions within any of the zones of a monolith can be fabricated by adding more nozzles to dispenser 920 positioned above the zones to have such regions. A method for the use of the fabricating apparatus of FIG. 20 is described herein with respect to FIG. 21.

FIG. 21 lists a method 1000 of steps for fabricating a monolith, such as monoliths 210, 310 and the monolith test stick 840 shown in respective FIGS. 13, 14 and 19 or various other monoliths using a fabrication apparatus similar to the one shown in FIG. 20, where the monolith comprises a three dimensional self-wicking polymer. Step 1001 provides a mold 905 configured for the fabrication of monolith 910. Step 1002 defines a plurality of zones 912, 914, 916 and 918 in the mold, such as by the positioning of nozzles 922, 924, 926 and 928 above the associated respective zones of mold 905 in FIG. 20. Step 1003 provides a plurality of containers, nozzles 922, 924, 926 and 928, where each one of the plurality of containers is associated with one of the plurality of zones.

Step 1004 dispenses one or more monomers of a plurality of hydrophilic monomers into one of the plurality of containers. Step 1005 dispenses one or more porogenic solvents of a plurality of porogenic solvents into one of the plurality of containers. Optional step 1006 dispenses one or more monomers of a plurality of linker monomers into one of the plurality of containers. Optional step 1007 dispenses one or more initiators of a plurality of initiators into one of the plurality of containers. Optional step 1008 may repeat steps 1004, 1005, 1006 and 1007 until each of the plurality of containers has received at least one monomer, at least one porogenic solvent, at least one linker monomer and at least one initiator.

Optional step 1009 mixes the contents of each one of the plurality of containers. Step 1010 meters the contents of each one of the plurality of containers into each one of the respective plurality of zones in the mold. Step 1011 initiates polymerization of the contents of the mold. Step 1012 completes polymerization of the contents of the mold and thus forms the monolith. Step 1013 washes any remaining solvent from the monolith.

FIG. 22 shows a diagram of an apparatus 1100 for the fabrication of monolith 1110. FIG. 22 shows a side view of monolith 1110 that will form in mold 1105. After fabrication, monolith 1110 can include various fluid processing zones such as, for example: cleanup zone 1112, reaction zone 1114, indication one 1116 and ink zone 1118. The zones are separated by removable dividers 1113, 1115 and 1117. Nozzles 1122, 1124, 1126 and 1128 of multichannel dispenser 1120 are positioned above mold 1105, where monolith 1110 will form after polymerization of at least one hydrophilic monomer, at least one linker monomer, at least one porogenic solvent and at least one initiator. It should be understood that apparatus 1100 is an exemplary configuration with four zones and a similar apparatus could be used to form monoliths with less than or more than four zones by, for example, using less than or more than four nozzles.

Each of the nozzles of dispenser 1120 can be filled with a customized mixture of solvent, monomers and other chemicals as are needed during polymerization to form the individual zones of monolith 1110. Nozzle 1122 can contain chemical mix 1132 needed to form zone 1112. Nozzle 1124 can contain chemical mix 1134 needed to form zone 1114. Nozzle 1126 can contain chemical mix 1136 used to form zone 1116. Nozzle 1128 can contain chemical mix 1138 used to form zone 1118. A method for the use of the fabricating apparatus of FIG. A11 is described herein with respect to FIG. 23.

FIG. 23 lists method 1200 for fabricating monolith 1110, using dividers and the apparatus of FIG. 22, where the monolith comprises a self-wicking polymer. Step 1201 provides mold 1105 and a plurality of dividers 1113, 1115 and 1117 configured for the fabrication of monolith 1110. Step 1202 positions the plurality of dividers in the mold to define the plurality of zones. Step 1203 provides a plurality of containers, where each one of the plurality of containers is associated with one of the plurality of zones.

Step 1204 dispenses one or more monomers of a plurality of hydrophilic monomers into one of the plurality of containers. Step 1205 dispenses one or more porogenic solvents of a plurality of porogenic solvents into one of the plurality of containers. Step 1206 dispenses one or more monomers of a plurality of linker monomers into one of the plurality of containers. Step 1207 dispenses one or more initiators of a plurality of initiators into one of the plurality of containers. Step 1208 repeats steps 1204, 1205, 1206 and 1207 until each of the plurality of containers has received at least one monomer, at least one porogenic solvent, at least one linker monomer and at least one initiator.

Step 1209 mixes the contents of each one of the plurality of containers, Step 1210 meters the contents of each one of the plurality of containers into each one of the respective plurality of zones in the mold. Step 1211 initiates polymerization of the contents of the mold. In step 1212, the status of the polymerization in the mold is monitored by, for example, using optical methods. Step 1213 removes the plurality of dividers from the mold before the contents solidify. The timing of the removal of the plurality of the dividers can vary depending on the desired state of polymerization to be achieved, prior to the removal of the dividers. Step 1214 completes polymerization of the contents of the mold and thus forming one contiguous monolith. Step 1215 washes remaining solvent from the monolith.

After a monolith has been formed as described above, then the monolith can be loaded with various reagents in the zones that are needed to provide some of the different functions of each zone. The reagents needed for each zone may be applied as liquids which will wick into the zone or a region within a zone and be stored within the zones previously created. Alternatively or additionally, the monolith may be further derivatized, for example, by hydrolysis and/or covalent grafting. A monolith can optionally be dried with the stored reagent(s).

Some Advantages of the Monoliths of the Present Invention

Monoliths of the present invention demonstrate a number of advantages as compared to previously known monoliths. Among other advantages, readily apparent to the skilled person, they may, in some embodiments as described herein:

allow processing of samples without external pumping.

be more efficient and cost effective to manufacture and use.

possess superior mechanical properties, making them easier to handle.

permit a broad range of functionalities to be incorporated. For example, monoliths of the present invention may provide a complete "lab on a stick" diagnostic or analytical assay. In other words, monoliths of the invention may be multi-functional.

be suitable for large-volume sample processing (through elimination of the requirement for a thin-film format in the wicking device).

facilitate detection by permitting transillumination to be used.

be configured, as described herein, to perform chemical reactions, for example, cell lysis, protein denaturation, or analyte amplification.

It is to be understood that the examples and modifications described herein are for illustrative purposes only and that various modifications or changes in light thereof will be suggested to persons skilled in the art and are to be included within the spirit of this application and scope of the appended claims. All publications, patents and patent applications cited herein are hereby incorporated by reference in their entirety for all purposes.

We claim:

1. A method of fabricating a self-wicking monolith for processing a fluid sample, the method comprising:

providing at least one hydrophilic monomer and at least one linker monomer, the at least one linker monomer having two polymerizable groups spaced apart by a linker comprising at least one —C(R)$_2$O— group; wherein each R is individually a hydrogen or an organic group;

obtaining a polymerizable composition by combining the at least one hydrophilic monomer and the at least one linker monomer in a porogenic solvent;

obtaining at least one additional polymerizable composition containing the at least one monomer and the at least one linker monomer in the porogenic solvent, wherein the polymerizable composition and the at least one additional polymerizable composition vary in at least one of:

the at least one hydrophilic monomer and/or the at least one linker monomer identity;

the total non-linker monomer to the at least one linker monomer ratio;

the porogenic solvent;

the concentration of the at least one hydrophilic monomer, the at least one linker monomer, and a further monomer, if present, in the solution;

the presence and identity of one or more further monomers, or the presence and identity of an initiator;

providing the polymerizable composition and the at least one additional polymerizable composition at different locations within a mold prior to polymerization; and polymerizing the polymerizable composition and the at least one additional polymerizable composition at the same time to form the self-wicking monolith, such that the self-wicking monolith comprises a plurality of zones, wherein different zones have different wicking properties and/or chemical properties.

2. The method of claim 1, wherein each of the polymerizable groups of the at least one linker monomer comprises a vinylic moiety.

3. The method of claim 1, wherein the at least one linker monomer is selected from the group consisting of:
—O—CH$_2$—CH$_2$—O—;
(—O—CH$_2$—CH$_2$—)$_n$—O—, wherein n is selected from 2, 3, 4, or 5;
—O—CH$_2$—CH(OH)—CH$_2$—O—;
—O—CH$_2$—CH(OH)—CH$_2$—CH(OH)—CH$_2$—CH(OH)—CH$_2$—O—; and
—OCH$_2$—C(CH$_2$O—)(CH$_2$CH$_3$)—CH$_2$O—.

4. The method of claim 1, wherein the at least one linker monomer is selected from the group consisting of ethyleneglycol diacrylate, ethyleneglycol dimethacrylate, tetra(ethylene glycol) dimethacrylate, tetra(ethylene glycol) diacrylate, and di(ethylene glycol) dimethacrylate.

5. The method of claim 1, wherein the at least one hydrophilic monomer is an acrylate or methacrylate.

6. The method of claim 1, wherein the at least one hydrophilic monomer is 2-hydroxyethyl methacrylate, 2-hydroxyacrylate, 2-hydroxyethyl acrylate, 2-hydroxypropyl methacrylate or 2-hydroxypropyl acrylate.

7. The method of claim 1, further comprising providing at least one additional linker monomer wherein the at least one additional linker monomer is combined in the polymerizable composition.

8. The method of claim 1, further comprising providing at least one further monomer wherein the at least one further monomer is combined in the polymerizable composition.

9. The method of claim 8, wherein the at least one further monomer is functionalized and bears a moiety selected from the group consisting of:

a chemically reactive group suitable for reaction with a reactive group of a graftable compound to covalently graft the compound to the monolith;

a pH sensitive group;

a group suitable for direct immobilisation of an analyte;

a dye, fluorophore, chromophore, or quencher;

an immobilised protein; and immobilised natural or artificial nucleic acid molecules.

10. The method of claim 9, wherein the at least one further functionalized monomer comprises at least one of the following side chains or groups: amino, carboxyl, polyethylene glycol, alkyl, maleimide, succinimide, acyl halide, sulfhydryl or azide.

11. The method of claim 9, wherein the at least one further functionalized monomer is an amino methacrylate, an amino acrylate, acrylic acid or methacrylic acid.

12. The method of claim 1, wherein:

the porogenic solvent is able to dissolve solid monomers, or wherein the porogenic solvent is miscible with liquid monomers; and the porogenic solvent is selected such that polymerized clusters of the at least one linker monomer precipitate from the porogenic solvent at an early point in polymerization.

13. The method of claim 1, wherein the porogenic solvent is selected from the group consisting of:

a binary mixture containing an alkane and an alcohol;

a binary mixture containing an aromatic solvent and an alcohol;

a binary mixture containing an alcohol and a dial;

a binary mixture containing an alcohol and water;

a ternary mixture containing an alcohol, a diol and water; and a mixture containing at least 10% (v/v) surfactant.

14. The method of claim 1, wherein at least two zones are ordered sequentially or in parallel along an intended wicking direction of the monolith.

15. The method of claim 1, wherein the monolith is further derivatized or modified wherein the derivatization or modification comprises at least one of the following:
  a chemical hydrolysis,
  a covalent grafting of a graftable compound to the monolith, or
  an impregnation of the monolith with one or more components.

16. The method of claim 1, wherein at least one of the zones is an amplification zone which is configured to facilitate amplification of a target nucleic acid sequence or whole-genome amplification in a fluid sample.

17. The method of claim 1, wherein at least one of the zones is a clean-up zone which is configured to facilitate lysis of cells or viruses in a fluid sample.

18. The method of claim 1, wherein at least one of the zones is a reverse transcription zone which is configured to facilitate transcription of RNA to cDNA.

19. The method of claim 1, wherein at least one of the zones is an indication zone comprising a dye fluorophore, a chromophore, or a quencher, wherein the indication zone is configured to facilitate detection of an analyte molecule.

20. The method of claim 1, wherein at least one of the zones is configured to retard or retain one or more components of the sample such that an analyte is separated from other components in the sample.

21. The method of claim 1, wherein at least one of the zones is configured to facilitate a chemical transformation of one or more components of the sample.

22. The method of claim 1, wherein the external dimensions of the monolith are:
  Length: between 1 and 10 cm;
  Width: between 2 and 25 mm; and
  Depth: between 1 and 10 mm.

23. The method of claim 1, wherein the total linker monomer to total hydrophilic monomer ratio for each of the polymerizable composition and the at least one additional polymerizable composition is between 1:1 and 10:1.

24. The method of claim 1, wherein the bulk density of the monolith is between 0.15 and 0.50 g/cc.

25. The method of claim 1, wherein the monolith comprises one or more regions having a porosity of 50 to 85%.

26. The method according to claim 1, wherein the polymerizable composition and the at least one additional polymerizable composition abut each other in the mold; and polymerizing the abutting polymerizable composition and the at least one additional polymerizable composition occurs at the same time.

27. The method of claim 1, wherein the plurality of polymerizable compositions at different locations within the mold are separated by dividers.

28. The method of claim 27, further comprising removing the dividers part way through polymerization.

29. A method of fabricating a self-wicking monolith for processing a fluid sample, the method comprising:
  providing at least one hydrophilic monomer and at least one linker monomer, the at least one linker monomer having two polymerizable groups spaced apart by a linker comprising at least one —C(R)$_2$O— group:
    wherein each R is individually a hydrogen or an organic group;
  obtaining a polymerizable composition by combining the at least one hydrophilic monomer and the at least one linker monomer in a porogenic solvent;
  obtaining at least one additional polymerizable composition containing the at least one monomer and the at least one linker monomer in the porogenic solvent, wherein the polymerizable composition and the at least one additional polymerizable composition vary in at least one of:
    the at least one hydrophilic monomer and/or the at least one linker monomer identity;
    the total non-linker monomer to the at least one linker monomer ratio;
    the porogenic solvent;
    the concentration of the at least one hydrophilic monomer, the at least one linker monomer, and a further monomer, if present, in the solution;
    the presence and identity of one or more further monomers, or
    the presence and identity of an initiator;
  providing the polymerizable composition and the at least one additional polymerizable composition at different locations within a mold prior to polymerization; and
  polymerizing the polymerizable composition and the at least one additional polymerizable composition to form the self-wicking monolith, such that the self-wicking monolith comprises a plurality of zones, wherein different zones have different wicking properties and/or chemical properties, and wherein at least one of the zones is an amplification zone which is configured to facilitate amplification of a target nucleic acid sequence or whole-genome amplification in a fluid sample.

30. The method of claim 29, wherein each of the polymerizable groups of the at least one linker monomer comprises a vinylic moiety.

31. The method of claim 29, wherein the at least one linker monomer is selected from the group consisting of:
  —O—CH$_2$—CH$_2$—O—;
  (—O—CH$_2$—CH$_2$—)$_n$—O—, wherein n is selected from 2, 3, 4, or 5;
  —O—CH$_2$—CH(OH)—CH$_2$—O—;
  —O—CH$_2$—CH(OH)—CH$_2$—CH(OH)—CH$_2$—CH(OH)—CH$_2$—O—; and
  —OCH$_2$—C(CH$_2$O—)(CH$_2$CH$_3$)—CH$_2$O—.

32. The method of claim 29, wherein the at least one linker monomer is selected from the group consisting of ethyleneglycol diacrylate, ethyleneglycol dimethacrylate, tetra(ethylene glycol) dimethacrylate, tetra(ethylene glycol) diacrylate, and di(ethylene glycol) dimethacrylate.

33. The method of claim 29, wherein the at least one hydrophilic monomer is an acrylate or methacrylate.

34. The method of claim 29, wherein the at least one hydrophilic monomer is 2-hydroxyethyl methacrylate, 2-hydroxyacrylate, 2-hydroxyethyl acrylate, 2-hydroxypropyl methacrylate or 2-hydroxypropyl acrylate.

35. The method of claim 29, further comprising providing at least one additional linker monomer wherein the at least one additional linker monomer is combined in the polymerizable composition.

36. The method of claim 29, further comprising providing at least one further monomer wherein the at least one further monomer is combined in the polymerizable composition.

37. The method of claim 36, wherein the at least one further monomer is functionalized and bears a moiety selected from the group consisting of:
  a chemically reactive group suitable for reaction with a reactive group of a graftable compound to covalently graft the compound to the monolith;
  a pH sensitive group;
  a group suitable for direct immobilisation of an analyte;
  a dye, fluorophore, chromophore, or quencher;
  an immobilised protein; and
  immobilised natural or artificial nucleic acid molecules.

38. The method of claim 37, wherein the at least one further functionalized monomer comprises at least one of the following side chains or groups: amino, carboxyl, polyethylene glycol, alkyl, maleimide, succinimide, acyl halide, sulfhydryl or azide.

39. The method of claim 37, wherein the at least one further functionalized monomer is an amino methacrylate, an amino acrylate, acrylic acid or methacrylic acid.

40. The method of claim 29, wherein:
the porogenic solvent is able to dissolve solid monomers, or wherein the porogenic solvent is miscible with liquid monomers; and
the porogenic solvent is selected such that polymerized clusters of the at least one linker monomer precipitate from the porogenic solvent at an early point in polymerization.

41. The method of claim 29, wherein the porogenic solvent is selected from the group consisting of:
a binary mixture containing an alkane and an alcohol;
a binary mixture containing an aromatic solvent and an alcohol;
a binary mixture containing an alcohol and a diol;
a binary mixture containing an alcohol and water;
a ternary mixture containing an alcohol, a diol and water; and
a mixture containing at least 10% (v/v) surfactant.

42. The method of claim 29, wherein at least two zones are ordered sequentially or in parallel along an intended wicking direction of the monolith.

43. The method of claim 29, wherein the monolith is further derivatized or modified wherein the derivatization or modification comprises at least one of the following:
a chemical hydrolysis,
a covalent grafting of a graftable compound to the monolith, or
an impregnation of the monolith with one or more components.

44. The method of claim 29, wherein at least one of the zones is a clean-up zone which is configured to facilitate lysis of cells or viruses in a fluid sample.

45. The method of claim 29, wherein at least one of the zones is a reverse transcription zone which is configured to facilitate reverse transcription of RNA to cDNA.

46. The method of claim 29, wherein at least one of the zones is an indication zone comprising a dye fluorophore, a chromophore, or a quencher, wherein the indication zone is configured to facilitate detection of an analyte molecule.

47. The method of claim 29, wherein at least one of the zones is configured to retard or retain one or more components of the sample such that an analyte is separated from other components in the sample.

48. The method of claim 29, wherein at least one of the zones is configured to facilitate a chemical transformation of one or more components of the sample.

49. The method of claim 29, wherein the external dimensions of the monolith are:
Length: between 1 and 10 cm;
Width: between 2 and 25 mm; and
Depth: between 1 and 10 mm.

50. The method of claim 29, wherein the total linker monomer to total hydrophilic monomer ratio for each of the polymerizable composition and the at least one additional polymerizable composition is between 1:1 to 10:1.

51. The method of claim 29, wherein the bulk density of the monolith is between 0.15 and 0.50 Woo.

52. The method of claim 29, wherein the monolith comprises one or more regions having a porosity of 50 to 85%.

53. The method of claim 29, wherein the polymerizable composition and the at least one additional polymerizable composition abut each other in the mold; and polymerizing the abutting polymerizable composition and the at least one additional polymerizable composition occurs at the same time.

54. The method of claim 29, wherein the polymerization of at least two of the compositions occurs at different times.

55. The method of claim 29, wherein the plurality of polymerizable compositions at different locations within the mold are separated by dividers.

56. The method of claim 55, further comprising removing the dividers part way through polymerization.

57. A method of fabricating a self-wicking monolith for processing a fluid sample, the method comprising:
providing at least one hydrophilic monomer and at least one linker monomer, the at least one linker monomer having two polymerizable groups spaced apart by a linker comprising at least one —C(R)$_2$O— group; wherein each R is individually a hydrogen or an organic group;
obtaining a polymerizable composition by combining the at least one hydrophilic monomer and the at least one linker monomer in a porogenic solvent;
obtaining at least one additional polymerizable composition containing the at least one monomer and the at least one linker monomer in the porogenic solvent, wherein the polymerizable composition and the at least one additional polymerizable composition vary in at least one of:
the at least one hydrophilic monomer and/or the at least one linker monomer identity;
the total non-linker monomer to the at least one linker monomer ratio;
the porogenic solvent;
the concentration of the at least one hydrophilic monomer, the at least one linker monomer, and a further monomer, if present, in the solution;
the presence and identity of one or more further monomers, or
the presence and identity of an initiator;
providing the polymerizable composition and the at least one additional polymerizable composition at different locations within a mold prior to polymerization; and
polymerizing the polymerizable composition and the at least one additional polymerizable composition to form the self-wicking monolith, such that the self-wicking monolith comprises a plurality of zones, wherein different zones have different wicking properties and/or chemical properties, and wherein at least one of the zones is a clean-up zone which is configured to facilitate lysis of cells or viruses in a fluid sample.

58. The method of claim 57, wherein each of the polymerizable groups of the at least one linker monomer comprises a vinylic moiety.

59. The method of claim 57, wherein the at least one linker monomer is selected from the group consisting of:
—O—CH$_2$—CH$_2$—O—;
(—O—CH$_2$—CH$_2$—)$_n$—O—, wherein n is selected from 2, 3, 4, or 5;
—O—CH$_2$—CH(OH)—CH$_2$—O—;
—O—CH$_2$—CH(OH)—CH$_2$—CH(OH)—CH$_2$—CH(OH)—CH$_2$—O—; and
—OCH$_2$—C(CH$_2$O—)(CH$_2$CH$_3$)—CH$_2$O—.

60. The method of claim 57, wherein the at least one linker monomer is selected from the group consisting of ethyleneglycol diacrylate, ethyleneglycol dimethacrylate, tetra(ethylene glycol) dimethacrylate, tetra(ethylene glycol) diacrylate, and di(ethylene glycol) dimethacrylate.

61. The method of claim 57, wherein the at least one hydrophilic monomer is an acrylate or methacrylate.

62. The method of claim 57, wherein the at least one hydrophilic monomer is 2-hydroxyethyl methacrylate, 2-hydroxyacrylate, 2-hydroxyethyl acrylate, 2-hydroxypropyl methacrylate or 2-hydroxypropyl acrylate.

63. The method of claim 57, further comprising providing at least one additional linker monomer wherein the at least one additional linker monomer is combined in the polymerizable composition.

64. The method of claim 57, further comprising providing at least one further monomer wherein the at least one further monomer is combined in the polymerizable composition.

65. The method of claim 64, wherein the at least one further monomer is functionalized and bears a moiety selected from the group consisting of:
a chemically reactive group suitable for reaction with a reactive group of a graftable compound to covalently graft the compound to the monolith;
a pH sensitive group;
a group suitable for direct immobilisation of an analyte;
a dye, fluorophore, chromophore, or quencher;
an immobilised protein; and
immobilised natural or artificial nucleic acid molecules.

66. The method of claim 65, wherein the at least one further functionalized monomer comprises at least one of the following side chains or groups: amino, carboxyl, polyethylene glycol, alkyl, maleimide, succinimide, acyl halide, sulfhydryl or azide.

67. The method of claim 65, wherein the at least one further functionalized monomer is an amino methacrylate, an amino acrylate, acrylic acid or methacrylic acid.

68. The method of claim 57, wherein:
the porogenic solvent is able to dissolve solid monomers, or wherein the porogenic solvent is miscible with liquid monomers; and
the porogenic solvent is selected such that polymerized clusters of the at least one linker monomer precipitate from the porogenic solvent at an early point in polymerization.

69. The method of claim 57, wherein the porogenic solvent is selected from the group consisting of:
a binary mixture containing an alkane and an alcohol;
a binary mixture containing an aromatic solvent and an alcohol;
a binary mixture containing an alcohol and a diol;
a binary mixture containing an alcohol and water;
a ternary mixture containing an alcohol, a diol and water; and
a mixture containing at least 10% (v/v) surfactant.

70. The method of claim 57, wherein at least two zones are ordered sequentially or in parallel along an intended wicking direction of the monolith.

71. The method of claim 57, wherein the monolith is further derivatized or modified wherein the derivatization or modification comprises at least one of the following:
a chemical hydrolysis,
a covalent grafting of a graftable compound to the monolith, or
an impregnation of the monolith with one or more components.

72. The method of claim 57, wherein at least one of the zones is an amplification zone which is configured to facilitate amplification of a target nucleic acid sequence or whole-genome amplification in a fluid sample.

73. The method of claim 57, wherein at least one of the zones is a reverse transcription zone which is configured to facilitate reverse transcription of RNA to cDNA.

74. The method of claim 57, wherein at least one of the zones is an indication zone comprising a dye fluorophore, a chromophore, or a quencher, wherein the indication zone is configured to facilitate detection of an analyte molecule.

75. The method of claim 57, wherein at least one of the zones is configured to retard or retain one or more components of the sample such that an analyte is separated from other components in the sample.

76. The method of claim 57, wherein at least one of the zones is configured to facilitate a chemical transformation of one or more components of the sample.

77. The method of claim 57, wherein the external dimensions of the monolith are;
Length: between 1 and 10 cm;
Width: between 2 and 25 mm; and
Depth: between 1 and 10 mm.

78. The method of claim 57, wherein the total linker monomer to total hydrophilic monomer ratio for each of the polymerizable composition and the at least one additional polymerizable composition is between 1:1 to 10:1.

79. The method of claim 57, wherein the bulk density of the monolith is between 0.15 and 0.50 g/cc.

80. The method of claim 57, wherein the monolith comprises one or more regions having a porosity of 50 to 85%.

81. The method of claim 57, wherein the polymerizable composition and the at least one additional polymerizable composition abut each other in the mold; and polymerizing the abutting polymerizable composition and the at least one additional polymerizable composition occurs at the same time.

82. The method of claim 57, wherein the polymerization of at least two of the compositions occurs at different times.

83. The method of claim 57, wherein the plurality of polymerizable compositions at different locations within the mold are separated by dividers.

84. The method of claim 83, further comprising removing the dividers part way through polymerization.

85. A method of fabricating a self-wicking monolith for processing a fluid sample, the method comprising:
providing at least one hydrophilic monomer and at least one linker monomer, the at least one linker monomer having two polymerizable groups spaced apart by a linker comprising at least one —$C(R)_2O$— group; wherein each R is individually a hydrogen or an organic group;
obtaining a polymerizable composition by combining the at least one hydrophilic monomer and the at least one linker monomer in a porogenic solvent;
obtaining at least one additional polymerizable composition containing the at least one monomer and the at least one linker monomer in the porogenic solvent, wherein the polymerizable composition and the at least one additional polymerizable composition vary in at least one of:
the at least one hydrophilic monomer and/or the at least one linker monomer identity;
the total non-linker monomer to the at least one linker monomer ratio;
the porogenic solvent;
the concentration of the at least one hydrophilic monomer, the at least one linker monomer, and a further monomer, if present, in the solution;
the presence and identity of one or more further monomers, or the presence and identity of an initiator;
providing the polymerizable composition and the at least one additional polymerizable composition at different locations within a mold prior to polymerization; and
polymerizing the polymerizable composition and the at least one additional polymerizable composition to form the self-wicking monolith, such that the self-wicking monolith comprises a plurality of zones, wherein different zones have different wicking properties and/or chemical properties, and wherein at least one of the zones is a reverse transcription zone which is configured to facilitate reverse transcription of RNA to cDNA.

86. The method of claim 85, wherein each of the polymerizable groups of the at least one linker monomer comprises a vinylic moiety.

87. The method of claim 85, wherein the at least one linker monomer is selected from the group consisting of:
—O—$CH_2$—$CH_2$—O—;
(—O—$CH_2$—$CH_2$—)$_n$—O—, wherein n is selected from 2, 3, 4, or 5;
—O—$CH_2$—CH(OH)—$CH_2$—O—;
—O—$CH_2$—CH(OH)—$CH_2$—CH(OH)—$CH_2$—CH(OH)—$CH_2$—O—; and
—O$CH_2$—C($CH_2$O—)($CH_2CH_3$)—$CH_2$O—.

88. The method of claim 85, wherein the at least one linker monomer is selected from the group consisting of ethyleneglycol diacrylate, ethyleneglycol dimethacrylate, tetra(ethylene glycol) dimethacrylate, tetra(ethylene glycol) diacrylate, and di(ethylene glycol) dimethacrylate.

89. The method of claim 85, wherein the at least one hydrophilic monomer is an acrylate or methacrylate.

90. The method of claim 85, wherein the at least one hydrophilic monomer is 2-hydroxyethyl methacrylate, 2-hydroxyacrylate, 2-hydroxyethyl acrylate, 2-hydroxypropyl methacrylate or 2-hydroxypropyl acrylate.

91. The method of claim 85, further comprising providing at least one additional linker monomer wherein the at least one additional linker monomer is combined in the polymerizable composition.

92. The method of claim 85, further comprising providing at least one further monomer wherein the at least one further monomer is combined in the polymerizable composition.

93. The method of claim 92, wherein the at least one further monomer is functionalized and bears a moiety selected from the group consisting of:
a chemically reactive group suitable for reaction with a reactive group of a graftable compound to covalently graft the compound to the monolith;
a pH sensitive group;
a group suitable for direct immobilisation of an analyte;
a dye, fluorophore, chromophore, or quencher;
an immobilised protein; and
immobilised natural or artificial nucleic acid molecules.

94. The method of claim 93, wherein the at least one further functionalized monomer comprises at least one of the following side chains or groups: amino, carboxyl, polyethylene glycol, alkyl, maleimide, succinimide, acyl halide, sulfhydryl or azide.

95. The method of claim 93, wherein the at least one further functionalized monomer is an amino methacrylate, an amino acrylate, acrylic acid or methacrylic acid.

96. The method of claim 85, wherein:
the porogenic solvent is able to dissolve solid monomers, or wherein the porogenic solvent is miscible with liquid monomers; and
the porogenic solvent is selected such that polymerized clusters of the at least one linker monomer precipitate from the porogenic solvent at an early point in polymerization.

97. The method of claim 85, wherein the porogenic solvent is selected from the group consisting of:
a binary mixture containing an alkane and an alcohol;
a binary mixture containing an aromatic solvent and an alcohol;
a binary mixture containing an alcohol and a did;
a binary mixture containing an alcohol and water;
a ternary mixture containing an alcohol, a diol and water; and
a mixture containing at least 10% (v/v) surfactant.

98. The method of claim 85, wherein at least two zones are ordered sequentially or in parallel along an intended wicking direction of the monolith.

99. The method of claim 85, wherein the monolith is further derivatized or modified wherein the derivatization or modification comprises at least one of the following:
a chemical hydrolysis,
a covalent grafting of a graftable compound to the monolith, or
an impregnation of the monolith with one or more components.

100. The method of claim 85, wherein at least one of the zones is an amplification zone which is configured to facilitate amplification of a target nucleic acid sequence or whole-genome amplification in a fluid sample.

101. The method of claim 85, wherein at least one of the zones is a clean-up zone which is configured to facilitate lysis of cells or viruses in a fluid sample.

102. The method of claim 85, wherein at least one of the zones is an indication zone comprising a dye fluorophore, a chromophore, or a quencher, wherein the indication zone is configured to facilitate detection of an analyte molecule.

103. The method of claim 85, wherein at least one of the zones is configured to retard or retain one or more components of the sample such that an analyte is separated from other components in the sample.

104. The method of claim 85, wherein at least one of the zones is configured to facilitate a chemical transformation of one or more components of the sample.

105. The method of claim 85, wherein the external dimensions of the monolith are:
Length: between 1 and 10 cm;
Width: between 2 and 25 mm; and
Depth: between 1 and 10 mm.

106. The method of claim 85, wherein the total linker monomer to total hydrophilic monomer ratio for each of the polymerizable composition and the at least one additional polymerizable composition is between 1:1 to 10:1.

107. The method of claim 85, wherein the bulk density of the monolith is between 0.15 and 0.50 g/cc.

108. The method of claim 85, wherein the monolith comprises one or more regions having a porosity of 50 to 85%.

109. The method of claim 85, wherein the polymerizable composition and the at least one additional polymerizable composition abut each other in the mold; and polymerizing the abutting polymerizable composition and the at least one additional polymerizable composition occurs at the same time.

110. The method of claim 85, wherein the polymerization of at least two of the compositions occurs at different times.

111. The method of claim 85, wherein the plurality of polymerizable compositions at different locations within the mold are separated by dividers.

112. The method of claim 111, further comprising removing the dividers part way through polymerization.

113. A method of fabricating a self-wicking monolith for processing a fluid sample, the method comprising:
providing at least one hydrophilic monomer and at least one linker monomer, the at least one linker monomer having two polymerizable groups spaced apart by a linker comprising at least one —C(R)$_2$O— group; wherein each R is individually a hydrogen or an organic group;
obtaining a polymerizable composition by combining the at least one hydrophilic monomer and the at least one linker monomer in a porogenic solvent;
obtaining at least one additional polymerizable composition containing the at least one monomer and the at least one linker monomer in the porogenic solvent, wherein the polymerizable composition and the at least one additional polymerizable composition vary in at least one of:
the at least one hydrophilic monomer and/or the at least one linker monomer identity;
the total non-linker monomer to the at least one linker monomer ratio;
the porogenic solvent;
the concentration of the at least one hydrophilic monomer, the at least one linker monomer, and a further monomer, if present, in the solution;
the presence and identity of one or more further monomers, or
the presence and identity of an initiator;
providing the polymerizable composition and the at least one additional polymerizable composition at different locations within a mold prior to polymerization; and polymerizing the polymerizable composition and the at least one additional polymerizable composition to form the self-wicking monolith, such that the self-wicking monolith comprises a plurality of zones, wherein different zones have different wicking properties and/or chemical properties, and wherein the external dimensions of the monolith are:
Length: between 1 and 10 cm;
Width: between 2 and 25 mm; and
Depth: between 1 and 10 mm.

114. The method of claim 113, wherein each of the polymerizable groups of the at least one linker monomer comprises a vinylic moiety.

115. The method of claim 113, wherein the at least one linker monomer is selected from the group consisting of:
—O—CH$_2$—CH$_2$—O—;
(—O—CH$_2$—CH$_2$—)$_n$—O—, wherein n is selected from 2, 3, 4, or 5;
—OCH$_2$—CH(OH)—CH$_2$—O—;
—O—CH$_2$—CH(OH)—CH$_2$—CH(OH)—CH$_2$—CH(OH)—CH$_2$—O—; and
—OCH$_2$—C(CH$_2$O—)(CH$_2$CH$_3$)—CH$_2$O—.

116. The method of claim 113, wherein the at least one linker monomer is selected from the group consisting of ethyleneglycol diacrylate, ethyleneglycol dimethacrylate, tetra(ethylene glycol) dimethacrylate, tetra(ethylene glycol) diacrylate, and di(ethylene glycol) dimethacrylate.

117. The method of claim 113, wherein the at least one hydrophilic monomer is an acrylate or methacrylate.

118. The method of claim 113, wherein the at least one hydrophilic monomer is 2-hydroxyethyl methacrylate, 2-hydroxyacrylate, 2-hydroxyethyl acrylate, 2-hydroxypropyl methacrylate or 2-hydroxypropyl acrylate.

119. The method of claim 113, further comprising providing at least one additional linker monomer wherein the at least one additional linker monomer is combined in the polymerizable composition.

120. The method of claim 113, further comprising providing at least one further monomer wherein the at least one further monomer is combined in the polymerizable composition.

121. The method of claim 120, wherein the at least one further monomer is functionalized and bears a moiety selected from:
a chemically reactive group suitable for reaction with a reactive group of a graftable compound to covalently graft the compound to the monolith;
a pH sensitive group;
a group suitable for direct immobilisation of an analyte;
a dye, fluorophore, chromophore, or quencher;
an immobilised protein; and
immobilised natural or artificial nucleic acid molecules.

122. The method of claim 121, wherein the at least one further functionalized monomer comprises at least one of the following side chains or groups: amino, carboxyl, polyethylene glycol, alkyl, maleimide, succinimide, acyl halide, sulfhydryl or azide.

123. The method of claim 121, wherein the at least one further functionalized monomer is an amino methacrylate, an amino acrylate, acrylic acid or methacrylic acid.

124. The method of claim 113, wherein:
the porogenic solvent is able to dissolve solid monomers, or wherein the porogenic solvent is miscible with liquid monomers; and
the porogenic solvent is selected such that polymerized clusters of the at least one linker monomer precipitate from the porogenic solvent at an early point in polymerization.

125. The method of claim 113, wherein the porogenic solvent is selected from the group consisting of:
a binary mixture containing an alkane and an alcohol;
a binary mixture containing an aromatic solvent and an alcohol;
a binary mixture containing an alcohol and a diol;
a binary mixture containing an alcohol and water;
a ternary mixture containing an alcohol, a diol and water; and
a mixture containing at least 10% (v/v) surfactant.

126. The method of claim 113, wherein at least two zones are ordered sequentially or in parallel along an intended wicking direction of the monolith.

127. The method of claim 113, wherein the monolith is further derivatized or modified wherein the derivatization or modification comprises at least one of the following:
a chemical hydrolysis,
a covalent grafting of a graftable compound to the monolith, or
an impregnation of the monolith with one or more components.

128. The method of claim 113, wherein at least one of the zones is an amplification zone which is configured to facilitate amplification of a target nucleic acid sequence or whole-genome amplification in a fluid sample.

129. The method of claim 113, wherein at least one of the zones is a clean-up zone which is configured to facilitate lysis of cells or viruses in a fluid sample.

130. The method of claim 113, wherein at least one of the zones is a reverse transcription zone which is configured to facilitate transcription of RNA to cDNA.

131. The method of claim 113, wherein at least one of the zones is an indication zone comprising a dye fluorophore, a chromophore, or a quencher, wherein the indication zone is configured to facilitate detection of an analyte molecule.

132. The method of claim 113, wherein at least one of the zones is configured to retard or retain one or more components of the sample such that an analyte is separated from other components in the sample.

133. The method of claim 113, wherein at least one of the zones is configured to facilitate a chemical transformation of one or more components of the sample.

134. The method of claim 113, wherein the total linker monomer to total hydrophilic monomer ratio for each of the polymerizable composition and the at least one additional polymerizable composition is between 1:1 to 10:1.

135. The method of claim 113, wherein the bulk density of the monolith is between 0.15 and 0.50 g/cc.

136. The method of claim 113, wherein the monolith comprises one or more regions having a porosity of 50 to 85%.

137. The method of claim 113, wherein the polymerizable composition and the at least one additional polymerizable composition abut each other in the mold; and polymerizing the abutting polymerizable composition and the at least one additional polymerizable composition occurs at the same time.

138. The method of claim 113, wherein the polymerization of at least two of the compositions occurs at different times.

139. The method of claim 113, wherein the plurality of polymerizable compositions at different locations within the mold are separated by dividers.

140. The method of claim 139, further comprising removing the dividers part way through polymerization.

* * * * *